US006989450B2

(12) United States Patent
Avery

(10) Patent No.: US 6,989,450 B2
(45) Date of Patent: Jan. 24, 2006

(54) SYNTHESIS OF EPOTHILONES AND RELATED ANALOGS

(75) Inventor: Mitchell A. Avery, Oxford, MS (US)

(73) Assignee: The University of Mississippi, University, MS (US)

( * ) Notice: Subject to any disclaimer, the term of this patent is extended or adjusted under 35 U.S.C. 154(b) by 138 days.

(21) Appl. No.: 09/981,312

(22) Filed: Oct. 15, 2001

(65) Prior Publication Data

US 2002/0091269 A1 Jul. 11, 2002

Related U.S. Application Data

(60) Provisional application No. 60/240,488, filed on Oct. 13, 2000.

(51) Int. Cl.
*C07D 313/00* (2006.01)
*C07D 417/06* (2006.01)

(52) U.S. Cl. ...................................... 548/204; 549/271

(58) Field of Classification Search ................. 548/204; 549/271

See application file for complete search history.

(56) References Cited

U.S. PATENT DOCUMENTS

| 5,969,145 | A | 10/1999 | Schinzer et al. |
| 6,043,372 | A | 3/2000 | Schinzer et al. |
| 6,156,905 | A | 12/2000 | Schinzer et al. |
| 6,204,388 | B1 | 3/2001 | Danishefsky et al. |
| 6,211,412 | B1 | 4/2001 | Georg et al. |
| 6,242,469 | B1 | 6/2001 | Danishefsky et al. |
| 6,262,094 | B1 | 7/2001 | Hoefle et al. |
| 6,284,781 | B1 | 9/2001 | Danishefsky et al. |
| 6,300,355 | B1 | 10/2001 | Danishefsky et al. |
| 6,316,630 | B1 | 11/2001 | Danishefsky et al. |
| 6,350,878 | B1 | 2/2002 | Altmann et al. |
| 6,380,394 | B1 | 4/2002 | Nicolaou et al. |

FOREIGN PATENT DOCUMENTS

| WO | WO 98/25929 | 6/1998 |
| WO | WO 98/54966 | 12/1998 |
| WO | WO 99/02514 | 1/1999 |
| WO | WO 99/42602 | 8/1999 |
| WO | WO 99/43653 | 9/1999 |
| WO | WO 99/54318 | 10/1999 |
| WO | WO 99/54330 | 10/1999 |
| WO | WO 99/59985 | 11/1999 |
| WO | WO 99/66028 | 12/1999 |
| WO | WO 99/67252 | 12/1999 |
| WO | WO 99/67253 | 12/1999 |
| WO | WO 01/70716 | 9/2001 |
| WO | WO 01/73103 | 10/2001 |
| WO | WO 02/08440 | 1/2002 |

OTHER PUBLICATIONS

Hofle, G.; Glaser, NO.; Leibold, T.; Sefkow, M. Epothilone A–D and their Thiazole–Modified Analog as Novel Anticancer Agents. Pure and Applied Chemistry 1999, vol. 71, pp. 2019–2024.

Zhu, B.; Panek, J.S. Total Synthesis of Epothilone A. Organic Letters 2000, vol. 2, pp. 2575–2578.

Stachel, S.J.; Chappell, M.D.; Lee, C.B.; Danishefsky, S.J.; Chou, T.C.; He, L.; Horwitz, S.B. On the Total Synthesis and Preliminary Biological Evaluations of 15(R) and 15(S) Aza–dEpoB: A Mitsunobu Inversion at C15 in Pre–E-pothilone Fragments. Organic Letters 2000, vol. 39, pp. 1637–1639.

Sawada, D.; Shibasaki, M. Enantioselective Total Synthesis of Epothilone A Using a Multifunctional Asymmetric Catalyses. Angewandte Chemie, International Edition 2000, vol. 39, pp. 209–213.

Kalesse, M.; Quitschalle, M.; Claus, E.; Gerlach, K.; Pahl, A.; Meyer, H.H. The Formal Total Synthesis of Epothilone A. European Journal of Organic Chemistry 1999, pp. 2817–2823.

White, J.D.; Sundermann, K.F.; Carter, R.G. Improved Synthesis of Epothlione B Employing Alkylation of an Alkyne for Assembly of Subunits. Organic Letters 1999, vol. 1, pp. 1431–1434.

(Continued)

*Primary Examiner*—Fiona T. Powers
(74) *Attorney, Agent, or Firm*—Timothy J. Martin; Michael R. Henson; Rebecca A. Gegick

(57) ABSTRACT

The present invention relates to methods for use in producing epothilones and analogs and derivatives thereof. A general method according to the present invention broadly comprises performing an aldol condensation of a first compound with a second compound thereby to form a third compound selected from the formulas:

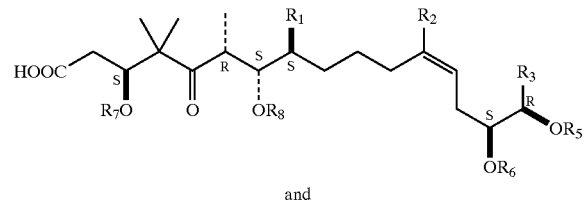

and

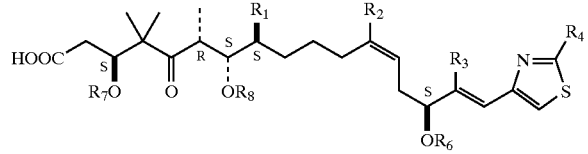

and stereoisomers thereof, and performing a macrolactonization of the third compound. The present invention also provides chemical compounds, and methods for producing such chemical compounds, that are useful in producing epothilones and analogs and derivatives thereof.

64 Claims, 25 Drawing Sheets

OTHER PUBLICATIONS

Schinzer, D.; Bauer, A.; Schieber, J. Synthesis of (−)–Epothilone B. Chemistry—A European Journal 1999, vol. 5, pp. 2492–2500.

Nicolaou, K.C.; Hepworth, D.; Finlay, M.R.V.; Paul King, N.; Werschkun, B.; Bigot, A. Synthesis of 16–Desmethyl-epothilone B: Improved Methodology for Rapid, Highly Selective and Convergent Construction of Epothilone Bepothilone B and and Analogs. Chemical Communications (Cambridge) 1999, pp. 519–520.

Taylor, R.E.; Galvin, G.M.; Hilfiker, K.A.; Chen, Y. A Formal Synthesis of Epothilone A: Enantioselective Preparation of the C1–C6 and C7–C12 Fragments. Journal of Organic Chemistry 1998, vol. 63, pp. 9580–9583.

Balog, A.; Harris, C.; Savin, K.; Zhang, X.–G.; Chou, T.C.; Danishefsky, S.J. A Novel Aldol Condensation with 2–Methyl–4–Pentenal and its Application to an Improved Total Synthesis of Epothilone B. Angewandte Chemie, International Edition 1998, vol. 37, pp. 2675–2678.

Nicolaou, K.C.; Roschangar, F.; Vourloumis, D. Chemical Biology of Epothilones. Angewandte Chemie, International Edition 1998, vol. 37, pp. 2014–2045.

Schinzer, D.; Bauer, A.; Schieber, J. Synthesis of Epothilones, Stereoselective Routes to Epothilone B. Synlett 1998, pp. 861–864.

May, S.A.; Greico, P.A. Total Synthesis of (−)–Epothilone B. Chemical Communications (Cambridge) 1998, pp. 1597–1598.

Nicolaou, K.C.; Finlay, M.R.V.; Ninkovic, S.; Sarabia, F. Total Synthesis of 26–Hydroxy–Epothilone B and Related Analogs via a Macrolactonization Based Strategy. Tetrahedron 1998, vol. 54, pp. 7127–7166.

Nicolaou, K.C.; He, Y.; Roschangar, F.; King, N.P.; Vourloumis, D.; Li, T. Total Synthesis of Epothilone E and Analogs with Modified Side Chains Through the Stille Coupling Reaction. Angewandte Chemie, International Edition 1998, vol. 37, pp. 84–87.

Nicolaou, K.C.; Sarabia, F.; Ninkovic, S.; Finlay, M.R.; Boddy, C.N.C. Probing the Ring Size of Epothilones: Total Synthesis of [14]–, [15]–, [17]–, and [18] Epothilones A. Angewandte Chemie, International Edition 1998, vol. 37, pp. 81–84.

Nicolaou, K.C.; Sarabia, F.; Finlay, M.R.V.; Ninkovic, S.; King, N.P.; Vourloumis, D.; He, Y. Total Synthesis of Ozazole– and Cyclopropane–Containing Epothilone B Analogs by the Macrolactonization Approach. Chemistry—A European Journal 1997, vol. 3, pp. 1971–1986.

Nicolaou, K.C.; Vallberg, H.; King, N.P.; Roschangar, F.; He, Y.; Vourloumis, D.; Nicolaou, C.G. Total Synthesis of Oxozole– and Cyclopropane–Containing Epothilone A Analogs by the Olefin Metathesis Approach. Chemistry—A European Journal 1997, vol. 3, pp. 1957–1970.

Nicolaou, K.C.; Ninkovic, S.; Finlay, M.R.V.; Sarabia, F.; Li, T. Total Synthesis of 26–Hydroxyepothilone B and Related Analogs, Chemical Communications (Cambridge) 1997, pp. 2343–2344.

Meng, D.; Bertinato, P.; Balog, A.; Su, D.–S.; Kamenecka, T.; Sorensen, E.; Danishefsky, S.J. Total Synthesis of Epothilones A and B. Journal of the American Chemical Society 1997, vol. 119, pp. 10073–10092.

Nicolaou, K.C.; Ninkovic, S.; Sarabia, F.; Vourloumis, D.; He, Y.; Vallberg, H.; Finlay, M.R.V.; Yang, Z. Total Synthesis of Epothilones A and B via a Macrolactonization–Based Strategy, Journal of the American Chemical Society 1997, vol. 119, pp. 7974–7991.

Balog, A.; Meng, D.; Kamenecka, T.; Bertinato, P.; Su, D.–S.; Sorensen, E.J.; Danishefsky, S.J. Total Synthesis of (−)–Epothilone A. Angewandte Chemie, International Edition in English, 1996, vol. 35, pp. 2801–2803.

Yang, X.; He, Y.; Vourloumis, D.; Vallberg, H.; Nicolaou, K.C. Total Synthesis of Epothilone A: The Olefin Metathesis Approach. Angewandte Chemie, International Edition in English 1997, vol. 36, pp. 166–168.

Schinzer, D.; Limberg A.; Bauer, A.; Boehm, O.M.; Cordes, M. Totally Synthesis of (−)–Epothilone A. Angewandte Chemie, International Edition in English 1997, vol. 36, pp. 523–524.

Nicolaou, K.C.; Sarabia, F.; Ninkovic, S.; Yang, Z. Total Synthesis of Epothilone A: The Macrolactonization Approach. Angewandte Chemie, International Edition in English 1997, vol. 36, pp. 525–527.

Su, D.–S.; Mend, D.; Bertinato, P.; Balog, A.; Sorensen, E.J.; Danishefsky, S.J.; Zheng, Y.–H.; Chou, T.–C.; He, L.; Horwitz, S.B. Total Synthesis of (−)–Epothilone B: An Extension of the Suzuki Coupling Method and Insights into Structure–Activity Relationships of the Epothilones. Angewandte Chemie, International Edition in English 1997, vol. 36, pp. 757–759.

Appendino, G.; Casiraghi, G. The Synthesis of Epothilones: Highlights from a Year's Race. Chemtracts—Organic Chemistry 1998, vol. 11, pp. 678–696.

Bijoy, P.; Avery, M.A. Synthetic Studies Directed Towards Epothilone A: Enantioselective Synthesis of a C7–C15 Carboxaldehyde Segment. Tetrahedron Letters 1998, vol. 39, pp. 209–212.

Brabander, J.D.; Rosset, S.; Bernardelli, G. Towards a Synthesis of Epothilone A: Rapid Assembly of the C1–C6 and C7–C12 Fragments. Synlett 1997, pp. 824–826.

Casadei, M.A.; Galli, C.; Mandolini, L.; Ring–Closure Reations. 22. Kinetics of Cyclization of Diethyl (w–Bromoalkyl) Malonates in the Range of 4– to 21– Membered Rings Role of Ring Strain Journal of American Chemical Society 1984, vol. 106, pp. 1051–1056.

Morikawa, K.; Park, J.; Andersson, P.G.; Hashiyama, T.; Sharpless, K.B. Catalytic Asymmetric Dihyroxylation of Tetrasubstituted Olefins. Journal of American Chemical Society 1993, vol. 115, pp. 8463–8464.

Bollag, D.M.; McQueney, P.A.; Zhu, J.; Hensens, O.; Koupal, L.; Liesch, J.; Goetz, M.; Lazarides, E.; Woods, C.M. Epothiones, A New Class of Microtubule–Stabilizing Agents with a Taxol–Like Mechanism of Action. Chemtracts–Organic Chemistry 1998. vol. 11. pp. 671–677.

Ojima, F.; Habus, I.; Zhao, M.; Zucco, M.; Park, Y.H.; Sun, C.M.; Brigaud, T. New and Efficient Approaches to the SemiSynthesis of Taxol and its C–13 Side Chain Analogs by Means of B–Lactum Synthon Method. Tetrahedron 1992, vol. 48, pp. 6985–7012.

Chandrasekhar, S.; Mohanty, P.K.; Takhi, M. Practical One–Pot Di–O–Silylaton and Regioselective Deprotective Oxidation of 1–O–Silyl Ether in 1.2–Diols. Journal of Organic Chemistry 1997. vol. 62, pp. 2628–2629.

Trehan, I.R.; Singh, J.; Arora, A.K.; Kaur, J.; Kad, G.L. Synthesis of Undecan–3–One; (+–) Frontalin; (+–)–Endo–, and (+–)–Exo– Brevicomin Under Sonochemical Aqueous Conditions. Indian Journal of Chemistry 1995, vol. 34B, pp. 396–398.

Kumar, G.N.; Walle, U.K.; Wallet, T. Cytochrome P450 3A–Mediated Human Liver Microsomal Taxol 6a–Hydroxlation. The Journal of Pharacology and Experimental Therapeutics 1994, vol. 268, pp. 1160–1165.

Schroder, M. Osmium Tetraoxide Cis Hydroxylation of Unsaturated Substrates. Chemical Review 1980, vol. 80, pp. 187–213.

Hasehm, M.A.; Jung, A.; Ries, M.; Kirschning, A. Erratta and Addenda 1998, p. 195.

DeBrabander, J.; Rosset, S.; Bernadinelli, G. Erratta and Addenda 1997, p. 824.

Mulzer, J.; Mantoulidis, A.; Ohler, E. Total Synthesis of Epothilones B and D. Journal of Organic Chemistry 2000. vol. 65, pp. 7456–7467.

Borzilleri, R.M.; Zheng, X.; Schmidt, R.J.; Johnson, J.A.; Kim, S.-H.; DiMarco, J.D.; Fairchild, C.R.; Gougoutas, J.Z.; Lee, F.Y.F.; Long, B.H.; Vite, G.D. A Novel Application of a Pd(0)– Catalyzed Nuclephilic Substitution Reaction to the Regio– and Stereoselective Synthesis of Lactam Analogues of the Epothilone Natural Products. Journal of the American Chemical Society 2000, vol. 122. pp. 8890–8897.

Andersson, P.G.; Sharpless, K.B. A Dramatic Ligand Effect on the Relative Reactivities of Substituted Alkenes with Osmium Tetroxide. Journal of the American Chemical Society 1993, vol. 115, pp. 7047–7048.

Nicolaou, K.C.; Winssinger, N.; Pastor, J.; Ninkovic, S.; Sarabia, F.; He, Y.; Vourloumis, D.; Yang, Z.; Li, T.; Giannakakou, P.; Hamel, E. Synthesis of Epothilones A and B in Solid and Solution Phase. Nature, vol. 387, May 15, 1997, pp. 268–272.

Mulzer, J.; Karig, G., Pujarliev, P. A Novel Highly Stereoselective Total Synthesis of Epothilone B and of its (12R, 13R) Acetonide. Tetrahedron Letters 2000, vol. 41, pp. 7635–7638.

Mulzer, J. Epothilone B and Its Derivatives as Novel Antitumor Drugs: Total and Partial Synthesis and Biological Evaluation. Monatshefte fur Chemie 2000, vol. 131, pp. 205–238.

Nicolaou, K.C.; Hepworth, D.; King, N.P.; Finlay, M.R.V.; Scarpelli, R.; Manuela, M.; Pereira, A.; Bollbuck, B.; Bigot, A.; Werschkun, B.; Winssinger, N. Total Synthesis of 16–Desmethylepothilone B, Epothilone B10, Epothilone F, and Related Side Chian Modified Epothilone B Analogues. European Chemical Journal 2000, vol. 6, pp. 2783–2800.

Key: a) n-BuLi, Ether; Et₂AlCl, toluene; b) 5 then dil.HCl; c) Lindelar Catalyst, H₂; d) TsCl, THF, pyridine; e) TMStriflate, CH₂Cl₂, 2,6-Lutidine; f) NaI, acetone, Δ; g) N-Propionylcamphorsultam 18, n-BuLi, then 17; h) DIBAH, THF-CH₂Cl₂.

Key: a) MEMCl, DIPA, CH2Cl2; b) TBAF, THF; c) Swern Oxidation; d) Horner-Emmons Reaction, LDA, THF, 24; then ketone 23; e) HCl, H2O, THF; f) TsCl, pyridine, CH2Cl2; g) TBSOTf, DIPA; h) NaI, acetone, Δ; i) N-propionylcamphorsultam 18, n-BuLi, then iodide; j) DIBAH, CH2Cl2.

Key: a) Cl$_3$C$_6$H$_2$COCl, pyridine, DMAP; b) TBAF, THF; c) PCC, CH$_2$Cl$_2$; d) Horner-Emmons: LDA, 24.

Key: a) 58, TBAF, THF; 58a, chromatography; 58b, dil. acid or DDQ, CH2Cl2, water; b) PhSO2Cl, pyridine, or Cl3PhCOCl, pyridine, DMAP, CH2Cl2.

Key: a) as in Figure 7

Key: a) 1.0 TBAF, THF; b) PCC, CH$_2$Cl$_2$; c) pyridine or DMAP, CH$_2$Cl$_2$; d) Horner-Emmons: LDA, 24 or other phosphonates.

Key: a] i)Mg, ether; ii) CuBr•DMS; iii) propyne; iv) I$_2$; b] i) n-BuLi; ii) Me$_2$AlCl; iii) 5b; c) HCl, EtOH; d) TsCl, pyridine; e) TBSOTf, 2,6-lutidine, CH$_2$Cl$_2$; f) NaI, acetone; g) 18, n-BuLi, -40 °C, THF; h) LiAlH$_4$, THF; d) pyridine•SO$_3$, CH$_2$Cl$_2$; Et$_3$N.

Key: a] i) Mg, ether; ii) CuBr·DMS, DMS, ether; iii) propyne; iv) pentynyl lithium; b) 5b, -40 °C, 36 hrs; c) TBSOTf, 2,6-lutidine, CH2Cl2; d) AD-mix a, e) NaIO4, EtOH, HOH; f) NaBH4, MeOH; g) TsCl, pyridine.

Key: a) NaI, acetone; b) 18, n-BuLi, -40 _C, THF; c) LiAlH4, THF; d) pyridine·SO3, CH2Cl2; Et3N; e) DIBAH, ether, -78 °C.

Key: a) PCC, CH$_2$Cl$_2$; b) pyridine or DMAP, CH$_2$Cl$_2$; c) Horner-Emmons: LDA, 24 or other phosphonates.

Key: a) O$_3$, MeOH, -78 °C; then NaBH$_4$; b) TsCl, pyridine; c) LiBr, acetone; d] i) Mg, ether; ii) CuBr·DMS, DMS, ether; iii) propyne; iv) pentynyl lithium; v) 5a or 5b, -40 °C, 36 hrs; e) TMSOTf, 2,6-lutidine, CH$_2$Cl$_2$; or p-MeOC$_6$H$_4$CH$_2$Br, NaH, DMF; f) ADmix a; then NaIO$_4$.

Key: a] i) Mg, ether; ii) CuBr·DMS, DMS, ether; iii) propyne; iv) pentynyl lithium; v) 5a, -40 °C, 36 hrs; b] i) Mg, ether; ii) CuBr·DMS, DMS, ether; iii) propyne; iv) pentynyl lithium; v) 5a, -40 _C, 36 hrs; vi) TMSOTf, -78 °C; c) TMSOTf, 2,6-lutidine, CH$_2$Cl$_2$; d) (ipc)2BH, THF, -20 °C; then H$_2$O$_2$, NaOH; e) pyr·SO$_3$, DMSO, Et$_3$N, CH$_2$Cl$_2$; f) (ipc)2BH, THF, -20 °C; then PCC, CH$_2$Cl$_2$.

Key: a) PBr₃; b) Mg, ether; then propyne, Cu(I); pentynyl lithium; then epoxide 4; then TBSCl; c) DDQ; d) Jones Oxidation; e) Swern Oxidation; f) Horner-Emmons reaction with 7; g) (Ipc)₂BH, THF; then PCC; h) (Ipc)₂BH, THF; then HOONa; i) Pyridine•SO₃, Et₃N, CH₂Cl₂; j) slight excess LDA, THF, -40 °C; k) TBSOTf, 2,6-lutidine, CH₂Cl₂; l) PhSO₂Cl, pyridine; m) Cl₃C₆H₂COCl, pyridine, DMAP; n) TBAF, THF; o) Dimethyldioxirane, acetone.

FIG. 23

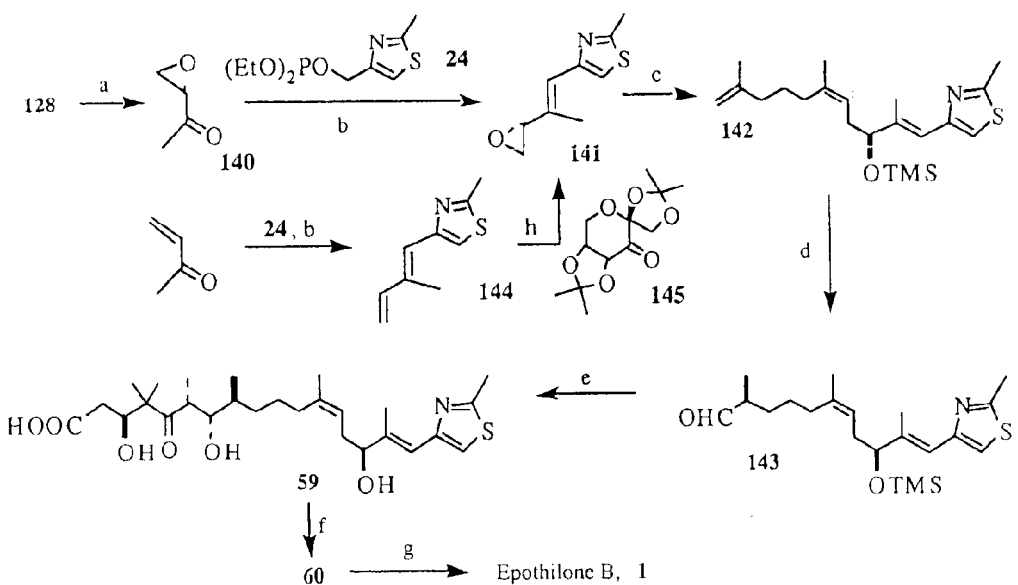

Key: a) Cr(VI), or pyridine•SO3, DMSO, Et3N, CH2Cl2; b) LDA, 24, then 140; c] i) 123, Mg, ether; ii) CuBr•DMS, DMS, ether; iii) propyne; iv) pentynyl lithium; v) 141, -40 °C, 36 hrs; vi) TMSOTf, -78 °C; d) (ipc)2BH; then Cr(VI); e) 56a, THF, -78 °C; then silica gel; f) PhSO2Cl, pyridine, CH2Cl2; g) dimethyldioxirane, acetone; h) chiral ketone 145, oxone, pH 7-8, aq. CH3CN (Y. Shi, et al., J. Org. Chem., 63(23), 8475 (1998).).

FIG. 24

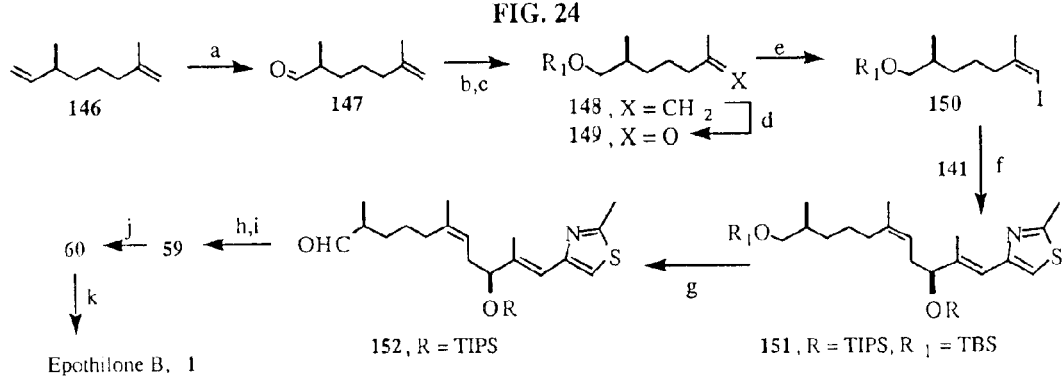

Key: a) AD-mix; then NaIO4; b) NaBH4, MeOH; c) TBSCl, pyridine, CH2Cl2; d) O3, CH2Cl2; Me2S; e) Ph3P=CH-I, THF; f) t-BuLi, then Et2AlCl, then 141, then TIPSCl; g) Quinolinium fluorochromate, CH2Cl2; h) 56a, THF, -78 °C; i) HF•pyr, CH3CN; j) PhSO2Cl, pyridine, CH2Cl2; k) dimethyldioxirane, acetone.

Key: a) Zn/Cu, sonochem; b) Ph$_3$P=CH-I, THF; c) (Ipc)$_2$BH; then NaBO$_3$; d) TBSCl, pyr, CH$_2$Cl$_2$.

FIG. 26b

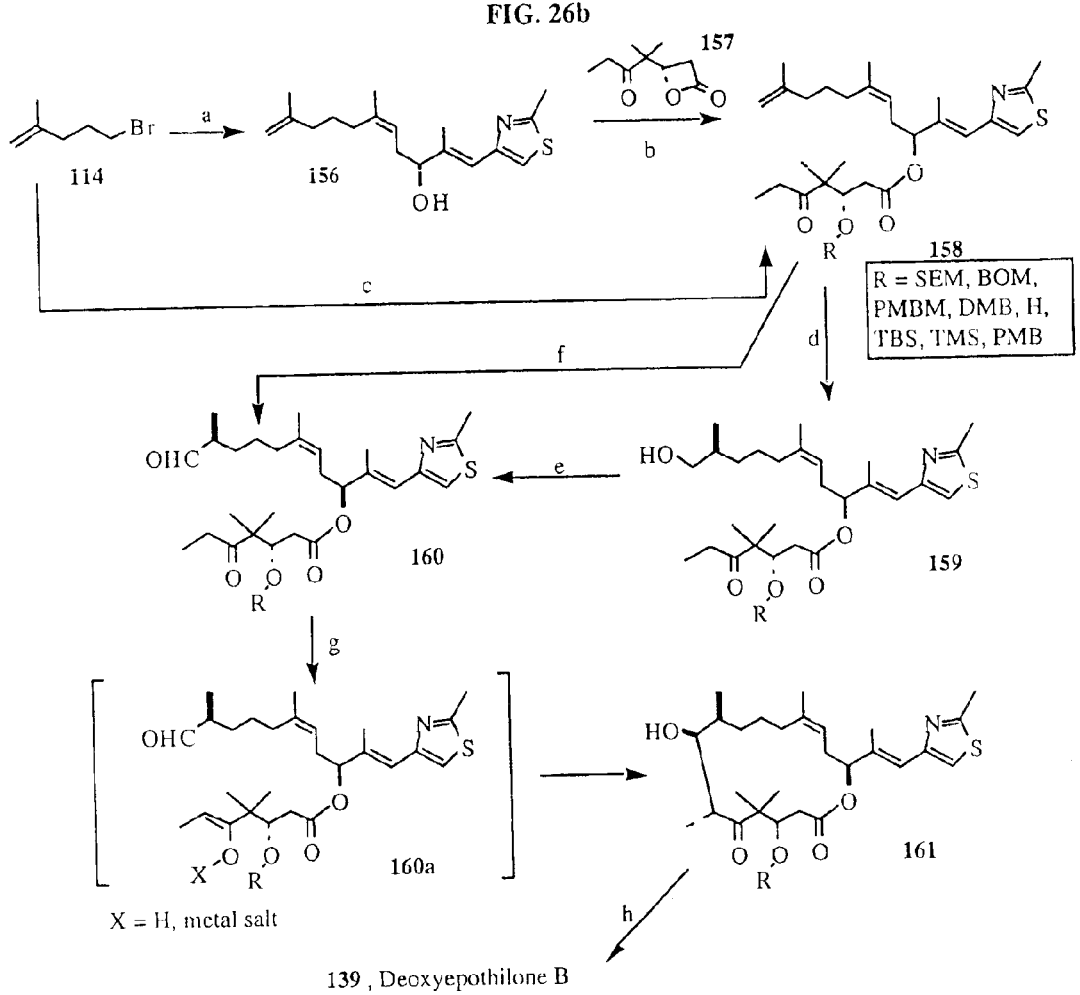

Key: a) Mg, ether; then propyne, Cu(I); pentynyl lithium; epoxide 143 (Scheme XXIII); then H3O+; b) β-lactone 157 (Scheme XXIII), pyridine, CH2Cl2; c) Mg, ether; then propyne, Cu(I); pentynyl lithium; β-lactone 157 (Scheme XXIII); then p-MeOC6H4CH2OCH2Cl or other protecting group such as TBSOTf or TBSCl; d) (Ipc)2BH, THF; then LiOOH; e) Swern Oxidation; f) (Ipc)2BH, THF; then PCC; g) Lewis or protic acid; or alternatively base catalyzed cyclization; h) DDQ, CH2Cl2, HOH, buffer to remove the PMB, PMBM or DMB groups; Fluoride ion to remove Si based groups.

Key: a) RCOX, pyridine, catalytic DMAP, CH$_2$Cl$_2$; b) TMSOTf, 2,6-lutidine, CH$_2$Cl$_2$; c) R1COX, DMAP, CH$_2$Cl$_2$; d) R1COX, DMAP, CH$_2$Cl$_2$; then silica gel. Where RCOX = active ester of usual variety.

FIG. 29

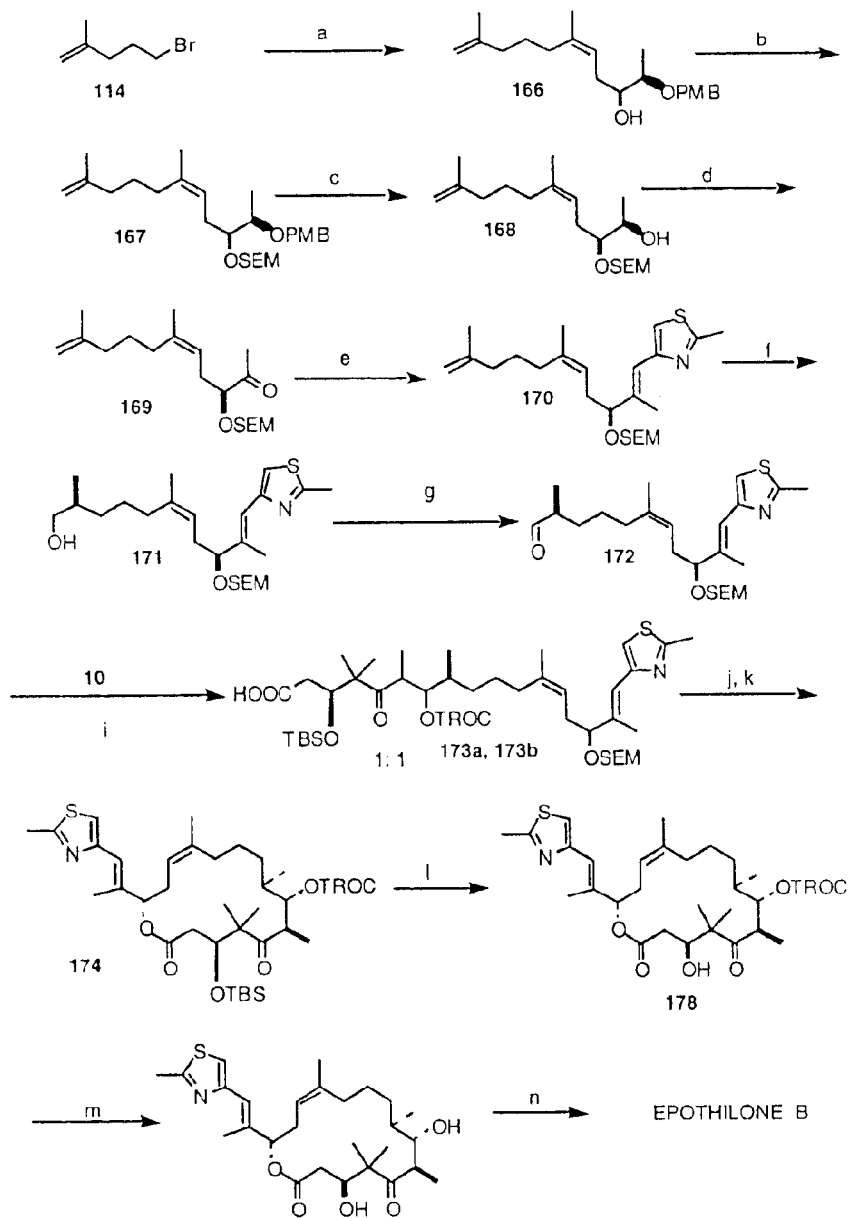

Key: a) i. Mg, ether; ii. CuBr·DMS complex, ether, DMS, -45°C; iii. propyne, -23°C; iv. Li-hexyne, HMPA, -78°C; v. 5c, -78°C to -25°C, 78%; b) SEM-Cl, DIPEA, CH$_2$Cl$_2$, 94%; c) DDQ, CH$_2$Cl$_2$, HOH, 85%; d) SO$_3$·pyr, TEA, CH$_2$Cl$_2$; 78%; e) 24, n-BuLi, THF, -78°C to R.T., 85%; f) (Ipc)$_2$BH, THF; H$_2$O$_2$, 82%; g) oxalyl chloride, DMSO, TEA, CH$_2$Cl$_2$, 88%; h) LDA, -78°C to -40°C, ZnCl$_2$; -78°C to -50°C, THF, 68%; i) TROC-Cl, DMAP, CH$_2$Cl$_2$, j) TFA, CH$_2$Cl$_2$, k) Trichlorobenzoyl chloride, TEA, THF, DMAP, toluene; l) HF·pyridine; m) Zn, HOAc; n) m-CPBA, CH$_2$Cl$_2$.

Key: a) HF·pyridine, THF; b) Zn, HOAc; c) RCOOH, DCC, TEA, DCM.

Key: a) LDA, -78°C to -40°C, ZnCl₂; -78°C to -50°C, THF, 68%; then CH₂=CH(CH₂)₃COCl, DMAP, CH₂Cl₂, b) TFA, CH₂Cl₂, c) Trichlorobenzoyl chloride, TEA, THF, DMAP, toluene; d) HF•pyridine; e) vicinal dihydroxylation; f) NaIO₄, THF, HOH.

Key: a) PMB-Br, NaH, Bu$_4$N-I, THF, 0 °C, 85%; b) i) Mg, ether, rt; ii) CuBr-DMS, ether, DMS, -45°C, 3h, iii) Propyne, -45 °C to -23 °C, 4h then lithiohexyne, -78°C, 1h; iv) epoxide 205, -78 °C, 1h, -25 °C, 24h, 76%; c) SEMCl, DIPEA, DCM, 0°C, 92%; d) DDQ, DCM:water (8:2), 88%; e) DMSO, (COCl)$_2$, DCM, TEA, -78 °C, 85%; f) 207, n-BuLi, THF, then 214, 72%; g) (i-PC)$_2$BH, THF, 0.5h, aq. NaBO$_3$; and h) DMSO, (COCl)$_2$, DCM, TEA, -78 °C, 92%.

Key: (a) (i) Bu₂BOTf, DIPEA, CH₂Cl₂, 0 °C then add 217 at -78 °C; (ii) Raney Ni, acetone, 60 °C, 45 min, 70% combined; (b) (i) TBDMSOTf, 2,6-lutidine, CH₂Cl₂, 0 °C to rt, 95%; (ii) LiOH, H₂O₂, THF-H₂O, rt, 82%.

Key: a) LDA, 204, THF, -78 °C to -40 °C then to -78 °C, ZnCl₂, 203, -78 °C to -50 °C, 0.5h; b) TrocCl, Py, DCM, 0 °C; c) TFA, DCM (3:7), -20 °C, 1h, 63% (three steps).

Key: (a) 2,4,6-Cl$_3$C$_6$H$_2$COCl, TEA, THF, DMAP, toluene, rt, 1h; b) HF-Py, DCM, rt, 95%;
c) Zn, aq. NH$_4$Cl, MeOH, reflux, 92%; d) [Methyl(trifluoromethyl)]dioxirane, MeCN, 0 °C, 56%.

SYNTHESIS OF EPOTHILONES AND RELATED ANALOGS

CROSS-REFERENCE TO RELATED APPLICATIONS

This application claims the benefit of U.S. Provisional Application No. 60/240,488, filed Oct. 13, 2000.

FIELD OF THE INVENTION

The present application relates to the synthesis of chemical compounds that are useful in treating cancer. More specifically, the present application is directed to methods for synthesizing epothilone compounds and related analogs and derivatives thereof. The present application is also directed to chemical compounds, and pharmaceuticals prepared therewith, formed through the methods of the present invention.

BACKGROUND OF THE INVENTION

Two unique macrolactones were detected during mass screening for Taxol-like substances by both Merck Research Labs and the GBF (Gesellschaft fur Biotechnologische Forshung mbH, Germany). Bollag, D. M., et al., *Epothilones, a new class of microtubule-stabilizing agents with a taxol-like mechanism of action*. Cancer Res., 1995. 55(11): p. 2325–33; Bollag, D. M., *Epothilones: novel microtubule-stabilizing agents*. Expert Opin. Invest. Drugs, 1997. 6(7): p. 867–873. As a result, Epothilone B 1, and Epothilone A, 2, were both isolated from the myxobacterium *Sorangium cellulosium* and the two dimensional structures were determined by the Merck group using NMR spectroscopic methods (HMBC), and the X-ray structure was published by the GBF group. Höefle, G., et al., *Antibiotics from gliding bacteria. 77. Epothilone A and B—novel 16-membered macrolides with cytotoxic activity: isolation, crystal structure, and conformation in solution*. Chem. 1996, 108, 1671–1673; Angew. Chem., Int. Ed. Engl., 1996. 35(13/14): p. 1567–1569. Both macrolides 1 and 2 appear to possess identical modes of action to Taxol, but are thousand-fold more potent in multidrug resistant cell lines.

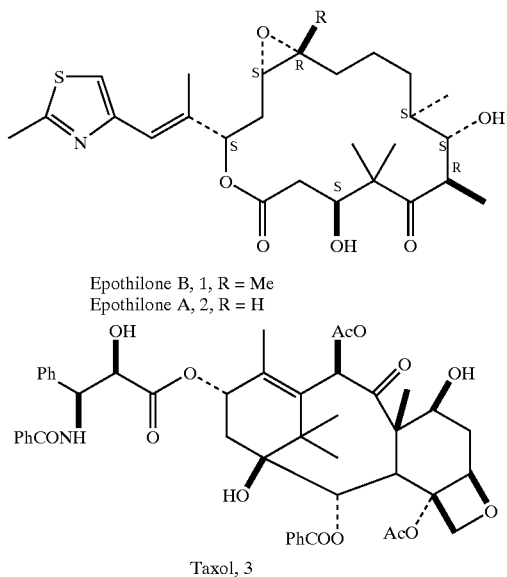

Epothilone B, 1, R = Me
Epothilone A, 2, R = H

Taxol, 3

Taxol 3 is perhaps one of the most structurally complex anticancer agents known. Since its discovery in the early 1970's, it has received great attention from the scientific and medical community. Borman, S., *Scientists Mobilize To Increase Supply of Anticancer Drug Taxol*, in Chem. & Engr. News. 1991. p. 11–18. Taxol binds to the microtubule, or polymeric, form of tubulin with micromolar $K_D$ values and stabilizes the microtubule pool by blocking the transition between G2 and M phases of cell growth. Taxol has a specific binding site in the polymeric tubulin. While other agents which arrest mitosis are known and are in clinical use for cancer chemotherapy, Taxol has elicited much attention for its efficacy against drug-refractory tumors, most notably ovarian but also metastatic breast, head and neck, melanoma and lung cancers. Taxol has recently been approved by the Food and Drug Administration for treatment of ovarian cancer (1992), breast cancer (1994) and is expected to be approved for other cancers. Riondel, J., et al., Cancer Chemother. Pharmacol., 1986. 17: p. 137. Thus, while Taxol finds clinical promise against refractory cancers, substantial problems are none the less associated with this anticancer agent. Taxol is only poorly water soluble necessitating its administration in Chremophor, a solvent that in itself can be more toxic than Taxol and has caused a number of clinical problems. Further, more serious complications include peripheral neuropathy, neutropenia, cardiac arrythmias, and less problematical, alopecia. Perhaps not surprisingly, Taxol is itself a genetic toxin at levels comparable to those in clinical use. Finally, perhaps some of the toxicity issues are related to the short plasma half-life of Taxol (less than 5 hrs). Kumar, G., T. Walle, and U. Walle, *Cytochrome P450 3A-Mediated Human Liver Microsomal Taxol 6a-Hydroxylation*. J. Pharmacol. Exp. Ther., 1994. 268; p. 1160–1165.

The most interesting feature of Epothilone B is that it behaves essentially identically to Taxol 3 in vitro, yet is thousand-fold more active than Taxol in cancerous cells which have acquired multiple drug resistance (MDe), has the advantage of better solubility than taxol, and can be obtained in multigram quantities. Bollag, D. M., et al., *Epothilones, a new class of microtubule-stabilizing agents with a taxol-like mechanism of action*. Cancer Res., 1995. 55(11): p. 2325–33; Bollag, D. M., *Epothilones: novel microtubule-stabilizing agents*. Expert Opin. Invest. Drugs, 1997. 6(7): p. 867–873; Buck, S. B., et al., *Epothilones, a new class of microtubule-stabilizing agents with a taxol-like mechanism of action*. Chemtracts, 1998. 11(9): p. 671–677; Grever, M. R.; Schepartz, S. A.; Chabner, B. A. *Seminars in Oncology* 1992, 19, 622–638. In P-glycoprotein (the MDR protein which pumps drugs out of the cell) expressing KBV-1 cells, for example, $IC_{50}$ values for Taxol are $2.3 \times 10^{-5}$ M but are $5.8 \times 10^{-8}$ M for Epothilone B. These effects seem to be expressed on a mechanistic level; Epothilone B binds competitively with Taxol to the Taxol binding site but is presumably a much poorer P-glycoprotein substrate. Since the most remarkable feature of Taxol is its good activity against MDR cancers, and Epothilone B is far superior to Taxol in this regard, it is likely that Epothilone B will evolve to have a much greater therapeutic index than Taxol against MDR cancers. At the very least, Epothilone B (analogs) would be a useful next line of clinical chemotherapy once Taxol resistance had been encountered. While much more research remains to be done for the epothilones, it still seems as if Epothilone B could well become an anticancer drug that is clinically far superior to Taxol.

Epothilone B has one main ring, a 16-membered lactone ring with a total of 7 stereocenters. In comparison, Taxol has four main rings and 11 stereocenters and has occupied the best minds in synthetic organic chemistry for at least the last ten years with no less than 30 groups working on its total synthesis at one time or the other over this period of time. While its total synthesis was completed by Holton, Danishevsky and Nicolaou (Holton, R. A., et al., *First Total Synthesis of Taxol. 1. Functionalization of the B Ring*. J. Amer. Chem. Soc., 1994. 116: p. 1597–1598), the incredible complexity of Taxol has hampered the development of a viable total synthetic route by which Taxol or its analogs could be obtained for clinical use. However, the supply issue for Taxol was solved to some extent by partial synthesis from baccatins, available from ornamental yew plants. Ojima, I., et al., *New and Efficient Approaches to the Semisynthesis of Taxol and Its C-13 Side Chain Analogs by Means of β-Lactam Synthon Method*. Tetrahedron, 1992. 48: p. 6985–7012.

The synthesis of Epothilone B, on the other hand, should not represent an insurmountable task. Epothilone B has yet to receive the attention that Taxol has, but is in principle inexhaustibly available from fermentation. However, practical experience has led the Merck group to abandon the preparation of Epothilones by fermentation due to extremely poor yields, a finding confirmed by NaPro Biotherapeutics. Thus, in order to obtain Epothilone B for clinical trials, semi-synthetic modification, structure-activity relationship studies, and to make it commercially available, an efficient total synthesis is required.

Several excellent syntheses of Epothilone A and B have appeared in the last few years, as reported in Appendino, G. and G. Casiraghi, *The synthesis of epothilones: highlights from a year's race*. Chemtracts, 1998. 11(9): p. 678–696. Numerous reported syntheses and partial syntheses, as well as patent-related publications have also appeared in the past few years in regards to Epothilone syntheses: Nicolaou, K. C.; Roschangar, F.; Vourloumis, D. *Angew. Chem.* 1998, 110, 2121–2153; *Angew. Chem. Int. Ed. Engl.* 1998, 37, 2014–2045; Mulzer, J. *Chem. Mon.* 2000, 131, 205–238; Meng, D.; Bertinato, P.; Balog, A.; Su, D.-S.; Kamenecka, T.; Sorensen, E.; Danishefsky, S. J. *J. Am. Chem. Soc.* 1997, 119, 100073–10092; Nicolaou, K. C.; He. Y.; Vourloumis, D.; Vallberg, H.; Roschanger, F.; Sarabia, F.; Ninkovic, S.; Yang, Z.; Trujillo, J. I. *J. Am. Chem. Soc.* 1997, 119, 7960–7973; Nicolaou, K. C.; Ninkovic, S.; Sarabia, F.; Vourloumis, D.; He. Y.; Vallberg, H.; Finlay, M. R. V.; Yang, Z. *J. Am. Chem. Soc.* 1997, 119, 7974–7991; Schinzer, D.; Limberg, A.; Bauer, A.; Boehm, O. M.; Cordes, M. *Angew. Chem. Int. Ed. Engl.* 1997, 36, 523–524; May, S. A.; Grieco, P. A. *Chem. Commun.* 1998, 1597–1598; White, J. D.; Carter, R. G.; Sundermann, K. F.; Wartmann, M. *J. Am. Chem. Soc.* 2001, 123, 5407–5413; Martin, H. J.; Drescher, M.; Mulzer, J. *Angew. Chem. Int. Ed. Engl.* 2000, 39, 581–583; Sawada, D.; Shibasaki, M. *Angew. Chem. Int. Ed. Engl.* 2000, 39, 209–213; Mulzer, J.; Mantoulidis, A.; Öhler, E. *J. Org. Chem.* 2000, 65, 7456–7467; Panicker, B.; Karle, J. M.; Avery, M. A. *Tetrahedron*, 2000, 56,7859–7868 and references therein;

Vite, G. D., et al., *syntheses of epothilone derivatives and intermediates for use in treatment of hyperproliferative cellular disease*, 1999: PCT Int. Appl.;

Vite, G. D., et al., *Epothilone derivatives*, 1999: PCT Int. Appl.;

Klar, U., et al., New method for the preparation of the C(1)–C(6)-segment of epothilone and epothilone derivatives, 1999: Ger. Offen.;

Klar, U., et al., New (C13–C15)-fragments, method for their preparation and their application for synthesis of epothilone and epothilone derivatives, 1999: Ger. Offen.;

Klar, U., et al., New (C1–C6)-fragments, method for their preparation and their application for synthesis of epothilone and epothilone derivatives, 1999: Ger. Offen.;

Klar, U., et al., Preparation of new epothilone derivatives as pharmaceutical agents, 1999: PCT Int. Appl.;

Kim, S. H. and R. M. Borzilleri, A process for the preparation of ring-opened epothilone intermediates which are useful for the preparation of epothilone analogs, 1999: PCT Int. Appl.;

Kim, S. H. and J. A. Johnson, A process for the reduction of oxiranyl epothilones to olefinic epothilones, 1999: PCT Int. Appl.;

Wessjohann, L. A. and T. Gabriel, Preparation of epothilone synthon, 1998: Ger. Offen.;

Bosslet, K., et al., Glycoconjugates of antitumor drugs with improved in vivo compatibility, 1998: Ger. Offen.;

Methods for preparation of epothilone derivatives, 1998: Ger. Offen.;

Schinzer, D., et al, Method for producing epothilones and the intermediate products obtained during the production process, 1998: PCT Int. Appl.;

Schinzer, D., A. Limberg, and O. M. Boehm, Intermediate products within the total synthesis of Epothilones A and B, 1997: Ger.;

Danishefsky, S. J., et al., Synthesis of epothilones, intermediates and analogs for use in treatment of cancers with multidrug-resistant phenotype, 1999: PCT Int. Appl.;

Rosen, N., et al., A method of treating cancer using an antineoplastic agent-prenyl-protein transferase inhibitor combination, and compound preparation, 1998: PCT Int. Appl.;

Hunter, W. L., Antimicrotubule compositions and methods for treating or preventing inflammatory diseases, 1998: PCT Int. Appl.;

Höfle, G. and M. Sefkow, Procedure for the preparation of epothilones with a modified side chain, 1998: PCT Int. Appl.;

Danishefsky, S. J., et al., Synthesis of epothilones, intermediates thereto, analogs and uses thereof, 1999: PCT Int. Appl.;

Reichenbach, H., et al., Epothilone C, D, E and F, production process, and their use as cytostatics well as phytosanitary agents, 1998: PCT Int. Appl.;

Höfle, G. and M. Kiffe, Preparation of epothilone derivatives as agrochemicals and pharmaceuticals, 1997: PCT Int. Appl.;

Höfle, G., et al., 1993: (GBF), DE;

Nicolaou, C. K., et al., Preparation of epothilone analogs as anticancer agents, 1998: PCT Int. Appl.;

Hofle, G. and M. Sefkow, Procedure for the preparation of epothilones with a modified side chain, 1998: PCT Int. Appl.;

Hofle, G. and M. Kiffe, Preparation of epothilone derivatives as agrochemicals and pharmaceuticals, 1997: PCT Int. Appl.;

Hoefle, G. and M. Kiffe, Preparation of epothilone derivatives as agrochemicals and pharmaceuticals, 1997: Ger. Offen.;

Hoefle, G., et al., Epothilone derivatives, 1993: Ger. Offen.;

Mulzer, J. and A. Mantoulidis, Method for the production and use of thiazole derivatives, 1999: PCT Int. Appl.;

Mulzer, J. and A. Mantoulidis, Method for the preparation and assembly of intermediate products in the production of epothilones, 1998: Ger. Offen., and May, S. A., Total synthesis of complex natural products: i. endiandric acid a. ii. (+/−)-adrenosterone. iii. (−)-epothilone b, 1998. p. 172.

However, there still remains a need for approaches that will provide an efficient route to Epothilone A, B or Deoxyepothilone A or B, or to analogs and derivatives of these compounds.

SUMMARY OF THE INVENTION

According to the present invention then, a new and useful method is provided for use in producing epothilones and analogs and derivatives thereof. The method comprises performing an aldol condensation of a first compound selected from the formulas:

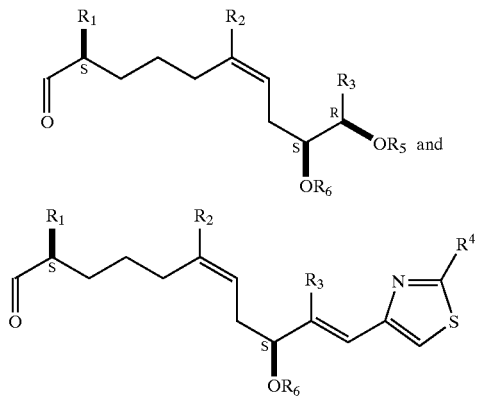

and stereoisomers thereof, with a second compound selected from the formulas:

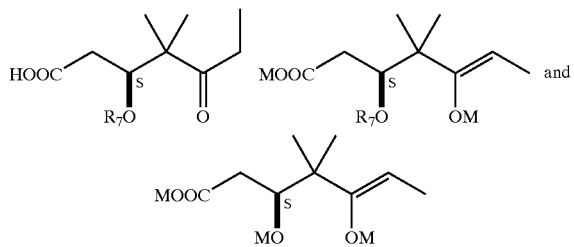

and stereoisomers thereof, thereby to form a third compound selected from the formulas:

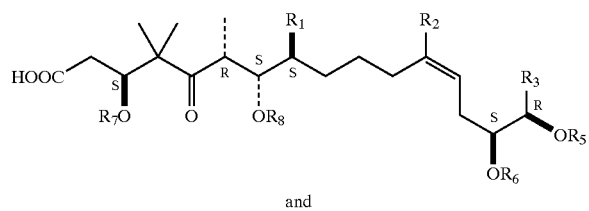

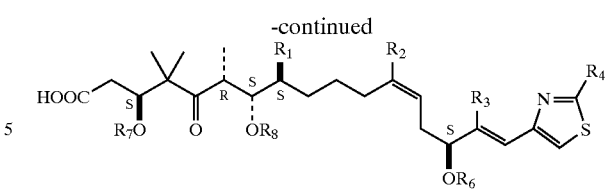

and stereoisomers thereof, wherein $R_1$, $R_2$, $R_3$ and $R_4$ are each selected from H, alkyl, alkenyl, alkynyl, aryl, substituted alkyl, substituted aryl, cycloalkyl and heterocyclo; wherein $R_5$, $R_6$, $R_7$ and $R_8$ are each selected from H and a protecting group; and wherein M is an alkali metal; and performing a macrolactonization of the third compound thereby to form a fourth compound selected from the formulas:

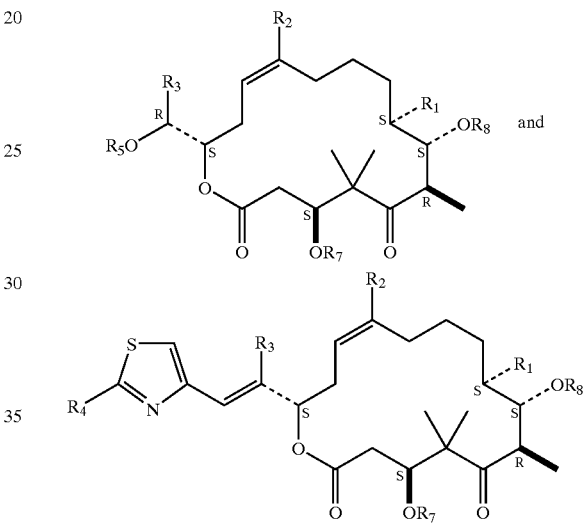

and stereoisomers thereof, wherein $R_1$, $R_2$, $R_3$ and $R_4$ are each selected from H, alkyl, alkenyl, alkynyl, aryl, substituted alkyl, substituted aryl, cycloalkyl and heterocyclo; and wherein $R_5$, $R_7$ and $R_8$ are each selected from H and a protecting group. $R_1$, $R_3$ and $R_4$ may each be methyl when $R_2$ is H or methyl, and at least one of $R_5$–$R_8$ may be TBS. More broadly, $R_5$ may be selected from PMB, DPS and TBS; $R_6$ may be selected from H, TBS, TMS, TIPS, PMBM and SEM; $R_7$ may be selected from H, TBS, TROC, and —CO(CH$_2$)$_4$CH$_3$; and $R_8$ may be selected from H and TBS.

The fourth compound may be of a formula selected from:

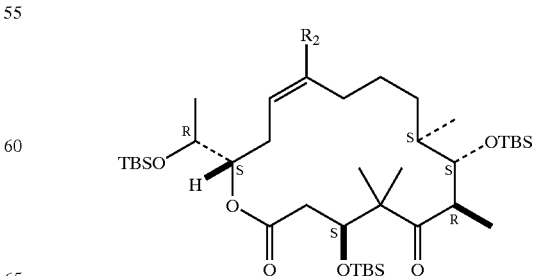

and stereoisomers thereof, where $R_2$ is H or methyl; and the fourth compound may be converted to a fifth compound of a formula selected from:

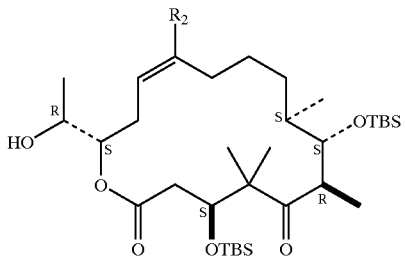

and stereoisomers thereof, where $R_2$ is H or methyl. The fifth compound may be converted to a sixth compound of a formula selected from:

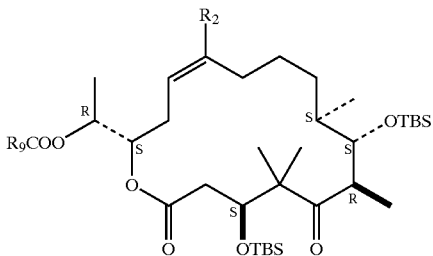

and stereoisomers thereof, where $R_2$ is H or methyl and wherein $R_9$ is selected from alkyl alkenyl, alkynyl, aryl, substituted alkyl, substituted aryl, cycloalkyl and heterocyclo.

The fifth compound may alternatively be converted to a sixth compound of a formula selected from:

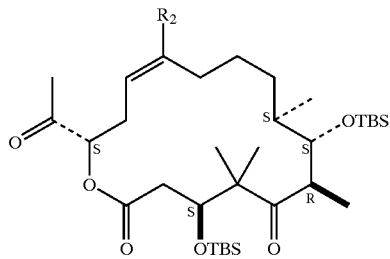

and stereoisomers thereof, where $R_2$ is H or methyl, and the fifth compound may be converted to a sixth compound of a formula selected from:

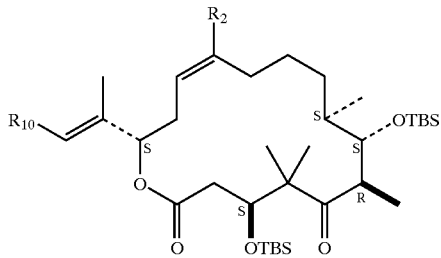

and stereoisomers thereof, where $R_2$ is H or methyl and wherein $R_{10}$ is selected from alkyl, alkenyl, alkynyl, aryl, substituted alkyl, substituted aryl, cycloalkyl and heterocyclo.

The fourth compound may be of a formula selected from:

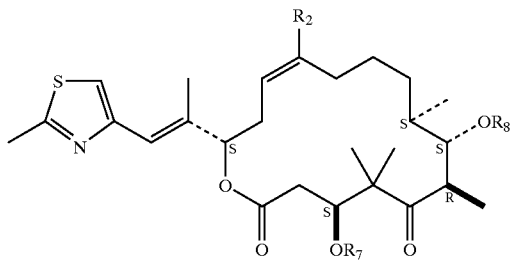

and stereoisomers thereof, where $R_2$ is H or methyl, $R_7$ is H or TBS, and $R_8$ is H, TBS, or TROC, and the fourth compound may be further converted to Epothilone B.

When $R_7$ and $R_8$ each are H, the fourth compound may be further converted to a fifth compound of a formula selected from:

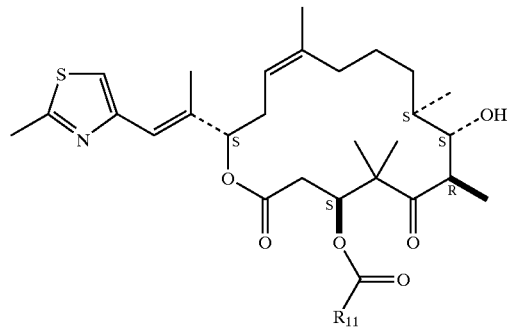

and stereoisomers thereof, wherein $R_{11}$ is selected from alkyl, alkenyl, alkynyl, aryl, alkyl-aryl, alkyloxy, aryloxy, cycloalkyl, heterocyclo, amino, sulfo, and substitutions thereof; and the fifth compound may be further converted to a sixth compound of a formula selected from:

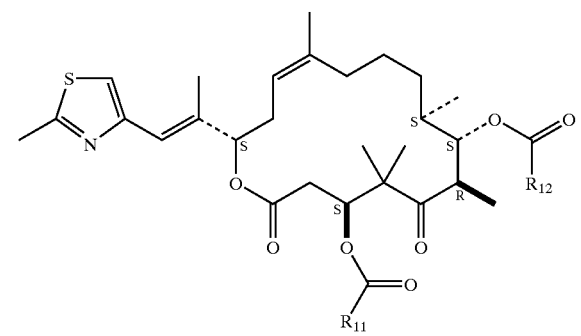

and stereoisomers thereof, wherein $R_{11}$ and $R_{12}$ are each selected from alkyl, alkenyl, alkynyl, aryl, alkyl-aryl, alkyloxy, aryloxy, cycloalkyl, heterocyclo, amino, sulfo, and substitutions thereof.

Alternatively, the fourth compound may be further converted to a fifth compound of a formula selected from:

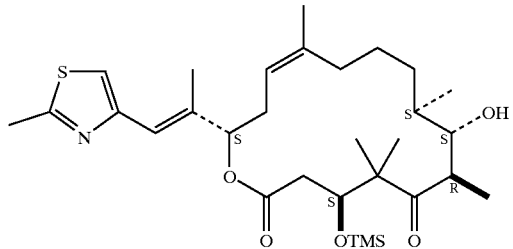

and stereoisomers thereof, and the fifth compound may be further converted to a sixth compound of a formula selected from:

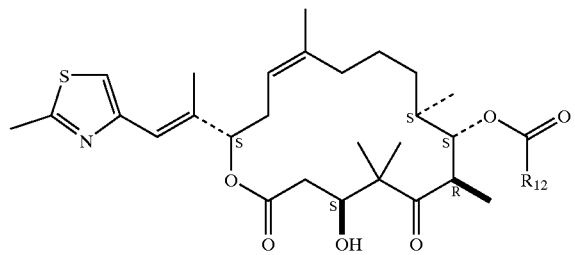

and stereoisomers thereof, wherein $R_{12}$ is selected from alkyl, alkenyl, alkynyl, aryl, alkyl-aryl, alkyloxy, aryloxy, cycloalkyl, heterocyclo amino, sulfo, and substitutions thereof.

When $R_7$ is TBS and $R_8$ is TROC, the fourth compound may be further converted to a fifth compound of a formula selected from:

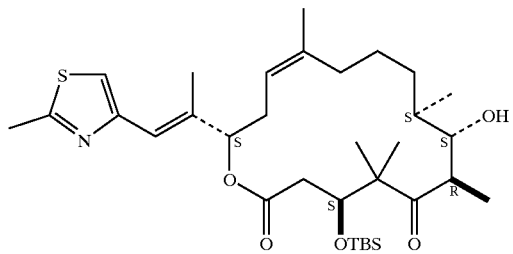

and stereoisomers thereof, and the fifth compound may be further converted to a sixth compound of a formula selected from:

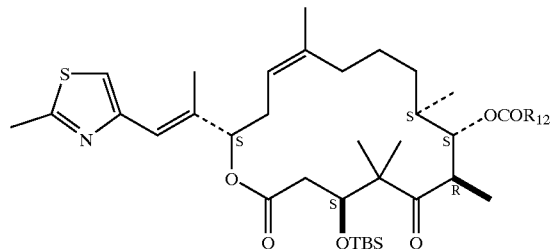

and stereoisomers thereof, wherein $R_{12}$ is selected from alkyl, alkenyl, alkynyl, aryl, alkyl-aryl, alkyloxy, aryloxy, cycloalkyl, heterocyclo, amino, sulfo, and substitutions thereof. The sixth compound may be further converted to a seventh compound of a formula selected from:

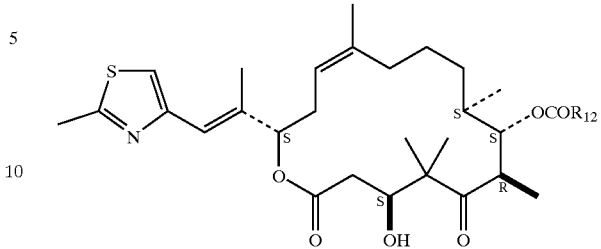

and stereoisomers thereof, wherein $R_{12}$ is selected from alkyl, alkenyl, alkynyl, aryl, alkyl-aryl, alkyloxy, aryloxy, cycloalkyl, heterocyclo, amino, sulfo, and substitutions thereof, and the seventh compound may be further converted to an eighth compound of a formula selected from:

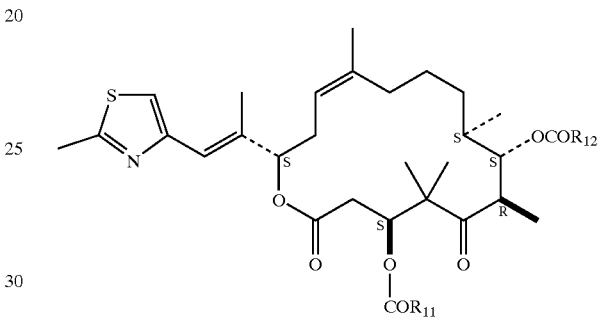

and stereoisomers thereof, wherein $R_{11}$ and $R_{12}$ are each selected from alkyl, alkenyl, alkynyl, aryl, alkyl-aryl, alkyloxy, aryloxy, cycloalkyl, heterocyclo, amino, sulfo, and substitutions thereof.

Alternatively, the fourth compound may be further converted to a fifth compound of a formula selected from:

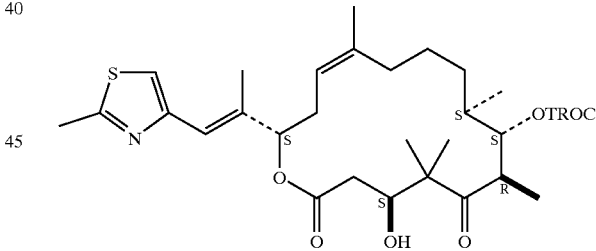

and stereoisomers thereof, and the fifth compound may be further converted to a sixth compound of a formula selected from:

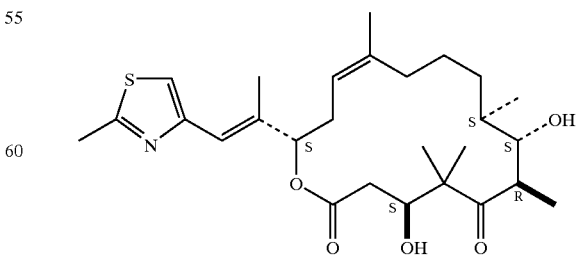

and stereoisomers thereof. The sixth compound may be further converted to Epothilone B. As a further alternative, the fifth compound may be further converted to a sixth compound of a formula selected from:

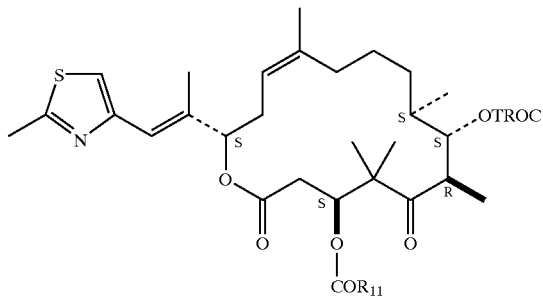

and stereoisomers thereof, wherein $R_{11}$ is selected from alkyl, alkenyl, alkynyl, aryl, alkyl-aryl, alkyloxy, aryloxy, cycloalkyl, heterocyclo, amino, sulfo, and substitutions thereof, and the sixth compound may be further converted to a seventh compound of a formula selected from:

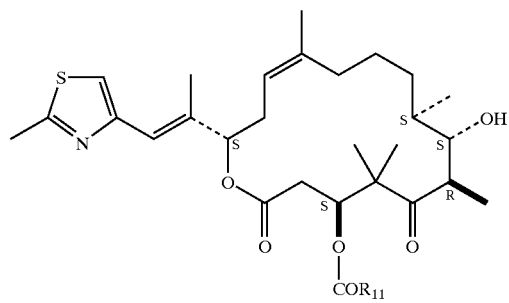

and stereoisomers thereof, wherein $R_{11}$ is selected from alkyl, alkenyl, alkynyl, aryl, alkyl-aryl, alkyloxy, aryloxy, cycloalkyl, heterocyclo, amino, sulfo, and substitutions thereof. This seventh compound may be further converted to an eighth compound of a formula selected from:

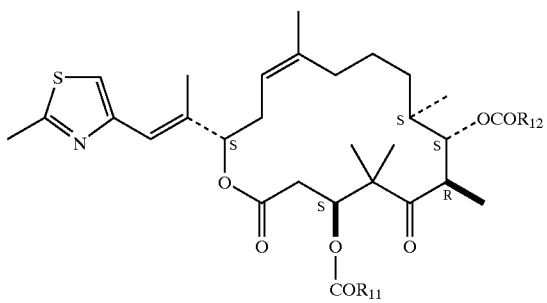

and stereoisomers thereof, wherein $R_{11}$ and $R_{12}$ are each selected from alkyl, alkenyl, alkynyl, aryl, alkyl-aryl, alkyloxy, aryloxy, cycloalkyl, heterocyclo, amino, sulfo, and substitutions thereof.

The present invention also relates to chemical compounds, which may be formed according to the above method or by other methods, and in particular to compounds of the formulas:

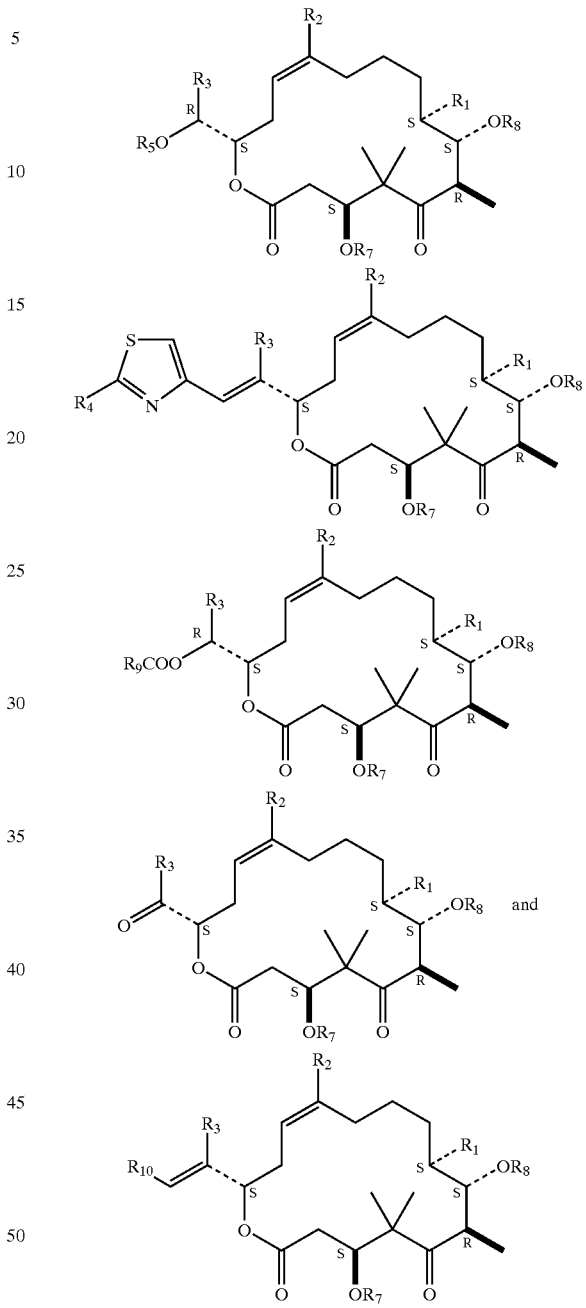

and stereoisomers thereof, wherein $R_1$, $R_2$, $R_3$ and $R_4$ are each selected from H, alkyl, alkenyl, alkynyl, aryl, substituted alkyl, substituted aryl, cycloalkyl and heterocyclo; wherein $R_5$ and $R_6$ are each selected from H and a protecting group; wherein $R_7$ is selected from H, a protecting group and $COR_{11}$; wherein $R_8$ is selected from H, a protecting group and $COR_{12}$; wherein $R_9$ is selected from alkyl, alkenyl, alkynyl, aryl, substituted alkyl, substituted aryl, cycloalkyl and heterocyclo; wherein $R_{10}$ is selected from alkyl, alkenyl, alkynyl, aryl, substituted alkyl, substituted aryl, cycloalkyl and heterocyclo; and wherein $R_{11}$ and $R_{12}$ are each selected from alkyl, alkenyl, alkynyl, aryl, alkyl-aryl, alkyloxy, aryloxy, cycloalkyl, heterocyclo, amino, sulfo, and substitutions thereof.

The present invention also relates to chemical compounds having a formula selected from:

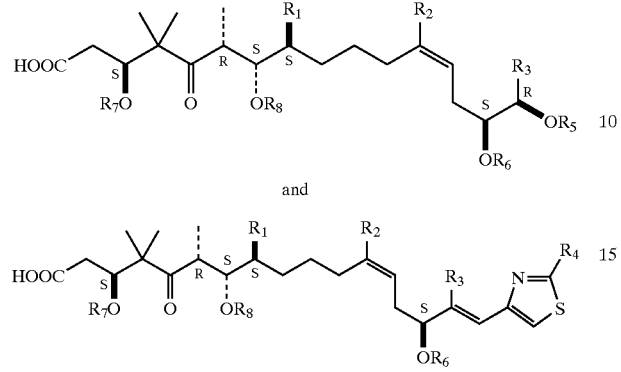

and stereoisomers thereof, wherein $R_1$, $R_2$, $R_3$ and $R_4$ are each selected from H, alkyl, alkenyl, alkynyl, aryl, substituted alkyl, substituted aryl, cycloalkyl and heterocyclo; and wherein $R_5$, $R_6$, $R_7$ and $R_8$ are each selected from H and a protecting group, as well as a method for producing such chemical compounds that are useful in producing epothilones and analogs and derivatives thereof. Broadly, the method comprises performing an aldol condensation of a first compound selected from the formulas:

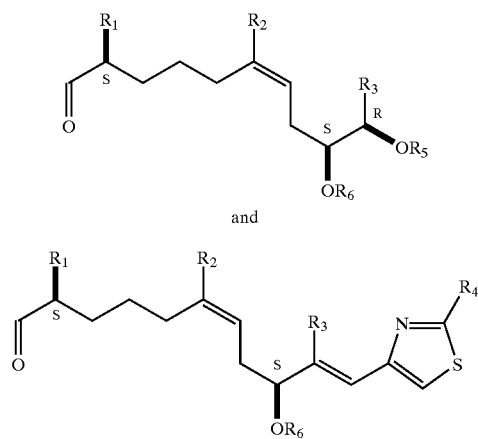

with a second compound selected from the formulas:

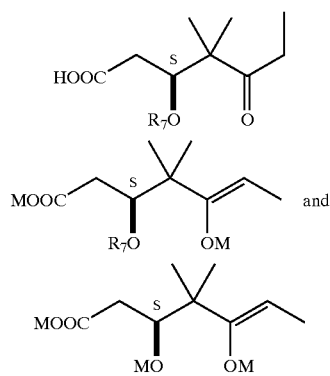

wherein $R_1$, $R_2$, $R_3$ and $R_4$ are each selected from H, alkyl, alkenyl, alkynyl, aryl, substituted alkyl, substituted aryl, cycloalkyl and heterocyclo; wherein $R_5$, $R_6$, $R_7$ and $R_8$ are each selected from H and a protecting group; and wherein M is an alkali metal.

The present invention is also directed to chemical compounds having a formula selected from:

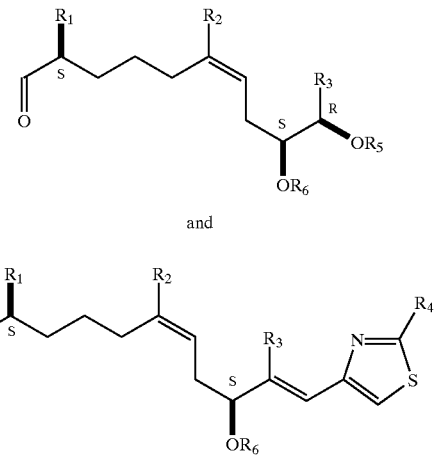

and stereoisomers thereof, wherein $R_1$, $R_2$, $R_3$ and $R_4$ are each selected from H, alkyl, alkenyl, alkynyl, aryl, substituted alkyl, substituted aryl, cycloalkyl and heterocyclo; and wherein $R_5$ and $R_6$ are each selected from H and a protecting group, as well as a number of methods for producing such chemical compounds useful in producing epothilones and analogs and derivatives thereof.

The present invention is further directed to chemical compounds having a formula selected from:

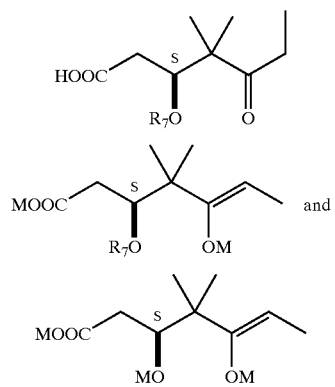

wherein M is an alkali metal, such as lithium, and wherein $R_7$ is selected from H and a protecting group, as well as processes for producing such chemical compounds useful in producing epothilones and analogs and derivatives thereof.

Additionally, the present invention relates to a process for use in producing epothilones and analogs and derivatives thereof, comprising converting a first compound of a formula selected from:

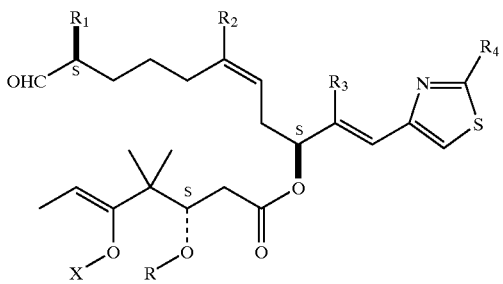

and stereoisomers thereof to a second compound of a formula selected from:

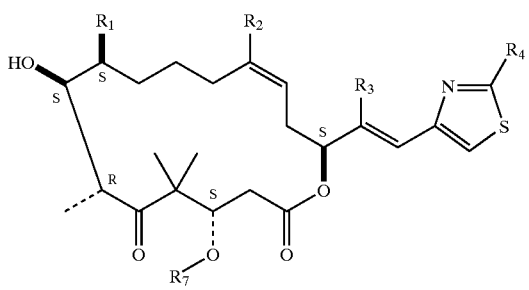

and stereoisomers thereof, wherein $R_1$, $R_2$, $R_3$ and $R_4$ are each selected from H, alkyl, alkenyl, alkynyl, aryl, substituted alkyl, substituted aryl, cycloalkyl and heterocyclo; and wherein $R_7$ is selected from H and a protecting group.

These and other objects of the present invention will become more readily appreciated and understood from a consideration of the following detailed description of the exemplary embodiments of the present invention when taken together with the accompanying drawings, in which:

BRIEF DESCRIPTION OF THE DRAWINGS

FIG. 23 is a diagram of chemical reaction Scheme XXIII according to the present invention;

FIG. 24 is a diagram of chemical reaction Scheme XXIV according to the present invention;

FIG. 26b is a diagram of chemical reaction Scheme XXVIb according to the present invention;

FIG. 29 is a diagram of chemical reaction Scheme XXIX according to the present invention;

DETAILED DESCRIPTION OF THE INVENTION

Total Synthesis of Epothilone A

Epothilones B, 1 and A, 2 (shown above) contain a 16 membered lactone ring with hydroxyl groups at C-3 and C-7, ketone at C-5, epoxide at C-12,13 and an aryl containing side chain at C-16. Both lactone and ketone groups contain β-hydroxy functionality which can presumably be installed via asymmetric aldol condensation. Overall, Epothilone is a typical macrolide possessing an array of alternating methyl and hydroxyl groups of varying stereochemistries.

Figure 1:
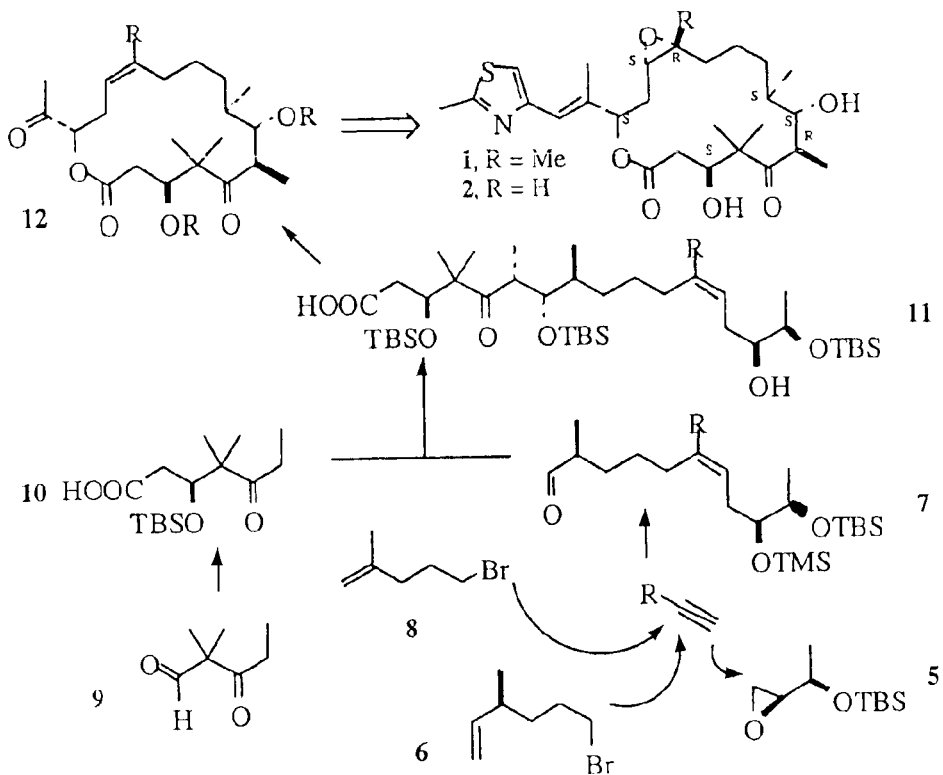
FIG. 1 is a diagram of chemical reaction Scheme I according to the present invention.

We have envisioned the deconstruction of 1 and 2 retrosynthetically as shown in FIG. 1 (Scheme I). The underlying key contruction step in our approach employs a copper (I) promoted Normant coupling of the monoterpene-derived Grignard of 6, with propyne followed by trapping of the resulting organocopper intermediate with Sharpless epoxide 5. This procedure allows for a rapid preparation of the aldehyde 7 required for Aldol condensation with the known keto-acid 10, furnishing the acyclic acid 11. Macrolactonization to 12 followed by simple functional group manipulations is expected to provide Epothilone B.

Figure 2:
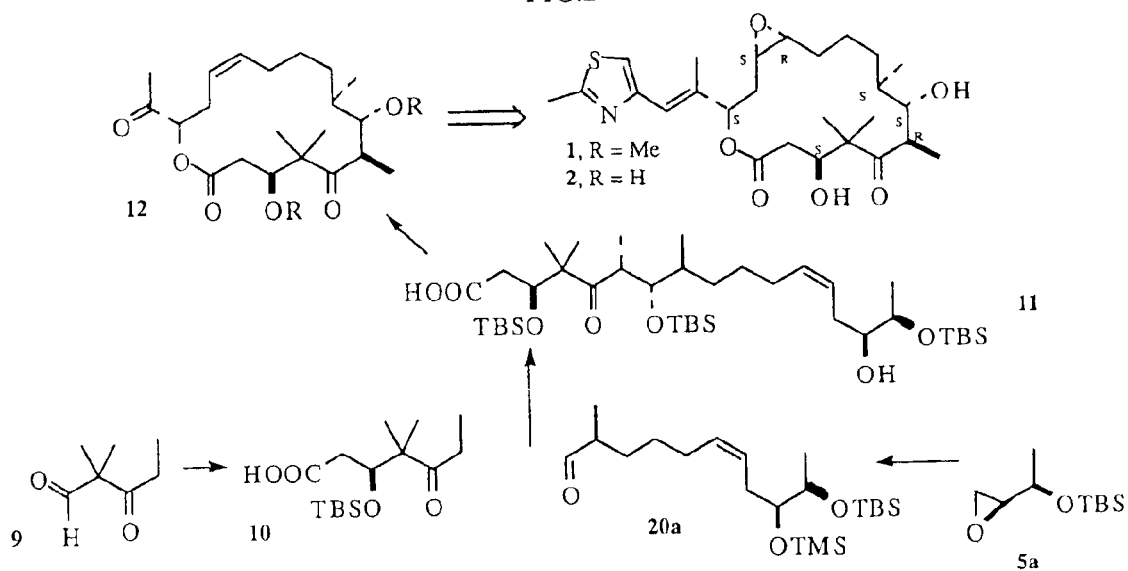
FIG. 2 is a diagram of chemical reaction Scheme II according to the present invention.

A second retrosynthetic scheme we developed was based on the production of Epothilone A 2 by alkyne opening of an epoxide, which later lead stereoselectively to a cis-olefin and thereby the 12,13-cis epoxide moiety as shown in FIG. 2 (Scheme II). A few aspects of this work have been published (Bijoy, P. and M. A. Avery, *Synthetic studies directed towards epothilone A: enantioselective synthesis of a C7–C15 carboxaldehyde segment*. Tetrahedron Lett., 1998. 39(3/4): p. 209–212), and application to the total synthesis of Epothilone A, 2, has been pursued in parallel to the alternate route outlined in FIG. 1 (Scheme I). Apart from the aldehyde 21:

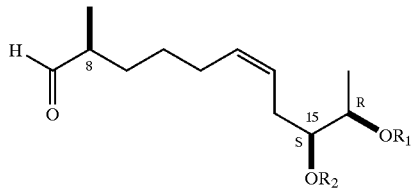

Figure 3:
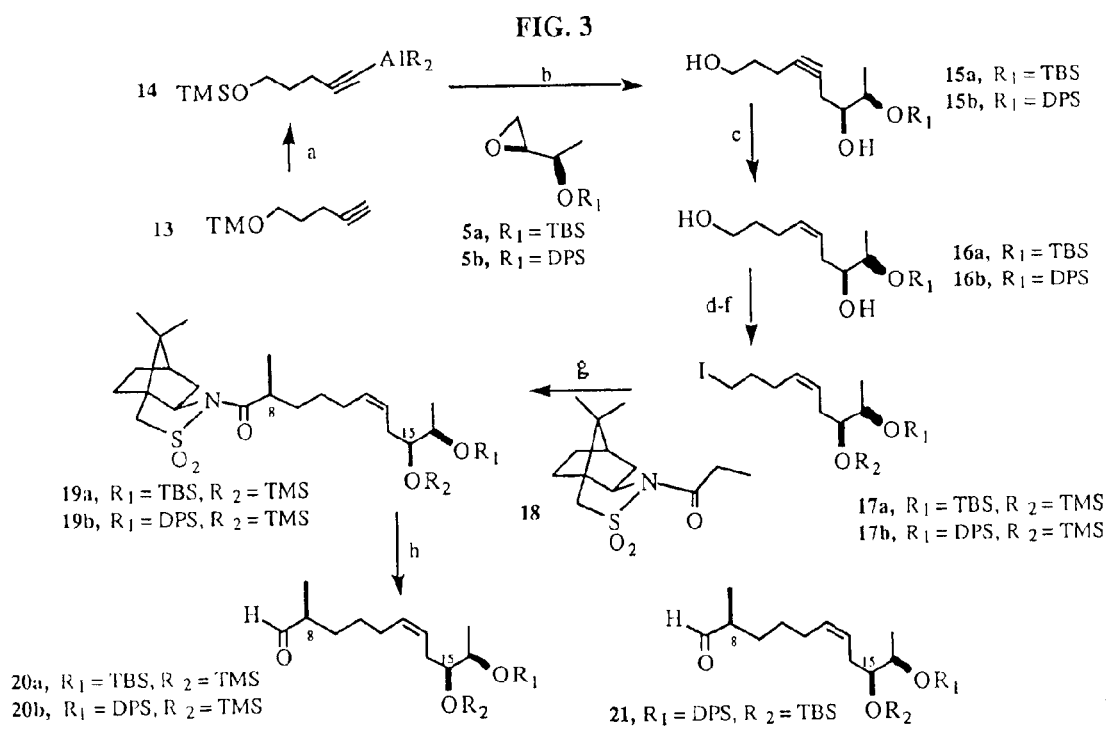
FIG. 3 is a diagram of chemical reaction Scheme II according to the present invention.

21, $R_1$ = DPS, $R_2$ = TBS reported in our earlier work we also prepared the aldehydes 20a and 20b essentially having different protecting groups at the secondary hydroxyl groups, as shown in FIG. 3 (Scheme III).

The synthesis of 20a and 20b shown in FIG. 3 (Scheme III) involves preparation of the alkynylalane 14 from the alkyne 13, that upon opening of 5 and dil.HCl quench gave the diol 15. Selective reduction of the alkyne 15 (Lindelar reduction) provided the required Z-olefin 16. A sequence of events transforms 16 into iodide 17: selective tosylation at the primary alcohol; protection of the secondary alcohol as the TBS (tert-butyldimethylsilyl) occurs without disturbing the primary tosylate, and finally, NaI displaces the tosylate to give the iodide 17. Alkylation of this iodide with the enolate of propionyl amide 18 prepared from the (–)-camphorsultam afforded the homologated material, auxiliary intact, 19. DIBAH reduction of the adduct 19 resulted in the aldehydes 20a and 20b. The aldehydes 20a and 20b are the desmethyl counterparts to aldehyde 7 in FIG. 1 (Scheme I). The overall process is 7 steps from pentynyl derivative 13.

Figure 4:
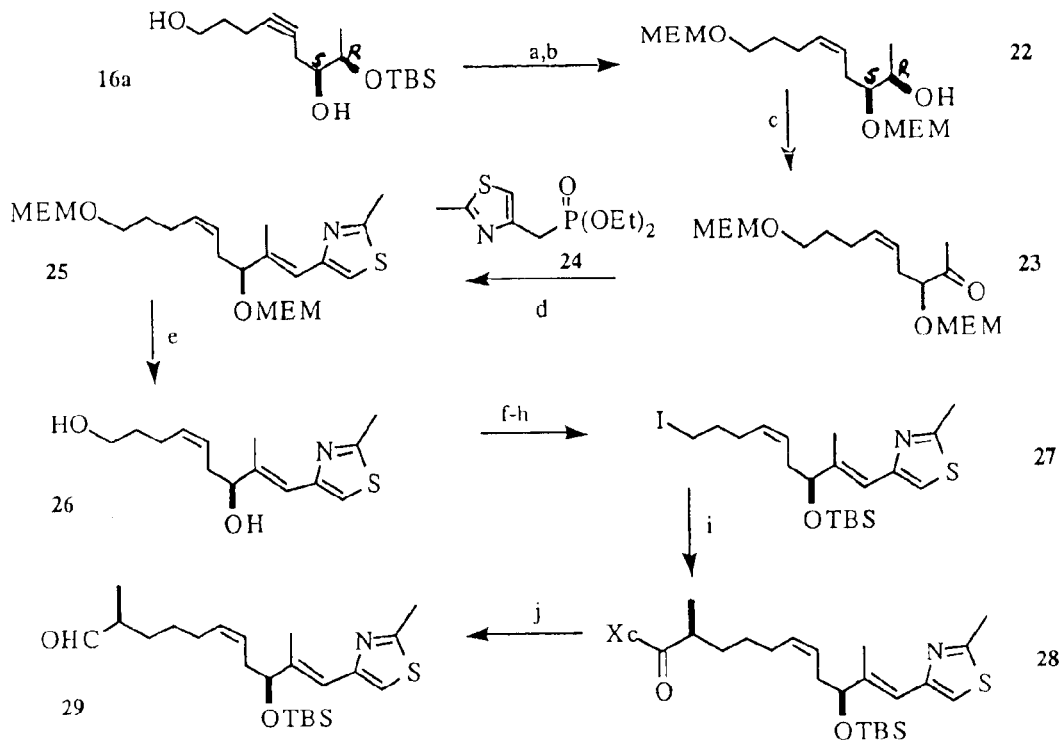
FIG. 4 is a diagram of chemical reaction Scheme IV according to the present invention.

Alternatively, the side-chain thiazole ring could be installed to provide the aldehyde 29 as outlined in FIG. 4 (Scheme IV). In this approach treatment of 16a with MEM-Cl yielded the bis-MEM ether. Desilylation of the bis-MEM ether with fluoride ion gave 22, oxidation of which then provided the ketone 23. Horner Emmons Reaction of 23 with the phosphonate anion of 24 then afforded the diene 25.

Remarkably, 25 could not be deprotected readily under expected conditions, but required concentrated HCl solution to effect transformation into the diol 26. The primary alcohol of diol 26 was smoothly tosylated, and the secondary alcohol silylated with TBSOTf. Upon Sn2 displacement of the primary toxylate, the iodide 27 was isolated as a light yellow, reasonably stable oil. Alkylation of the iodide with the anion of sultam 18 gave adduct 28. Reduction to the adduct 28 with DIBAH provided the requisite aldehyde 29 which was identical in all respects compared to the one reported by Nicolaou (Nicolaou, K. C., et al., *Total Syntheses of Epothilones A and B via a Macrolactonization-Based Strategy*. J. Am. Chem. Soc., 1997. 119(34): p. 7974–7991).

The aforementioned aldehydes 7, 20a, 20b, 21, and 29, and stereoisomers thereof, can be represented by the following general formula:

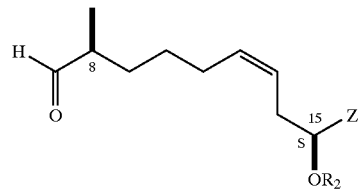

where Z is

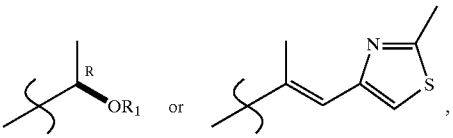

$R_1$ is TBS or DPS and $R_2$ is TMS, TBS Stereoisomers of these aldehydes can be similarly represented.

For aldol condensation required by Scheme I, the silyl-protected keto-acid 10 was required. As reported by a unique route, Nicolaou (Nicolaou, K. C., et al., *Total Syntheses of Epothilones A and B via a Macrolactonization-Based Strategy*. J. Am. Chem. Soc., 1997. 119(34): p. 7974–7991) reported that the silyl-protected keto-acid 10 had a rotation ($[a]^D$) of +16.1°. According to De Brabander (De Brabander, J., S. Rosset, and G. Bernardinelli, *Towards a synthesis of epothilone A. Rapid assembly of the C(1)–C(6) and C(7)–C (12) fragments*. Synlett, 1997(7): p. 824–826), this acid could be prepared from the N-propionate of the (+)-Sultam 30 as outlined in FIG. 5 (Scheme V). De Brabander reported a rotation value for sultam 33 of +119°, depicted the alcohol stereocenter as S, and deposited the crystal structure in the Cambridge Crystallographic Database (CCD). However, perusal of structure 33 in the CCD shows clearly that the alcohol stereocenter is R, opposite of that drawn in the paper.

Furthermore, no rotation value was given for the acid 34 except stating that this acid was previously reported by Nicolaou. Without confirming the X-ray results reported by De Brabander by logging into the CCD, one would assume the correct acid to be derived from Scheme V. In fact, when we prepared the TBS-acid 34 as outlined, the rotation value we obtained was in good agreement with Nicolaou at +17.4°. DeBrabander later corrected his first publication. De Brabander, J., S. Rosset, and G. Bernardinelli, *Towards a synthesis of epothilone A. Rapid assembly of the C(1)–C(6) and C(7)–C(12) fragments. [Erratum to document cited in CA 127:234203]*. Synlett, 1998(6): p. 692; De Brabander, J., S. Rosset, and G. Bernardinelli, *Towards a synthesis of epothilone A. Rapid assembly of the C1–C6 and C7–C12* fragments. [*Erratum to document cited in CA* 127:234203]. Synlett, 1998(3): p. 328.

Figure 5:
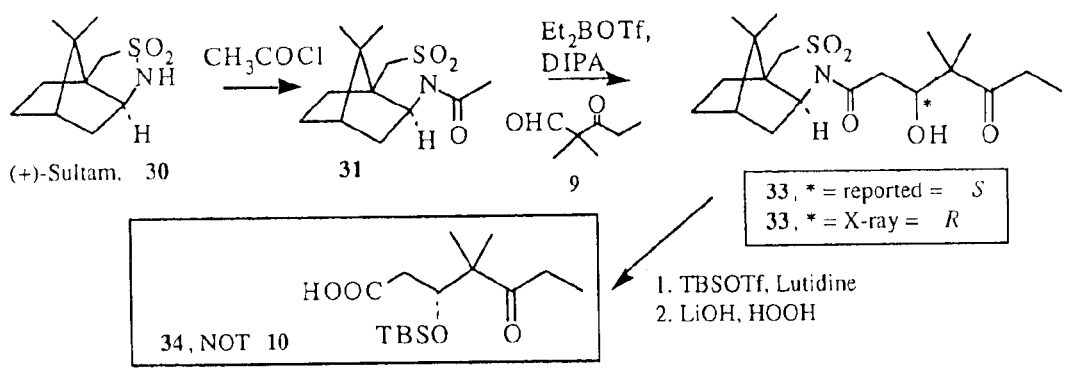
FIG. 5 is a diagram of chemical reaction Scheme V according to the present invention.
Figure 5A:
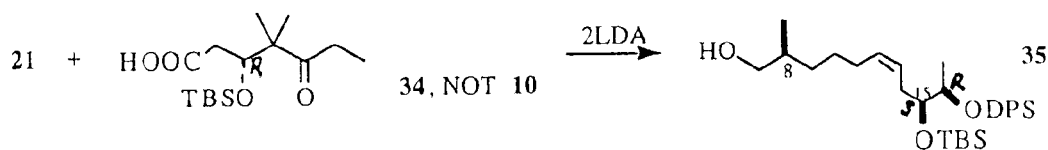
FIG. 5a is a diagram of chemical reaction Scheme Va according to the present invention.
Figure 6:
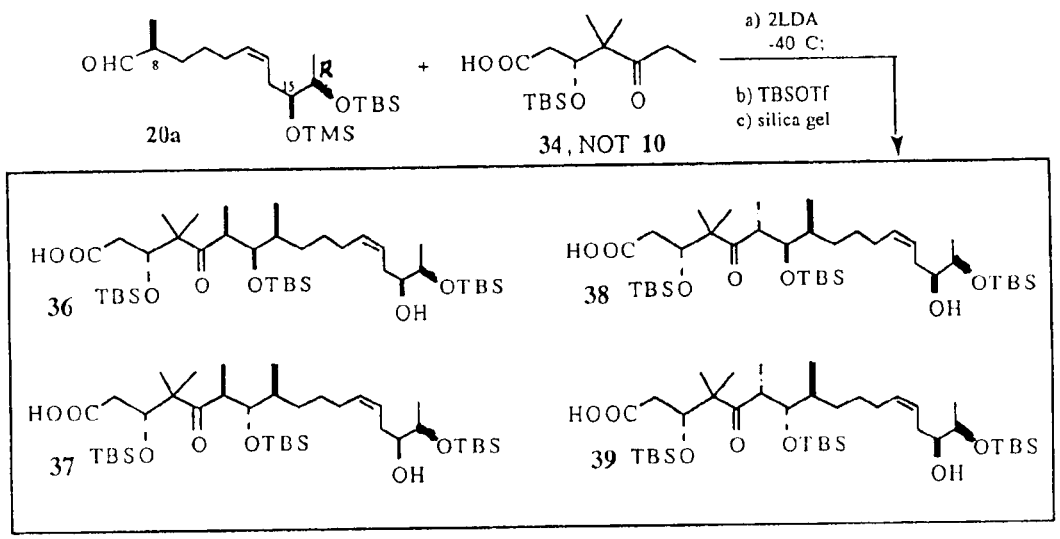
FIG. 6 is a diagram of chemical reaction Scheme VI according to the present invention.

When the TBS acid we assumed was 10 (shown in FIG. 5 (Scheme V)) was condensed with aldehyde 21, reduced product 35 was obtained as shown in FIG. 5a (Scheme Va). In the course of investigations, it was determined that the bulky diphenyltertbutylsilyl (DPS) & tertbutyldimethylsilyl (TBS) groups were responsible for this unexpected result. When the aldehyde 20b (TMS replaces TBS) was used, the aldol reaction did take place but the yields were only moderate. On the other hand the aldol reaction with 20a went much more smoothly to give a mixture of 4 diastereomeric aldol adducts in good yields. In order to convert these linear products to materials we could match to literature, we trapped the intermediate aldolates with TBSOTf, and the labile TMS group was then lost during chromatography to give 36–39 as shown in FIG. 6 (Scheme VI). These acids, 36–39, as well as stereoisomers thereof, may be represented by the following general formula

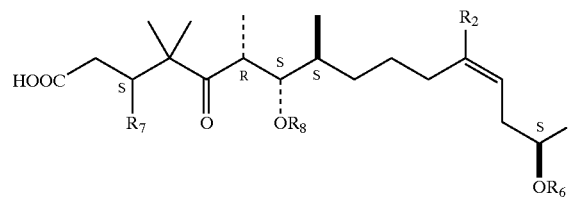

where Z is

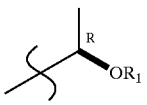

and where $R_1$, $R_7$, and $R_8$ are each TBS. The isomers as a mixture were cyclized with $Cl_3C_6H_2COCl$, pyridine, DMAP to afford lactones 40–43:

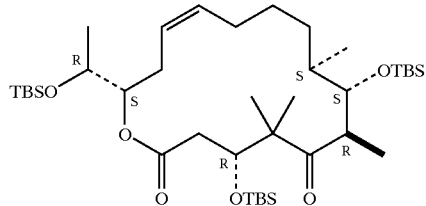

40

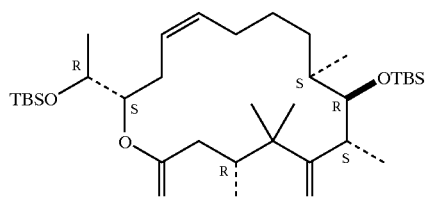

41

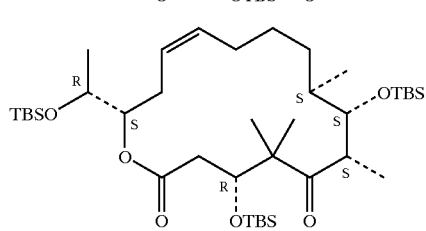

42

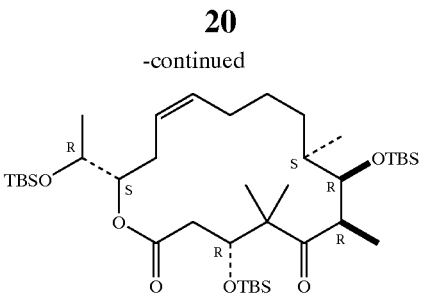

43

The lactones 43 and stereoisomers thereof, may be represented by the general formula

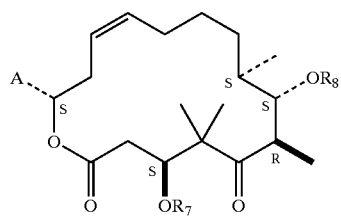

where A is

Figure 7:
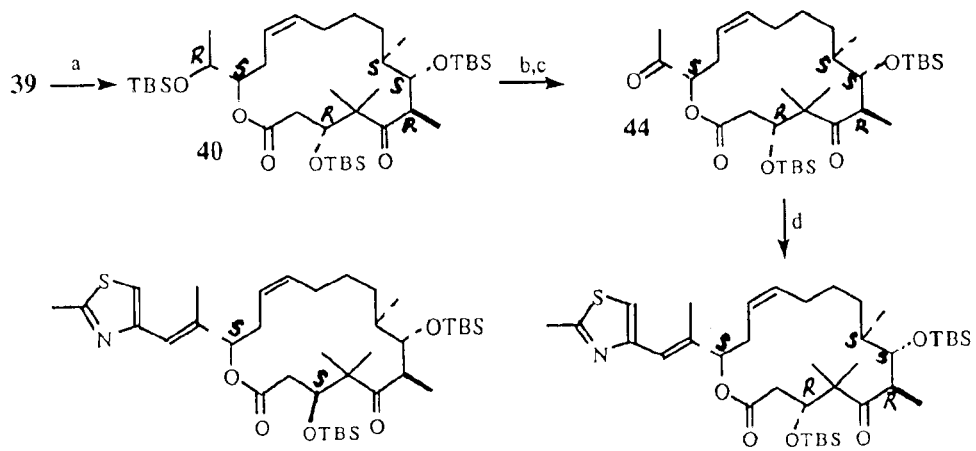
FIG. 7 is a diagram of chemical reaction Scheme VII according to the present invention.

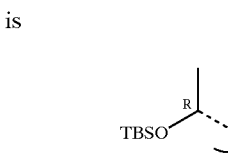

and $R_7$ and $R_8$ are each TBS. As indicated in FIG. 7 (Scheme VII) and FIG. 8 (Scheme VIII), each diastereomer was then selectively deprotected, oxidized to methyl ketone (evident by NMR), and finally, reacted with Horner-Emmons reagent 24 to furnish penultimate intermediates on the way to a route to Epothilone A reported by Nicolaou. In this report, spectral data for 46:

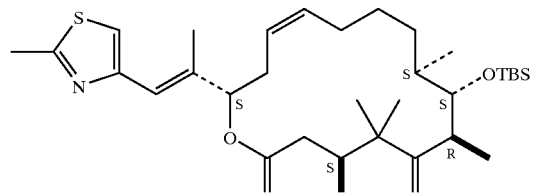

Figure 8:
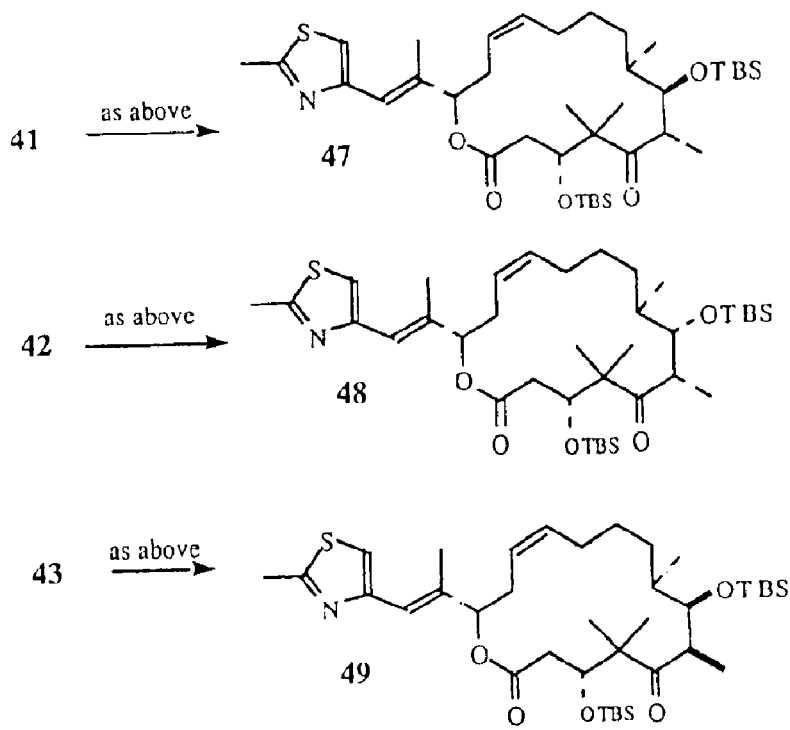
FIG. 8 is a diagram of chemical reaction Scheme VIII according to the present invention.

46, Nicolaou was slightly different from each isomer brought forward, intermediates 45,47–49 shown in FIG. 7 (Scheme VII) and FIG. 8 (Scheme VIII). Intermediate 46 may also be represented by the following general formula

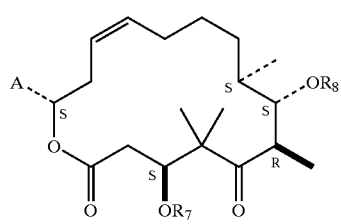

where A is

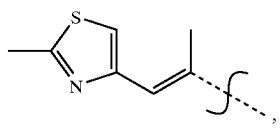

and $R_7$ $R_8$ are each TBS. As should be understood, intermediates 45 an 47–49, and their stereoisomers, may be similarly represented. None of these products matched known material. Each stereocenter was individually checked, including the synthesis of the α-methyl diastereomer of the aldehyde 29 to make sure we have the correct stereochemistry. Finally, we checked the lactones from Daneshevsky's synthesis of epi-epothilones, and matched lactone 45 with known material. This clearly indicated that the keto-acid reported to be 10 was incorrectly assigned by De Brabander and was in fact keto-acid 34. This also confirms the error in reporting the sign of the optical rotation of 10 by Nicolaou.

Figure 9:
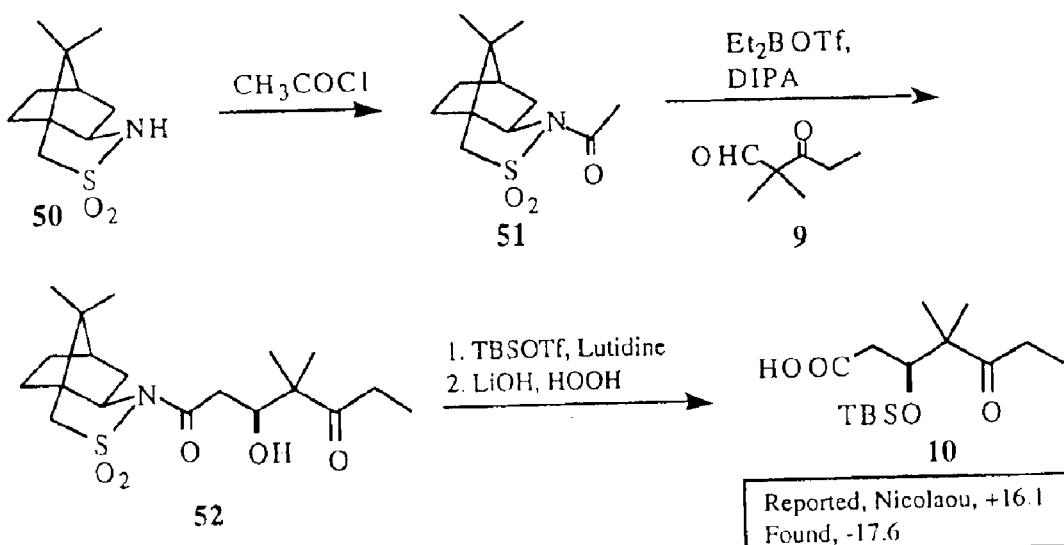
FIG. 9 is a diagram of chemical reaction Scheme IX according to the present invention.

With this revelation at hand, we prepared 10 with the opposite sign of rotation as reported by Nicolaou, as shown in FIG. 9 (Scheme IX), by condensation with the N-acetyl derivative 51, prepared from (–)-sultam (50) and acetyl chloride, with aldehyde 9. After silylation and removal of auxillary, we obtained 10 with sign of rotation opposite that reported by Nicolaou (Scheme IX).

Figure 10:
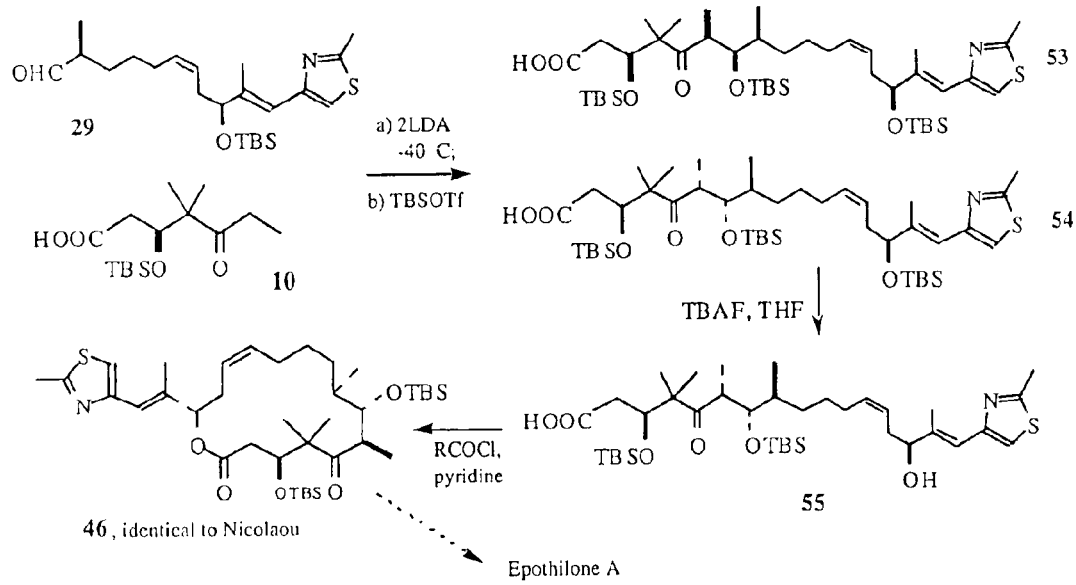
FIG. 10 is a diagram of chemical reaction Scheme X according to the present invention.

As final proof of this reassignment to the sultam route to 10, we condensed bonafide 10 with aldehyde 29 as shown in FIG. 10 (Scheme X). The resulting acids 53 and 54 were identical to reported materials by proton and carbon NMR, and the signs of rotation were as reported. Finally, selective deprotection of 54 to give the alcohol 55 was followed by cyclization to afford the reported precursor to Epothilone A, 46. This formally completes the synthesis of Epothilone A.

Figure 11:
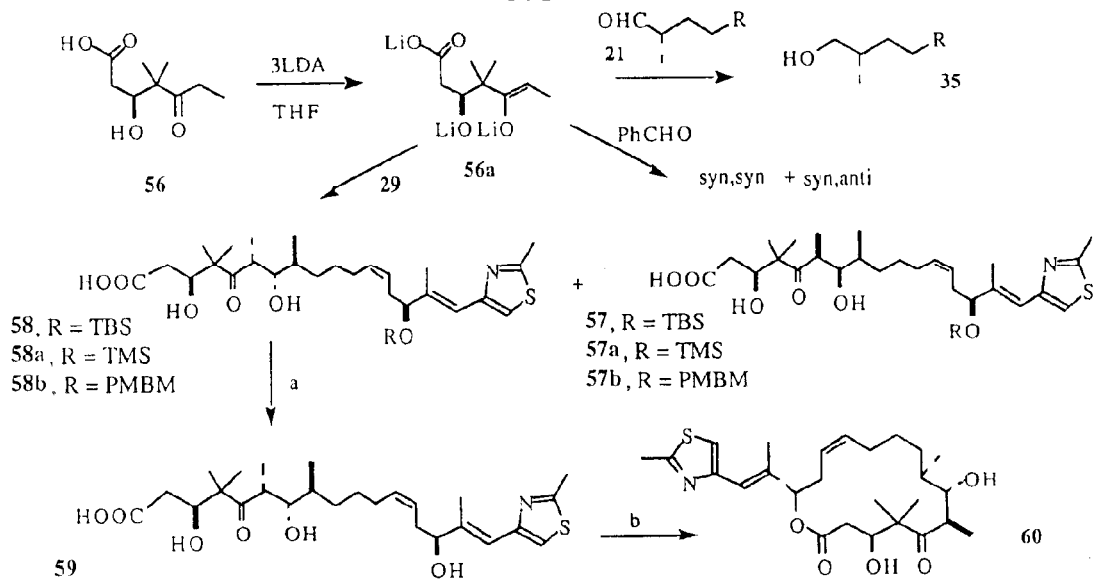
FIG. 11 is a diagram of chemical reaction Scheme XI according to the present invention.

In order to reduce the total number of steps en route to the epothilones, the trianion of acid 56 has been examined in a model system such as benzaldehyde and gave outstanding chemical yields, but in a 1:1 ratio of syn,syn to syn,anti. With 21 however, 56 led to sole production of the reduced aldehyde, alcohol 35, as shown in FIG. 11 (Scheme XI). On the other hand reaction with 29 resulted in the aldol products 57 and 58. Removal of the TBS group of 58 using TBAF afforded the triol acid 59, which on macrocyclization gave 60, the precursor to Epothilone A (Scheme XI).

Figure 12:
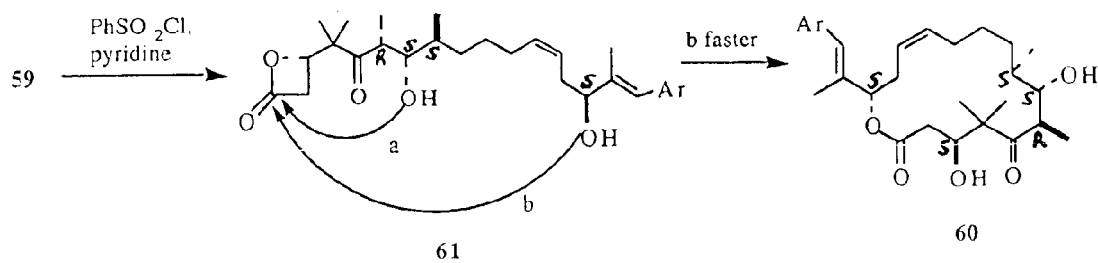
FIG. 12 is a diagram of chemical reaction Scheme XII according to the present invention.

Presumably, macrolactonization of the triol-acid 59 gave the desired product based on the relative rates of 4- vs 8- vs 16-membered ring closures, as indicated in FIG. 12 (Scheme XII). The relative rates are 0.58, 1.5×10$^{-4}$, and 3×10$^{-3}$, respectively, clearly indicating an initial preference for β-lactone formation. Casadei, M. A., C. Galli, and L. Mandolini, *Ring-Closure Reactions. 22. Kinetics of Cyclization of Diethyl(w-Bromoalkyl)malonates in the Range of 4- to 21-Membered Rings. Role of Ring Strain.* J. Amer. Chem. Soc., 1984. 106: p. 1051–1056. However, it is also known that β-lactones are excellent active esters and react with alcohols to give ring-opened esters. Lactonization conditions applied to 59 probably formed the β-lactone 61, but subsequent in situ trans-lactonization resulted in formation of the desired 16-membered lactone 60.

Acids 53 and 54, alcohol 55, aldol products 57 and 58, triol acid 59, discussed above, and their stereoisomers, may be represented by the common following formula

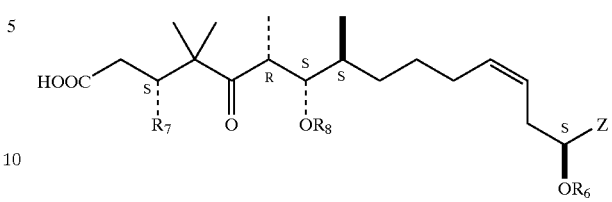

where Z is

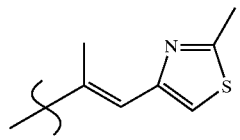

and $R_6$ is TBS, H, TMS, or PMBM, and where $R_7$ and $R_8$ are either H or TBS.

Figure 13:
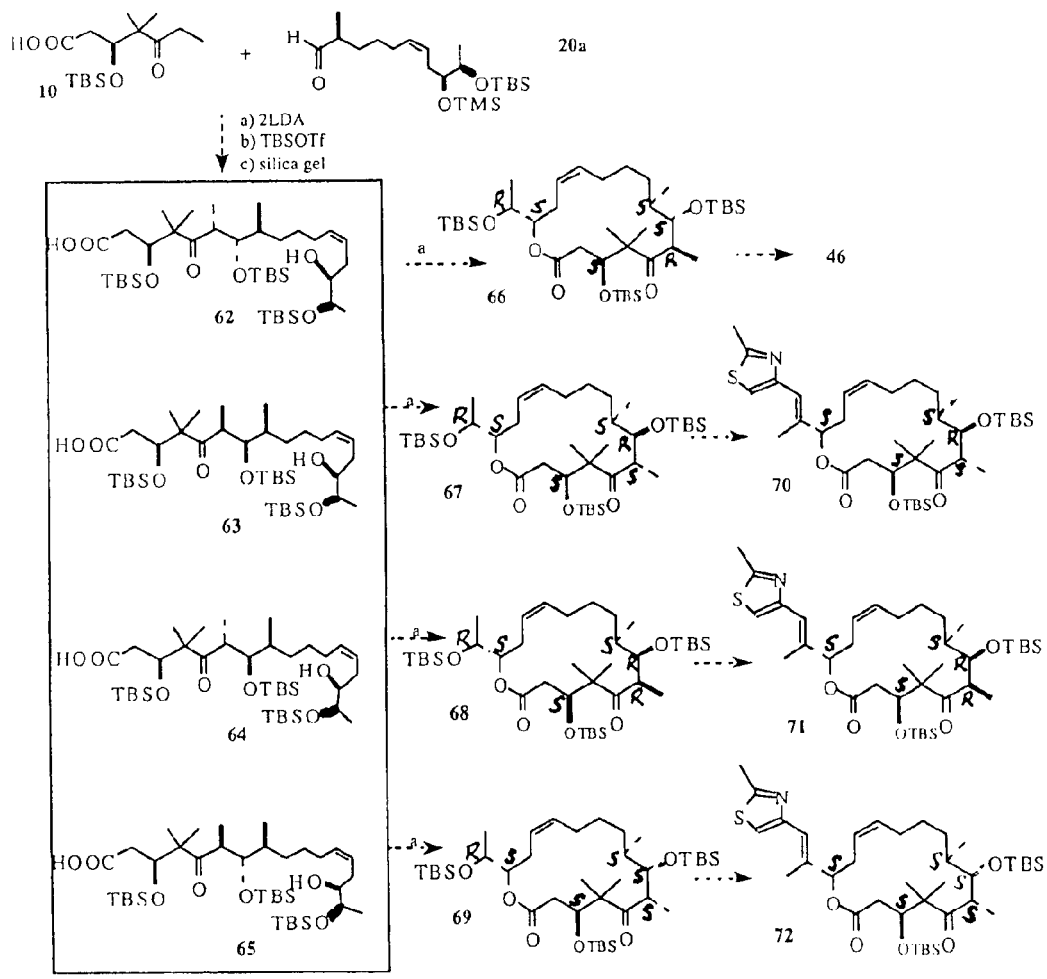
FIG. 13 is a diagram of chemical reaction Scheme XIII according to the present invention.

Similarly, reaction of 10 with the aldehyde 20a resulted in the aldol adducts 62–65 which on further transformations as outlined previously afforded the corresponding cyclic lactones 46, 70–72, as shown in FIG. 13 (Scheme XIII). These lactones. 70–72, as well as their stereoisomers, may be represented by the following general formula

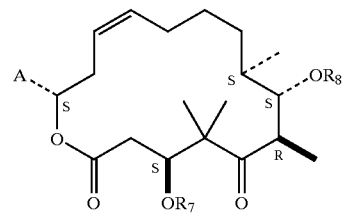

where A is

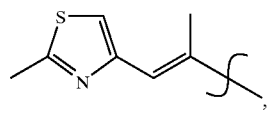

and $R_7$ and $R_8$ are each TBS. Similarly, intermediates 66–69 and their stereoisomers may be represented by the following general formula

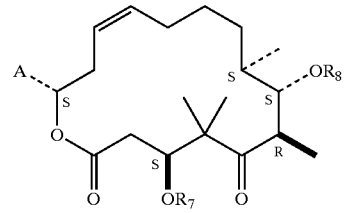

A is

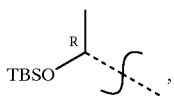

and R₇ and R₈ are each TBS.

Figure 14:
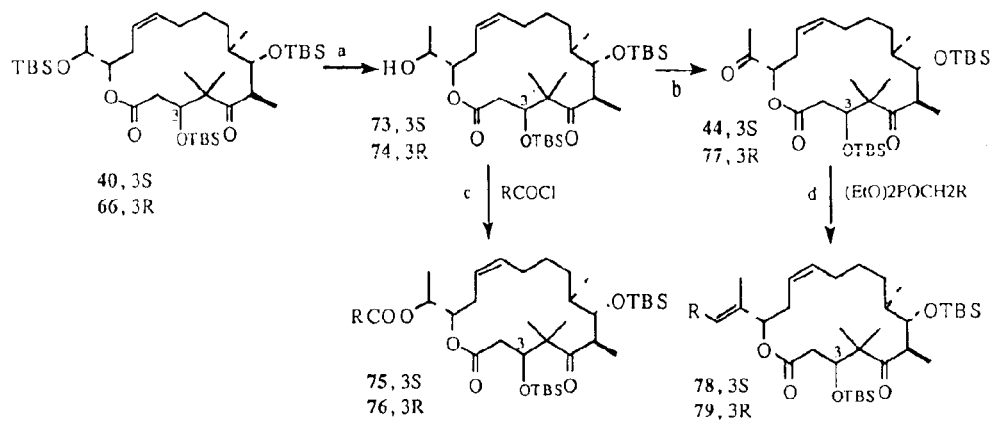
FIG. 14 is a diagram of chemical reaction Scheme XIV according to the present invention.

With reference to FIG. 14 (Scheme XIV), in all of the above cases (e.g. Schemes VII, VIII, XII, etc.), the corresponding 3S alcohols 73 and ketones 44 provide starting materials which can be derivatized and the resulting products 75 and 78 used as bioactive substances (R=alkyl, aryl, heterocyclic). Obviously, related 3R intermediates 74 and 77 can be processed similarly to furnish the 3R products 76 and 79. Diastereomeric materials can be carried forward in the same fashion. The alcohols 73, and their stereoisomers, may be represented by the general formula

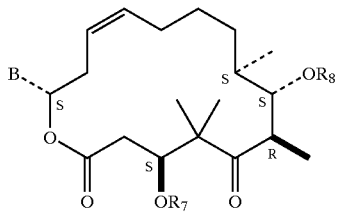

where B is

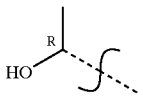

and R₇ and R₈ are each TBS. As should be understood, R₇ and R₈ could also be H. The ketones 44 and resulting products 75 and 78, and stereoisomers thereof, may be represented by the general formula

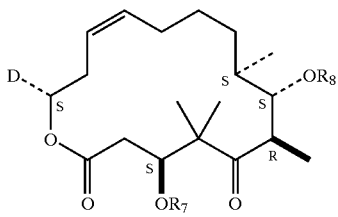

where D is

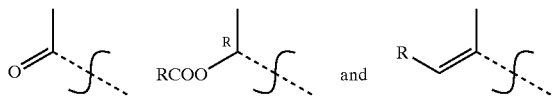

respectively, R is alkyl, aryl, or heterocyclic, and R₇ and R₈ are each TBS.

Collectively, these alcohols, ketones, and aldol products, as well as their respective stereoisomers, may be represented as follows:

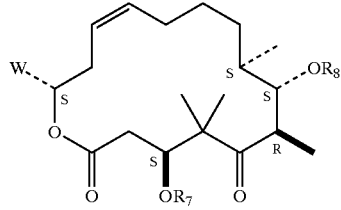

where W is

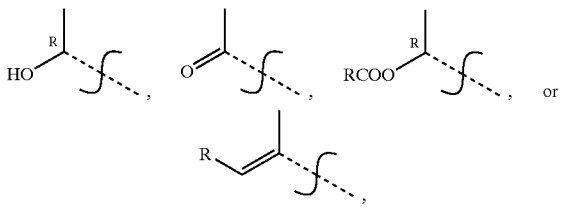

R is alkyl, aryl, or heterocyclic, and R₇ and R₈ are each TBS.

Total Synthesis of Epothilone B

Figure 15:
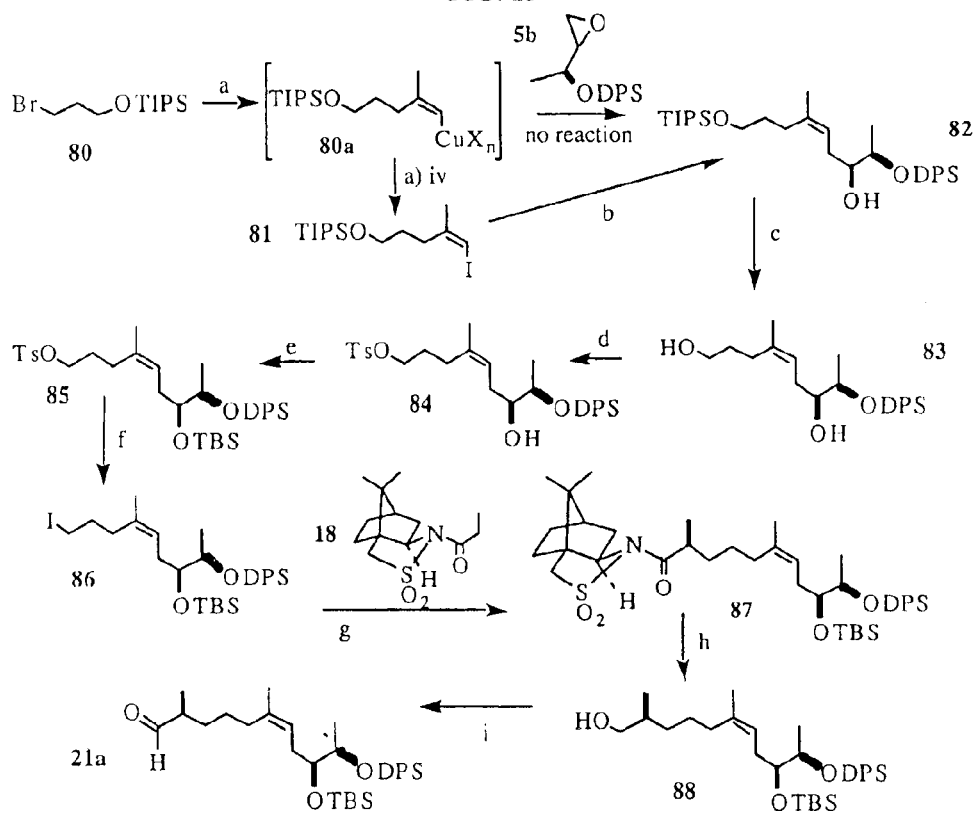
FIG. 15 is a diagram of chemical reaction Scheme XV according to the present invention.

Total synthesis of 1 via Scheme I is based upon a Normant reaction in which an acetylene derivative such as propyne or TMS-acetylene was coupled to a Grignard reagent in the presence of Cu(I), and the intermediate cuprate was then used as a nucleophile to open a Sharpless epoxide such as 5. Numerous cases were examined to find the best conditions and protecting groups to facilitate the overall synthesis, and started with the addition of the TIPS protected Grignard 80 to propyne as outlined in FIG. 15 (Scheme XV). Addition of Cu(I) to the Grignard derived from 80, followed by propyne resulted in an intermediate vinyl cuprate 80a that could not effect opening of epoxide 5b, but could be quenched with iodine to furnish the Z-vinyl iodide 81 in excellent yield. Metallation of the vinyl iodide with alkyl lithium and metal exchange with an aluminum chloride provided a sufficiently reactive vinylalane which effected opening of the DPS protected epoxide 5b to give the differentially protected triol 82. Desilylation of 82 with dilute acid and selective tosylation gave the tosylate 84, that upon silylation with TBSOTf gave disilylated tosylate 85. Upon Sn2 displacement with iodide, the stable iodide 86 was formed and alkylated with the propionosultam 18 to give 87, by analogy to formation of 20. Overreduction with lithium aluminum hydride gave alcohol 88, and finally, reoxidation with pyridine-SO₃ complex furnished the target aldehyde 21a.

Figure 16:
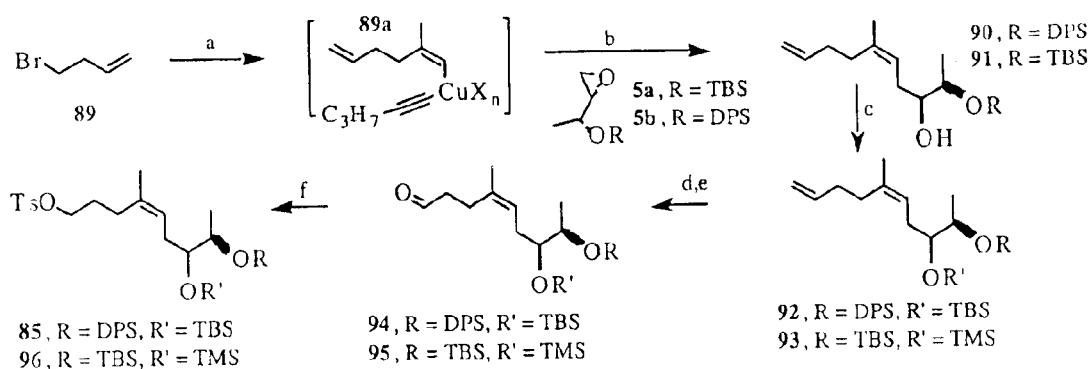
FIG. 16 is a diagram of chemical reaction Scheme XVI according to the present invention.

An alternative approach to the preparation of the aldehyde 21 which bypassed the iodoalkene intermediate 81 was examined involving addition of an olefinic Grignard derived from 89 at the outset instead of the TIPS ether 80, as shown in FIG. 16 (Scheme XVI). Apparently, the presence of a g-TIPSO moiety had a detrimental effect on the ensuing epoxide opening via cuprate intermediate 80a. On the other hand, the cuprate intermediate 89a suffered no such limitation after ligand exchange with pentynyl lithium, and smoothly effected opening of 5b to furnish the alcohol-diene 90 in excellent yields. Conversion to the known tosylate 85 was then accomplished as follows: Silylation gave the TBS ether 91; oxidation of the less hindered terminal olefin was achieved with AD-mix α, and the resulting diol cleaved to aldehyde 92 with periodate. Finally, reduction to alcohol and tosylation gave 85.

Unfortuantely however, aldehyde 21a behaved identically to 21 in attempted aldol condensation, giving reduction product 88:

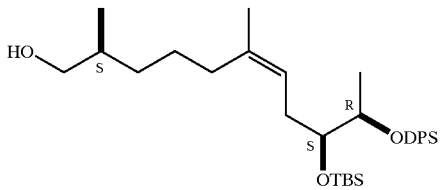

Figure 17:
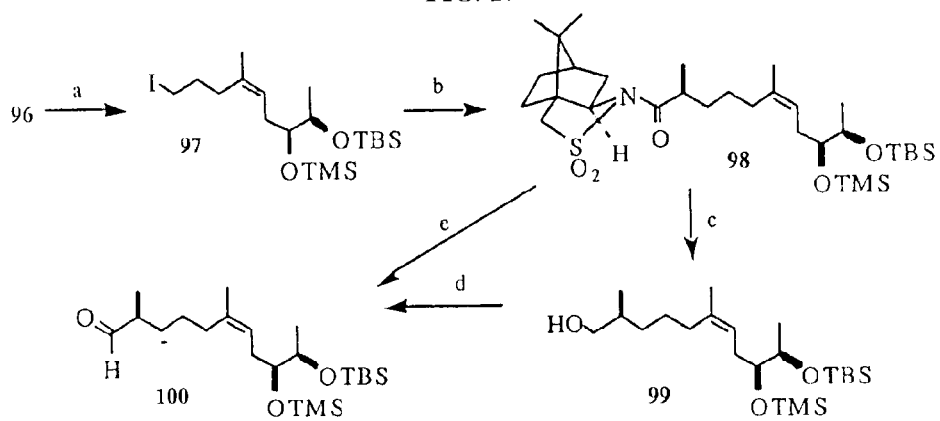
FIG. 17 is a diagram of chemical reaction Scheme XVII according to the present invention.
Figure 18:
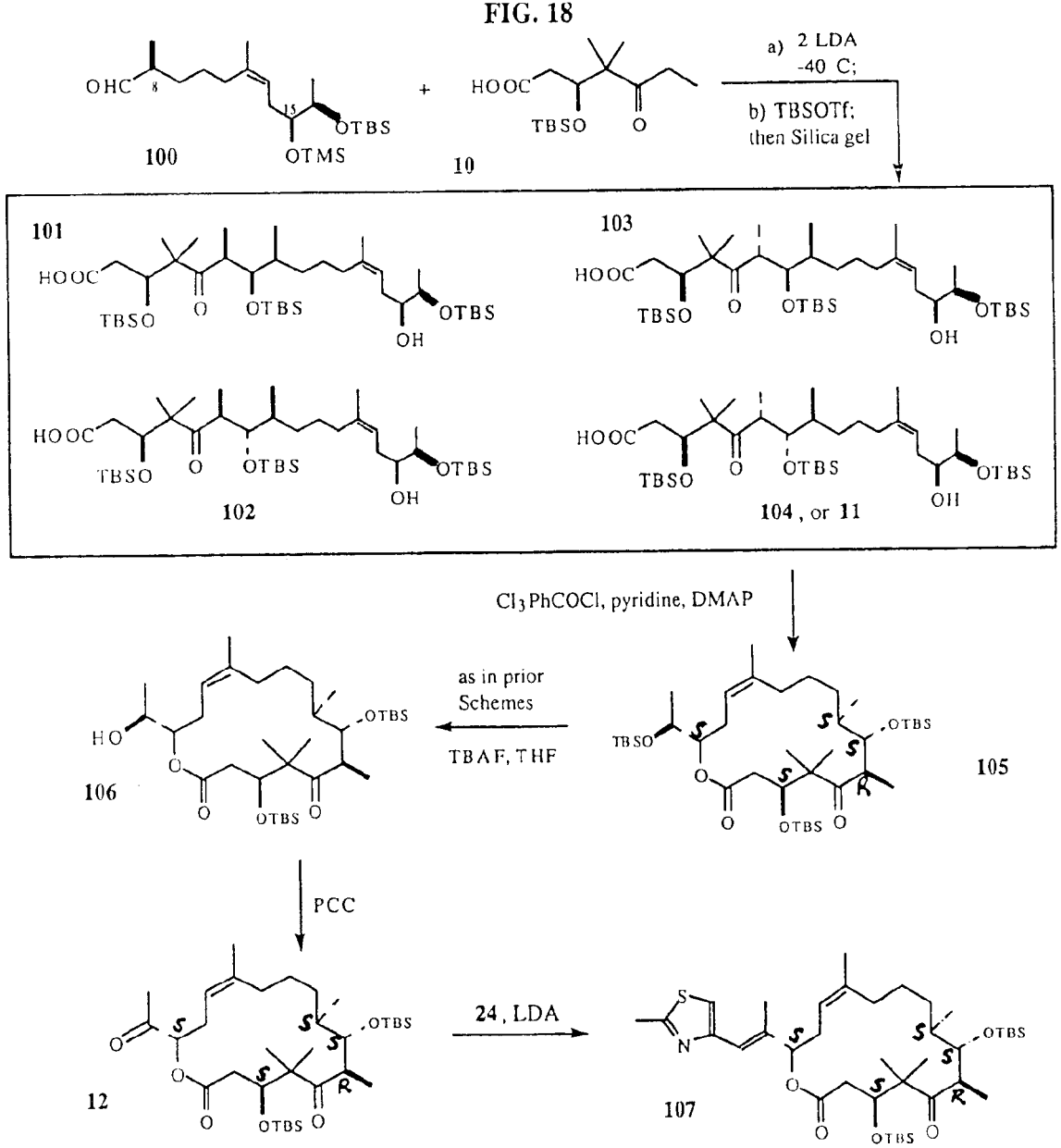
FIG. 18 is a diagram of chemical reaction Scheme XVIII according to the present invention.

Therefore, as before, some adjustment had to be made to the protection scheme in order to achieve the aldol condensation. As shown in FIG. 16 (Scheme XVI), use of 5a instead of 5b gave the expected opening product 91 that could be protected with a smaller silyl group, TMSOTf to furnish the bisprotected diene 93. AD mix as before, and glycol cleavage gave aldehyde 95, that could be reduced and tosylated to provide 96. Following the reaction of FIG. 17 (Scheme XVII) as before with DPS/TBS protection, now substituting TBS/TMS 96 allowed for the production of aldehyde 100. With less hydrophobic steric bulk at the terminus of the side chain (e.g. DPS vs. TBS), the aldol condensation occurred more readily than was the case in the Epothilone A series, FIG. 13 (Scheme XIII). Thus, upon treatment of 100 with 10, aldol adducts could be obtained and silylated in situ as before, becoming immediately ready for cyclization after silica gel chromatography. As shown in FIG. 18 (Scheme XVIII), from this mixture, 104 (or 11 from Scheme I) cyclized in the usual manner to furnish the precursor to Epothilone B, 105. Selective desilylation as before, giving a free alcohol 106, and oxidation gave the ketone 12, and Horner-Emmons Reaction with 24:

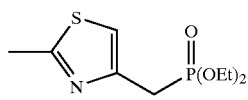

gave e bis-TBS ether of deoxyepothilone B, 107. This is a known compound that has been converted to Epothilone B previously. Nicolaou, K. C., et al., *Total Syntheses of Epothilones A and B via a Macrolactonization-Based Strategy*. J. Am. Chem. Soc., 1997. 119(34): p. 7974–7991.

Figure 19:
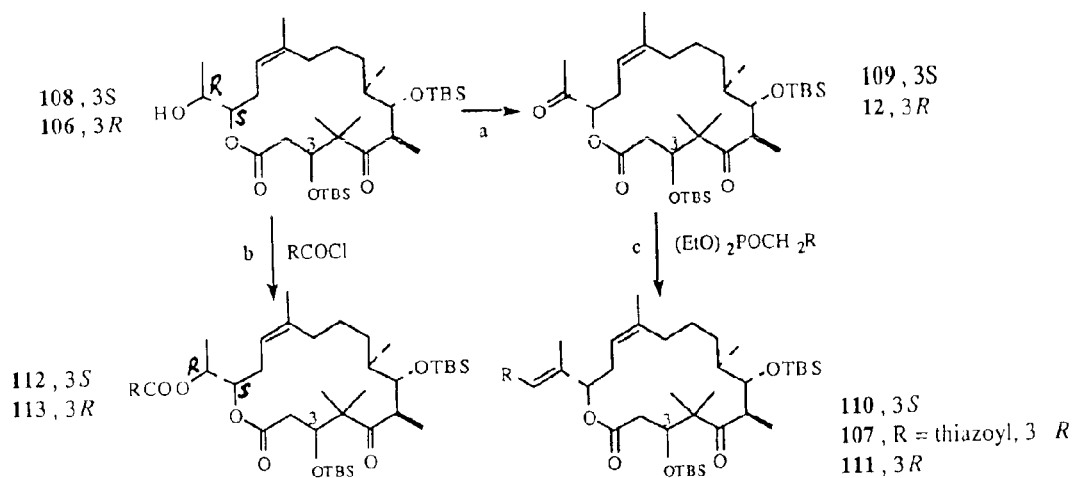
FIG. 19 is a diagram of chemical reaction Scheme XIX according to the present invention.

Clearly, as before in the Epothilone A series, FIG. 14 (Scheme XIV), both alcohol 106 and ketone 12 serve as excellent precursors for the production of analogs as outlined in FIG. 19 (Scheme XIX).

Alcohol 108, as shown in FIG. 19 (Scheme XIX), and stereoisomers thereof, may be represented by the general formula

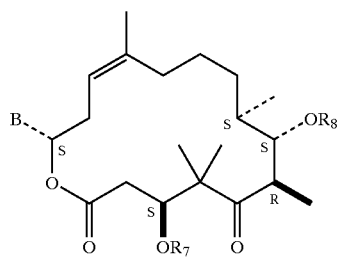

where B is

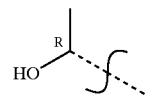

and $R_7$ and $R_8$ are each TBS. In addition, chemical compound 109 and resulting products 110 and 112 and stereoisomers thereof may be represented by the general formula

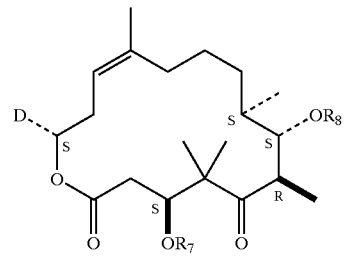

where D is

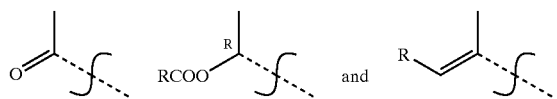

respectively, R is alkyl, aryl, or heterocyclic, and $R_7$ and $R_8$ are each TBS. Again, not only can the 3S series be represented in this chemistry, but so can the 3R diastereomers. A variety of analogs of Epothilone B can be prepared in the side-chain such as esters 112/113 or styrenes or alkenes 110/111.

Figure 20:
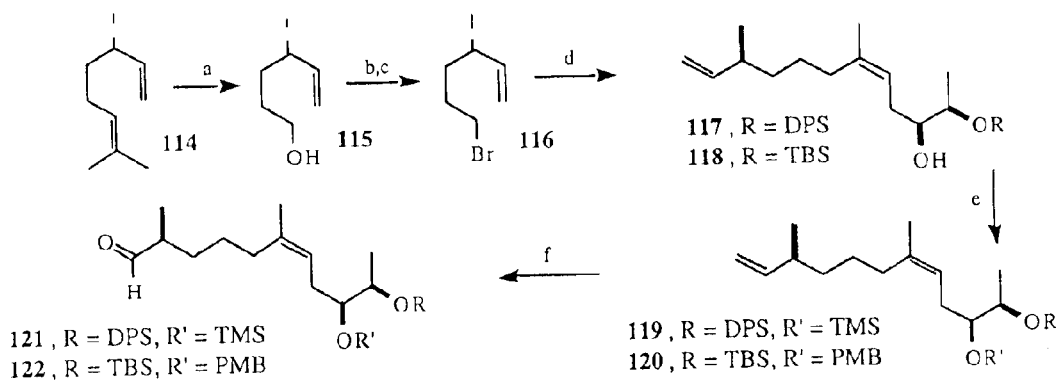
FIG. 20 is a diagram of chemical reaction Scheme XX according to the present invention.

Another alternative to the production of such differentially protected side-chain diols is shown in FIG. 20 (Scheme XX). In this instance, the monoterpene S-dihydromyrcene 114 was employed for its chirality at the methyl position by ozonolytic treatment and reductive workup to furnish degraded alcohol 115. Conversion to the bromide 116 was straightforward, and ensuing Normant reaction as before provided the extensively homologated diol-diene 117 or 118, depending on whether epoxide 5a or 5b was used.

Protection in this case was with a TMS group when DPS was present from 5b, alternatively, when the TBS epoxide was used resulting in 118, then a para-methoxybenzyl (PMB) group was installed to provide 120. Oxidation as before of either terminal alkene with ADmix followed by glycol cleavage with periodate gave the aldehydes 121 or 122. Either of these aldehydes could be used in aldol condensation with acids such as 10 or 56 to provide cyclization precursors to either analogs or Epothilone B.

Figure 21:
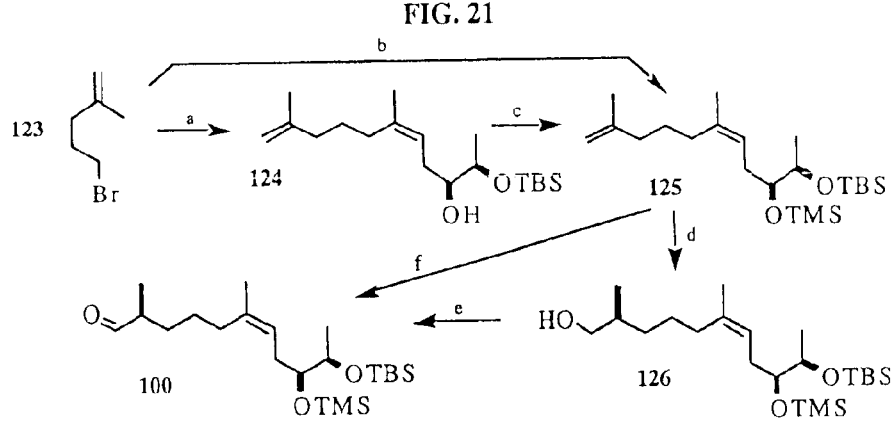
FIG. 21 is a diagram of chemical reaction Scheme XXI according to the present invention.
Figure 22:
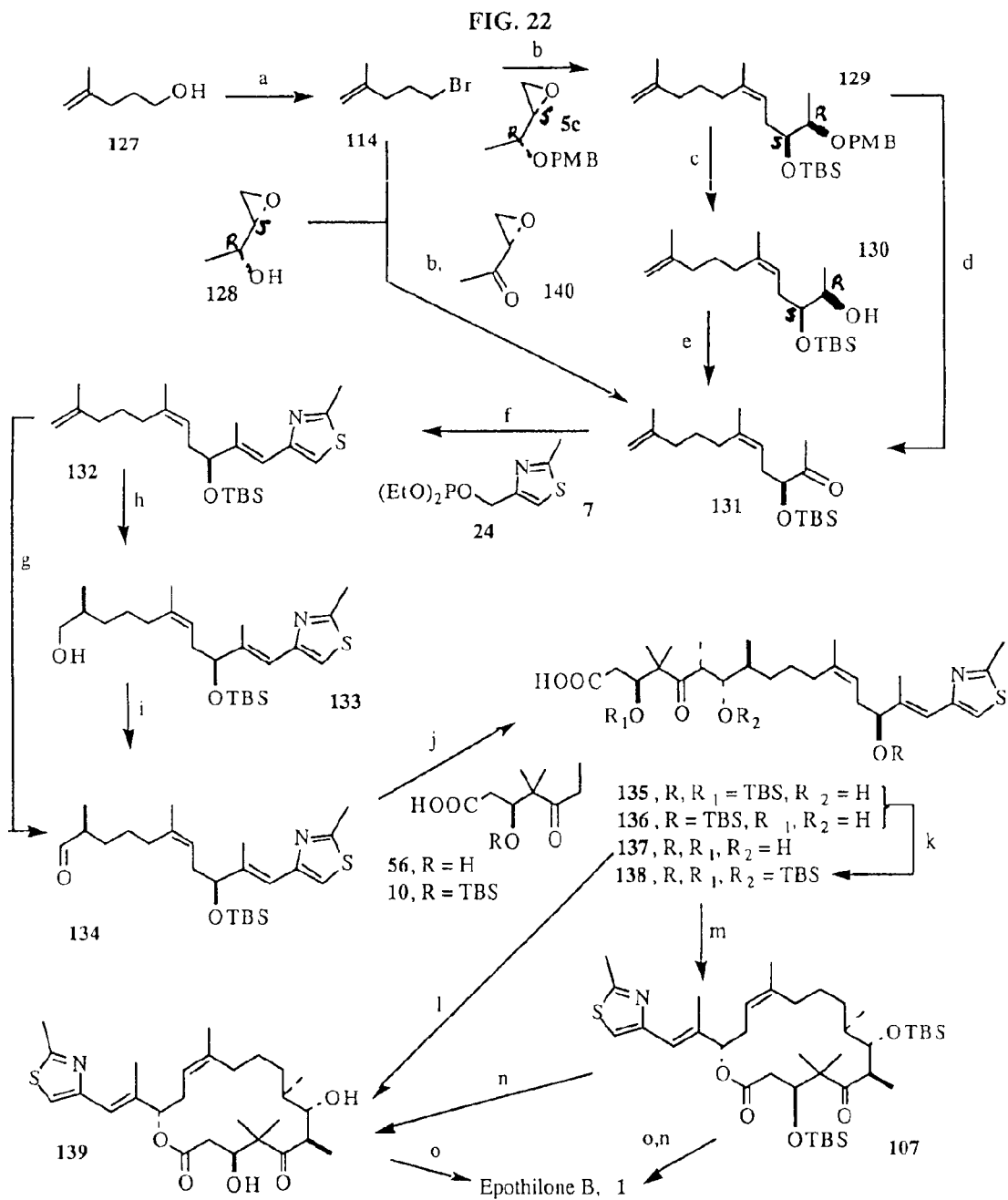
FIG. 22 is a diagram of chemical reaction Scheme XXII according to the present invention.

An additional and intriguing approach to the Epothilones involved the use of 4-methylpentyl bromide in the Normant reaction, shown in FIG. 21 (Scheme XXI). In this case, the usual procedure gave 124 after water workup. However, the intermediate alkoxide could be capped with TMSOTf to furnish the bisprotected compound 125 directly. Alternatively, 124 could be blocked in a separate step with TMSOTf to arrive at the same compound 125. Furthermore, as shown in FIG. 22 (Scheme XXII), a PMB group could be placed on this position in a one pot procedure by adding PMB-Br to the cuprate intermediate, to access the PMB ether 129 directly. Diene 125 (FIG. 21, Scheme XXI) was then hydroborated with bis(isopinocampheyl)borane to give, after oxidative workup with hydrogen peroxide, the S-methyl alcohol 126. Cr(VI) workup (e.g. with PCC) gave the desired aldehyde 100 directly, or separate oxidation of the alcohol 126 afforded 100. Conversions of 100 including its processing to natural product have been discussed (vide supra).

An alternative that incorporates the thiazole ring earlier in the synthesis is shown in FIG. 22 (Scheme XXII). As discussed above, the PMB ether 129 can be formed in a one pot procedure. It can be converted directly into the ketone 131, a direct precursor for chiral hydroboration, or can be removed separately to give alcohol 130 which can be oxidized to the ketone 131. In either event, the ketone 131 undergoes Horner-Emmons reaction to give the triene 132. Now, in similar fashion to before, hydroboration with (Ipc)$_2$BH can be followed up with either $H_2O_2$/NaOH to give alcohol 133, or with Cr(VI) to give aldehyde 134 directly. The alcohol 133 can be oxidized separately to furnish aldehyde as a second route to 134, a known compound whose spectral data was identical to ours. Nicolaou, K. C., et al., *Total Syntheses of Epothilones A and B via a Macrolactonization-Based Strategy.* J. Am. Chem. Soc., 1997. 119(34): p. 7974–7991.

The ensuing aldol condensation of 134 gave products identical to those reported, and subsquent conversions were uneventful. For the precedented reactions, dianion from 10 reacted with known 134 to give either the alcohol 135 (water workup) or the tri-TBS ether 137 (TBSOTf quench, or separate reaction). Either fully silylated acid 138 (literature) or fully desilylated acid 137 (novel) could be cyclized to furnish lactones 107 (literature) or 139 (literature). Their conversion to natural product is known, (Nicolaou, K. C., et al., *Total Syntheses of Epothilones A and B via a Macrolactonization-Based Strategy.* J. Am. Chem. Soc., 1997. 119(34): p. 7974–7991) formally completing the total synthesis of Epothilone B.

A straightforward approach to Epothilone B involves the preparation of ketone 140 (e.g. from alcohol 128), and effecting Horner-Emmons condensation with anion from 24 to furnish elaborated epoxide 141, as shown in FIG. 23 (Scheme XXIII). Normant reaction as before with bromide 123 and propyne, quenching the vinyl cuprate intermediate with 141, and finally, trapping of the alkoxide final intermediate with TMSOTf, gave the triene 143. Aldol condensation with the trianion 56a, and simultaneous chromatography-deprotection provided the triol-acid 59. Cyclization as before gives Deoxyepothilone B 60, which could be epoxidized to afford the natural product 1. Several points worthy of note, this Scheme represents essentially a seven step overall synthesis of Epothilone B. Furthermore, Deoxypothilone B 60 may have superior properties to Epothilone B, thus shortening the route to 6 steps.

As shown in FIG. 24 (Scheme XXIV), another related approach beginning with dihydro-α-myrcene 146 (Rienaecker, R., *.alpha.-Rhodinol and .alpha.-citroneliol from optically active cis-pinane.* Chimia, 1973. 27(2): p. 97–9), involves the opening of epoxide 141 by a vinylalane. This strategy is analogous to the conversion of 81 to 82 in FIG. 15 (Scheme XV). Selective cleavage of the terminal monosubstituted double bond of monoterpene 146 by a suitably hindered, ligated $OsO_4$ species (such as ADmix-α) (Morikawa, K., et al., *Catalytic Asymmetric Dihydroxylation of Tetrasubstituted Olefins.* J. Amer. Chem. Soc., 1993. 115: p. 8463–8464; Andersson, P. G. and K. B. Sharpless, *A Dramatic Ligand Effect on the Relative REactivities of Substituted Alkenes with Osmium Tetroxide.* J. Amer. Chem. Soc., 1993. 115: p. 7047–7048) in the presence of a reoxidant such as $NalO_4$ should lead directly to the aldehyde 147. Schroder, M., *Osmium Tetroxide Cis Hydroxylation of Unsaturated Systems.* Chem. Rev., 1980. 80: p. 187–213. Its reduction to alcohol and protection as a TBS ether should be straightforward in providing 148. Now, ozonolytic cleavage of the disubstituted terminal double bond of 148 should provide ketone 149 in one pot. Introduction of the vinyl iodide by Wittig reaction is precedented, giving the Z-iodide 150. Now, metallation and in situ transmetallation with an alkyl aluminum chloride should give a vinyl alane intermediate, capable of opening epoxide 141 to give an aluminum alkoxide corresponding to 151. In situ silylation of this intermediate should then give 151 in a one pot procedure starting from 150. Finally, desilylative oxidation of the protected alcohol in 151 can be achieved by quinolinium fluorochromate to furnish the requisite aldehyde 152. Chandrasekhar, S., K. P. Mohanty, and M. Takhi, *Practical One-Pot Di-O-silylation and Regioselective Deprotective Oxidation of 1-O-Silyl Ether in 1,2-Diols.* J. Org. Chem., 1997. 62: p. 2628–2629. Now, aldol condensation as before with the trianion of 56a should lead to production of 59, which as before can be converted to Epothilone B.

Figure 25:
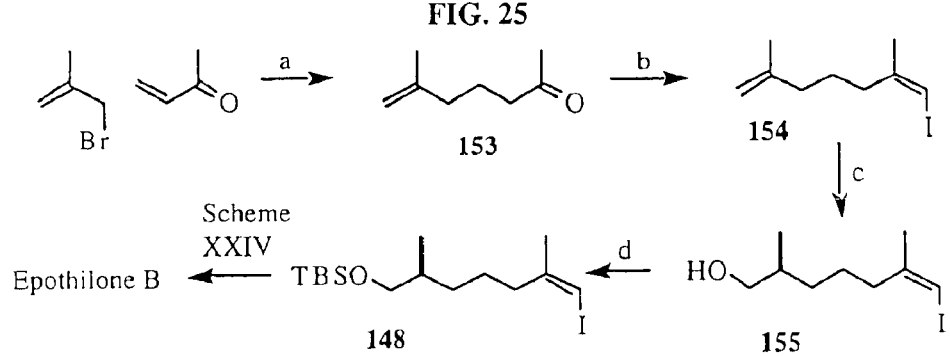
FIG. 25 is a diagram of chemical reaction Scheme XXV according to the present invention.

A viable alternative to the iodide 150 of FIG. 24 (Scheme XXIV) is shown in FIG. 25 (Scheme XXV). The inexpensive industrial chemicals prenyl bromide and MVK can be coupled in one step with Zn/Cu accelerated sonochemically to furnish a well known phermone intermediate, 153. Trehan, I. R., et al., *Synthesis of undecan-3-one; (.+-.) frontalin; (.+-.)-endo-, and (.+-.)-exo-brevicomin under sonochemical aqueous conditions.* Indian J. Chem., Sect. B: Org. Chem. Incl. Med. Chem., 1995. 34B(5): p. 396–8. Wittig reaction of ketone 153 as before should then afford the Z-olefin 154, chiral hydroboration of which is expected to smoothly give the alcohol-iodide 155. Finally, protection provides the common intermediate 150 (148, $R_1$=TBS), also used in Scheme XXIV en route to Epothilone B.

A further scheme for synthesizing epothilones involves an intramolecular aldol condensation instead of the intermolecular approaches outlined above. Generation of the triene 156:

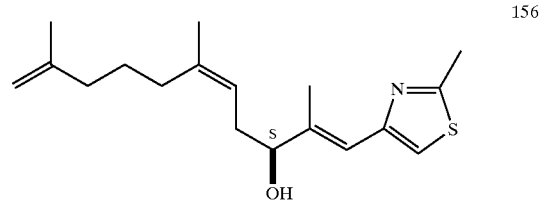

Figure 26A:
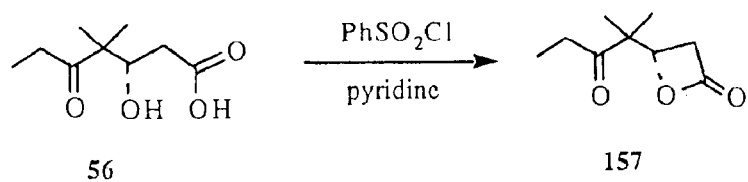
FIG. 26a is a diagram of chemical reaction Scheme XXVIa according to the present invention.

156 is directly analogous to formation of the silylated derivative 132 except that the reaction is worked up with dilute acid instead of a silyl electrophile such as TBSOTf or TBSCl, giving the alcohol 156 instead. The β-lactone 157 (IR: 1832 cm$^{-1}$) was prepared directly from the keto-acid alcohol 56 by treatment with $PhSO_2Cl$ and pyridine as shown in FIG. 26a (Scheme XXVIa), and should serve as a source of acylating agent for construction of the triene-ketoalcohol construct 158, as shown in FIG. 26b (Scheme XXVIb). Thus, treatment of 156 with 157 in the presence of pyridine or other amines, with DMAP as catalyst, should allow for formation of 158 (R=H). Alternatively (step c in Scheme XXVIb), capture of the final alkoxide intermediate leading to 156 with 157, instead of the water workup, should give 158 directly in a one pot procedure. Further, the product 158, either purified, crude, or in situ (step c), can be O-alkylated with a variety of reagents such as benzyloxymethyl chloride (BOMCI), p-methoxybenzyloxymethyl chloride (PMBMCI), 2-trimethylsilylethyloxymethyl chloride (SEMCI) or even 3,4-dimethyoxybenzyl chloride (DMBCI), bromide, or trichloroamidate (Ar—CH$_2$O—C(CCl$_3$)=NH). It can also be silylated with any usual silyl reagent such as TMS, TBS, TIPS, etc.

With protected 158 in hand, hydroboration as before with (Ipc)$_2$BH can be followed by conventional workup to afford alcohol 159, or the intermediate borane can be directly oxidized with Cr(VI) to afford the aldehyde 160. Of course, the alcohol 159 can be oxidized under Swern conditions to furnish 160 as well. Now, selective enolborane formation with a dialkylboron triflate can be effected to give the transient boron enolate 160a which should undergo intramolecular aldol reaction to afford the cyclized lactone 161. Finally, removal of the protecting group with appropriate conditions, e.g., when R=PMBM, use of DDQ readily leads to cleavage to deoxyepothilone B, 139.

Figure 27:
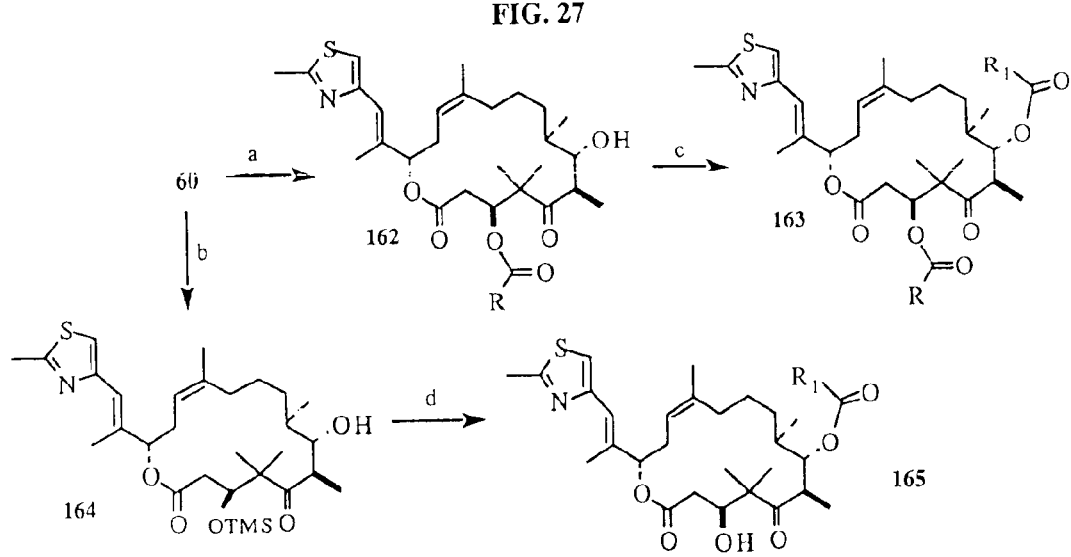
FIG. 27 is a diagram of chemical reaction Scheme XXVII according to the present invention.

A variety of analogs of 60 can be prepared as outlined in FIG. 27 (Scheme XXVII), taking advantage of the greater steric accessibility of the C-3 hydroxyl group. In one case, direct acylation of C-3 provides 162, leaving only one additional hydroxyl group Chemical compound 162, and stereoisomers thereof, may also be represented by the general formula

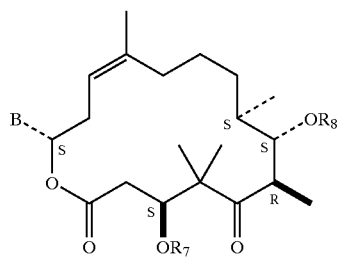

where B is

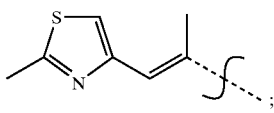

R$_7$ is

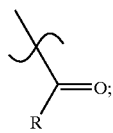

and R$_8$ is H.

Chemical compound 162 can be acylated under more forced considtions to give 163. Chemical compound 163, and stereoisomers thereof, can be generally represented by the formula

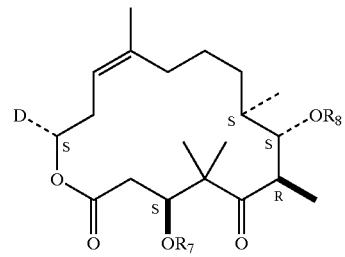

and stereoisomers thereof, where D is

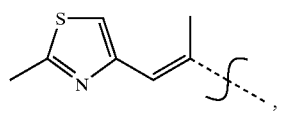

and R$_7$ is

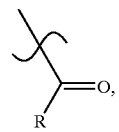

R$_8$ is

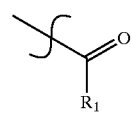

Alternatively, silylation of C-3 furnishes 164, and forced acylation then gives 165 after silica gel purification to simultaneously remove the TMS group from C-3. In these reactions, R=alkyl, aryl, alkyl-aryl, OR, NRR', SR, and so on. In addition, the X group in RCOX denotes the use of active esters to effect these transformations as well as acid chlorides, and in some cases may suggest the use of isocyanates, thioisocyanates, etc.

Figure 28:
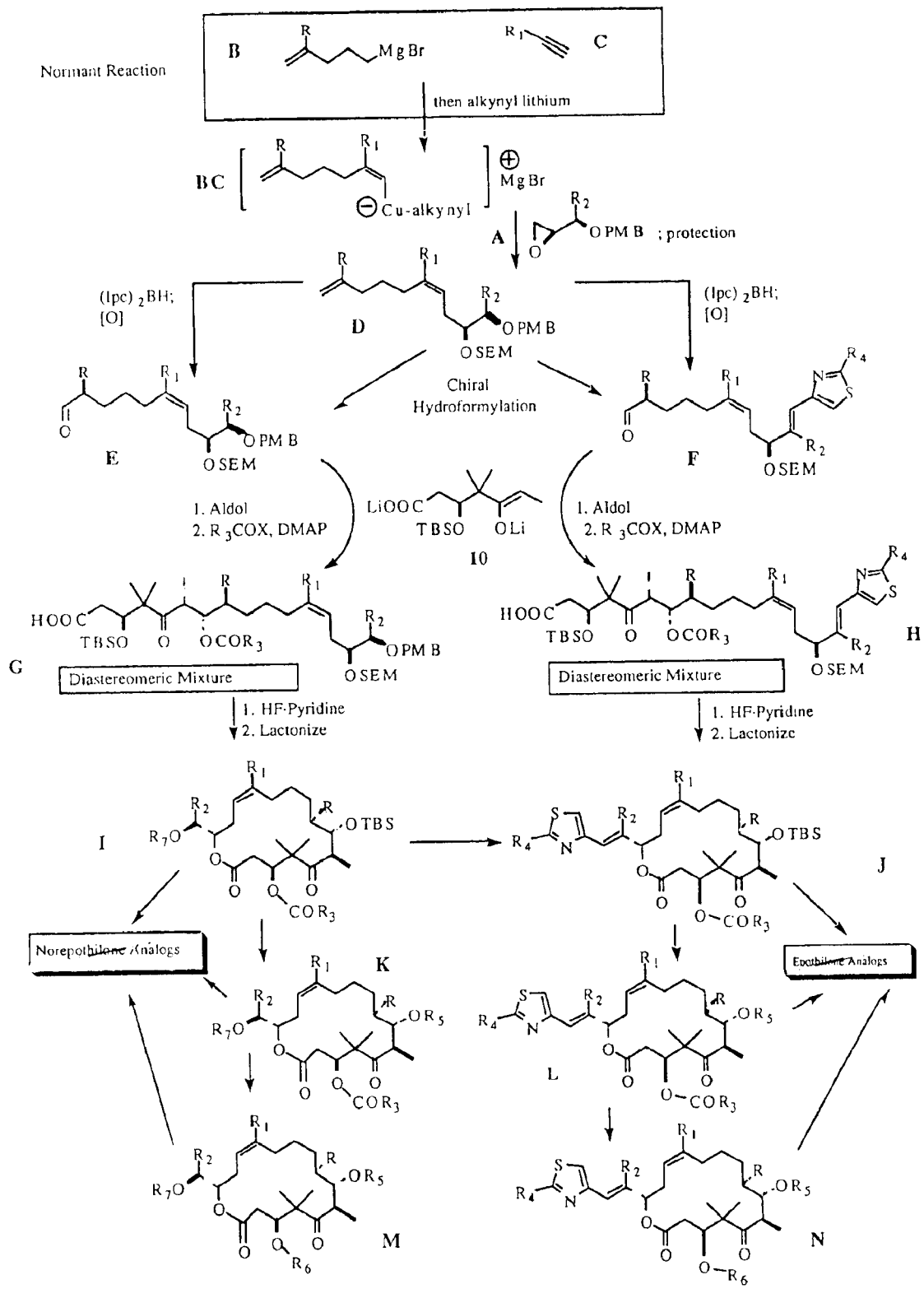
FIG. 28 is a diagram of chemical reaction Scheme XXVIII according to the present invention.

Another approach to producing analogs of epothilones was outlined in FIG. 28 (Scheme XXVIII). Here, a generally applicable synthetic route to epothilones and their analogs is shown. The process entails the novel Normant reaction of a Grignard reagent B (where R can be H, Me or a variety of aryl, alkyl or other moieties) with a terminal alkyne C (where R can be H, Me or a variety of aryl, alkyl or other moieties); the resulting intermediate is then treated with an alkynyl lithium to produce an alkenyl-mixed cuprate BC which is quenched by a protected 1,2-epoxy-3-hydroxy species A (where R can be H, Me or a variety of aryl, alkyl or other moieties). The intermediate or crude product is then treated with an alcohol protecting group reagent (such as a SEM chloride, i.e. a 2-silylethoxymethoxy chloride), producing in a single operation, the diene D.

The diene D can either be hydroformylated under chiral conditions, or hydroborated using bis(isopinocampheyl) borane to furnish ultimately the aldehydes E or F. In the case of F, the PMB protecting group is removed, the alcohol is oxidized, and the ketone made to undergo Horner-Emmons reaction to install the vinylic aromatic species, such as F.

With either aldehyde E or F, aldol condensation of the dianion prepared from 10 followed by protection of the resulting aldol derived, β-hydroxy group as an acyl derivative (e.g. the TROC group; trichloroethoxycarbonyl or Cl$_3$CCH$_2$OCO—; or for example, a hexenoyl moiety; e.g. CH$_2$=CH(CH$_2$)$_3$CO—), leads to formation of the diastereomeric aldol adducts G or H. In the case of H, simple cleavage of the C-15 protecting group (when SEM, use a fluoride source such as HF.pyridine) can be achieved. After lactonization, the diprotected lactone J is obtained. Removal of the remaining silicon protecting group gives an epothilone D analog that can be epoxidized to give an epothilone B analog. Alternatively, norepothilone analogs that mirror the H manifold, I, can be obtained by derivatization of the C-16 hydroxyl group with R$_7$. As before, the silicon group can be removed to give a norepothilone D analog, epoxidation of which would give a norepothilone B analog.

In any case, R$_1$ can be H for the epothilone A series, or another group to provide an entirely new species.

After removal of the TBS group from I or J, an additional acyl group can be installed to give K or L. When the COR$_3$ group is a procecting group like a TROC, it can be removed from K or L to give M or N. These chemistries allow for the hydroxyl groups to be derivatized in any pattern desirable to achieve the required pharmacological properties of the materials. For example, in the case of N, when R$_4$, R$_2$, R$_1$, R=Me, R$_3$=H, and R$_6$=CH$_2$=CH(CH$_2$)$_3$CO—, an analog of epothilone is produced by total synthesis, but never via the natural product. The side-chain double bond can be selectively cleaved to allow formation of an aldehyde that can be used as a tether to solubilizing groups, etc.

As above, protecting groups can be manipulated to arrive at structures such as M with a variety of substituents. These substituents can be optimized by combinatorial or parallel synthesis methods to provide norepothilone analogs optimized for high anticancer potency and minimized toxicity. Additional approaches to targeting these analogs could involve tethering to carrier molecules.

In more detail, a specific example is provided in FIG. 29 (Scheme XXIX). The Normant product 166 was protected as SEM ether to give 167. The PMB group was deprotected by using DDQ and the resulting alcohol was oxidized to the corresponding ketone 169 which was then reacted with Horner-Emmons reagent 24 to furnish triene 170. Hydroboration of compound 170 with bis(isopinocampheyl)borane and oxidative work up with hydrogen peroxide gave the S-methyl alcohol 171. Oxidation of alcohol 171 afforded aldehyde 172. The ensuing aldol condensation of 172 with ketoacid 10 gave products 173a and 173b in 1:1 ratio. Hydroxy acids are protected as TROC esters and SEM group was deprotected and subsequent macrolactonization afforded 174. Removal of protecting groups gave desoxyepothilone B.

Figure 30:
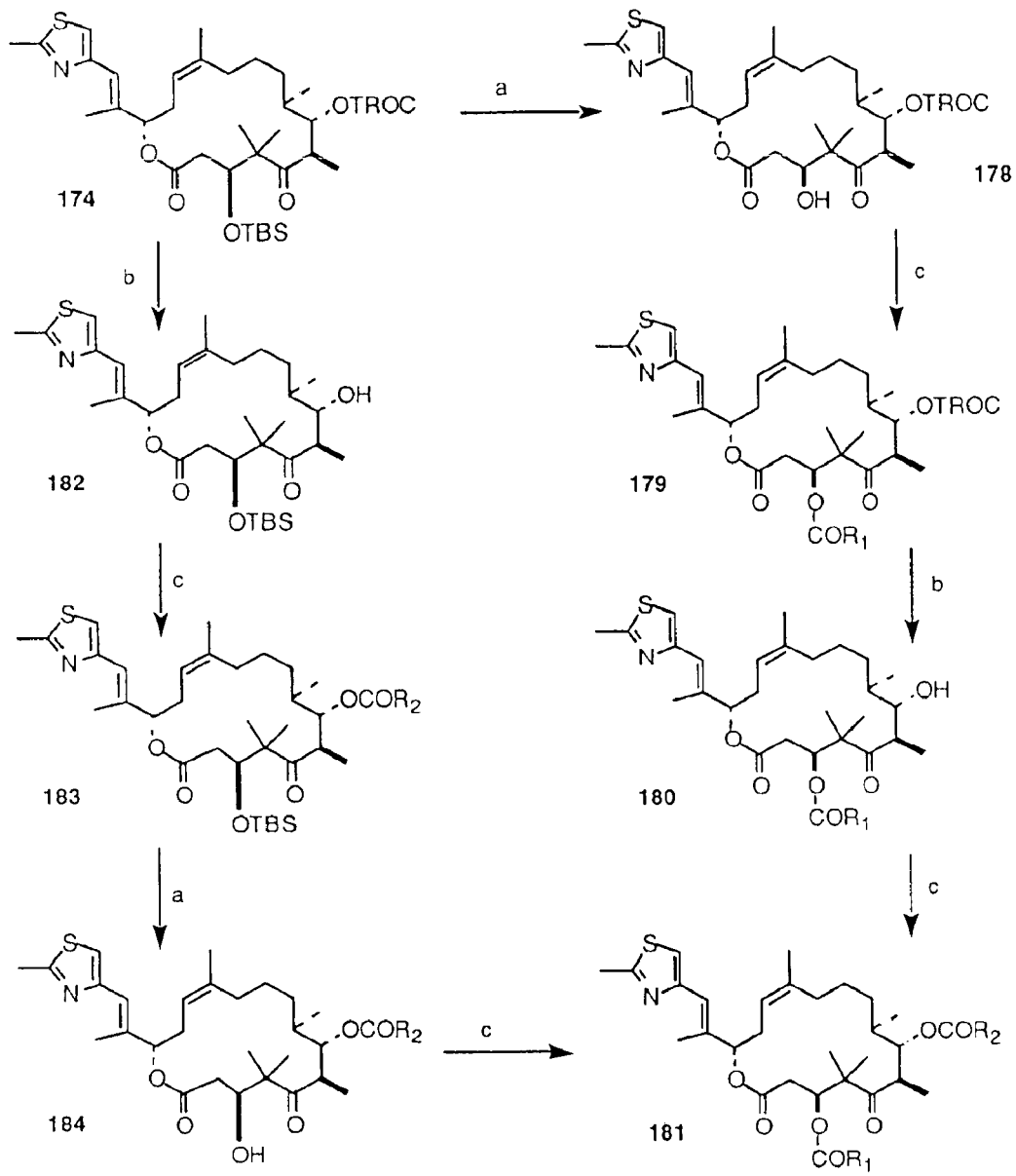
FIG. 30 is a diagram of chemical reaction Scheme XXX according to the present invention.

The particulars of FIG. 29 (Scheme XXIX) allow for entry to previous Scheme XXVII (FIG. 27), in which 178 is similar to 165. Similarly, 174 can lead to the homolog of 164 in which the Si group is a TBS instead of a TMS. The TROC 165 can be acylated at C-3, and the TROC removed to give 162 and thereby 163. This is shown in FIG. 30 (Scheme XXX). An acyl group is installed at C3 of 178 to give 179. The TROC can be removed to give 180. Finally, another acyl group can be added to C7 to give a diacyl derivative 181, itself available from the alternate manifold culminating in 184. Along these lines, the TROC can be removed to afford 182 and the C7 hydroxyl acylated to give 183. Removal of the TBS group should give 184.

With continued reference to FIG. 29 (Scheme XXIX), chemical compounds 178 to 181, and stereoisomers thereof can also be represented as the following general formulas:

178

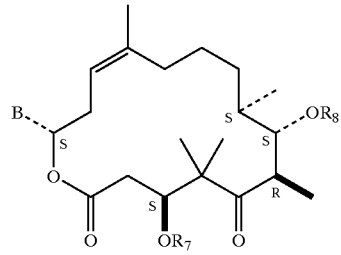

where B is

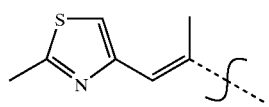

and R$_7$ is H and R$_8$ is TROC.

179

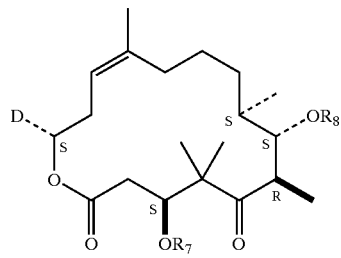

where D is

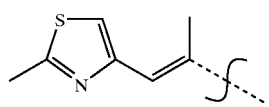

and R$_7$ is COR$_1$ and R$_8$ is TROC.

180

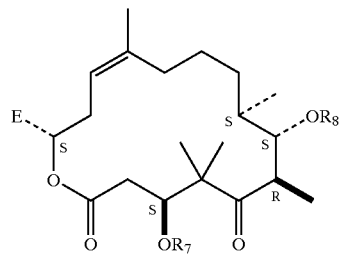

where E is

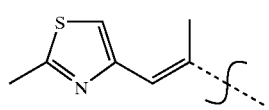

and $R_7$ is $COR_1$ and $R_8$ is H.

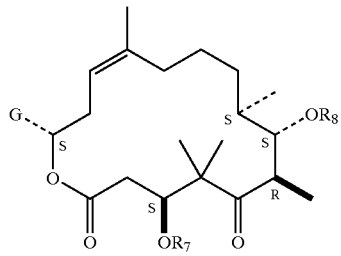

181 where G is

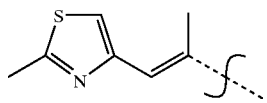

and $R_7$ is $COR_1$ and $R_8$ is $COR_2$.

Similarly, chemical compounds 182–184, and stereoisomers thereof, can be represented as the following general formulas:

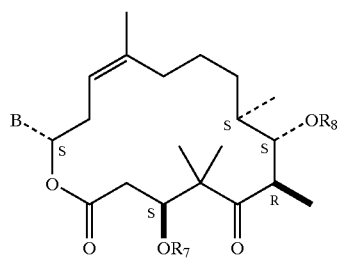

182 where B is

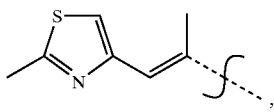

$R_7$ is TBS, and $R_8$ is H.

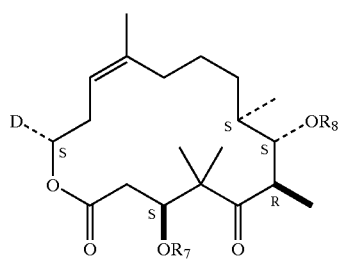

183 where D is

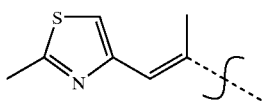

$R_7$ is TBS, and $R_8$ is $COR_2$.

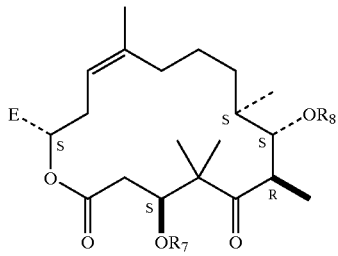

184 where E is

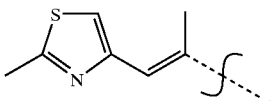

$R_7$ is H and $R_8$ is $COR_2$.

Figure 31:
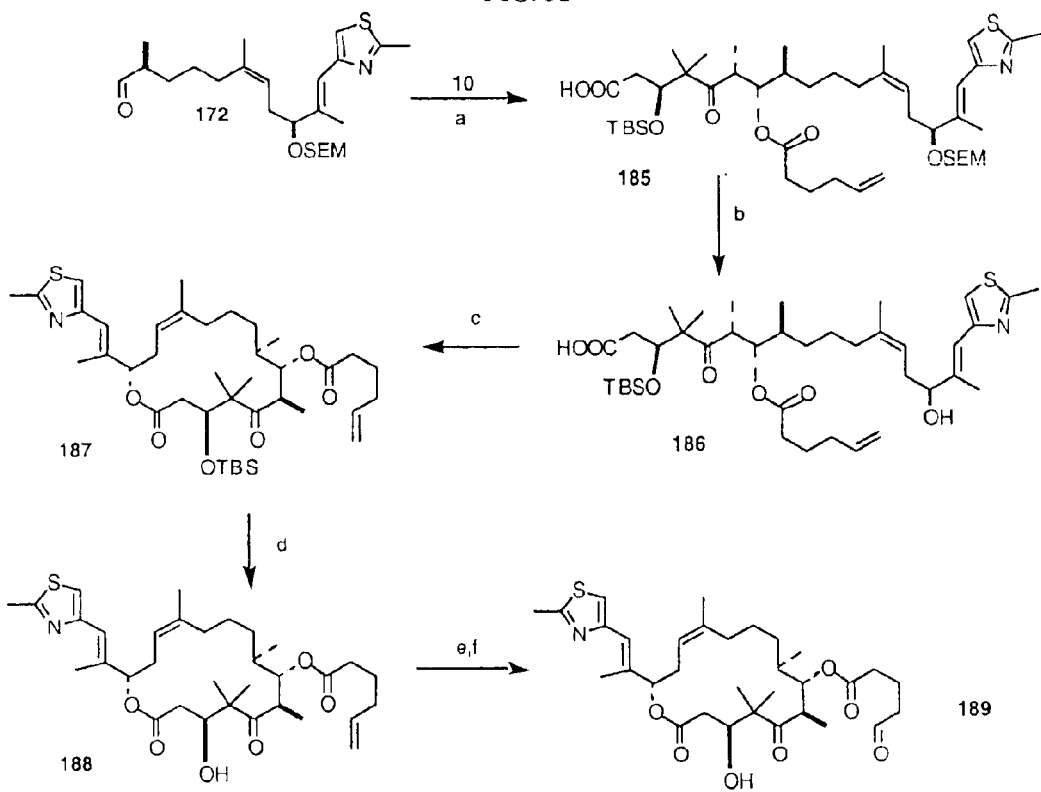
FIG. 31 is a diagram of chemical reaction Scheme XXXI according to the present invention.

A specific example is afforded in FIG. 31 (Scheme XXXI), in which a hexenyl moiety is pendant to the C7 hydroxyl group. In this case, after the aldol reaction, the intermediate is quenched with hex-5-enoic acid active ester or the acid chloride to give 185. This is similar to the TROC derivitization giving 173. As before, selective SEM removal affords 186. After lactonization, 187 is formed, from which the TBS can be removed with HF.pyridine to give 188. Finally, the side chain olefin (least hindered) can be hydroxylated and cleaved affording the aldehyde 189. Alternatively; a hexanoic acid ester derivative may instead be used, e.g. by replacing $CH_2=CH(CH_2)_3COCl$ in step a of FIG. 31 with $CH_3(CH_2)_4COCl$ and leaving out steps e and f. The use of other alkanoic or alkenoic acid esters, substituted and unsubstituted, is also contemplated.

A further route to the epothilones is demonstrated with respect to FIGS. 32 through 37. The Z olefin, an essential feature for the synthesis of epothilone B, as reported in the literature, was prepared either by classical Wittig olefination methods or ring closing olefin metathesis approaches. Herein we report a unique and stereoselective method to generate the trisubstituted Z olefin geometry by modification of a classical Normant alkyne cupration and electrophile trap.

Figure 32:
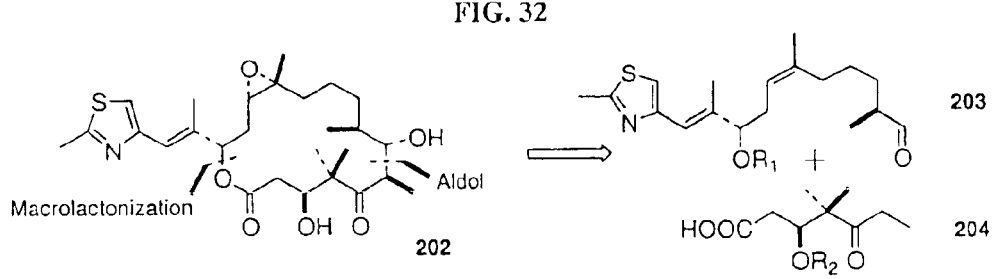
FIG. 32 is a diagram of chemical reaction Scheme XXXII according to the present invention.
Figure 33:
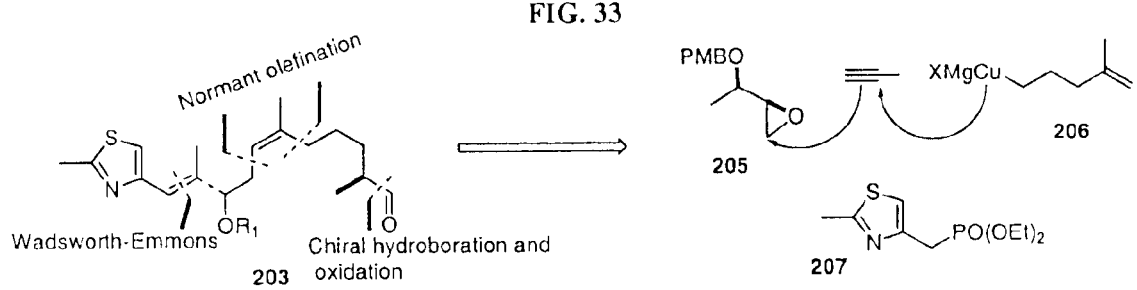
FIG. 33 is a diagram of chemical reaction Scheme XXXIII according to the present invention.

Retrosynthetic disconnection of epothilone B indicated to us that synthons 203 and 204 could serve as key intermediates, which could be coupled together via a double-diastereoselective aldol condensation, as shown in FIG. 32 (Scheme XXXII) and macrolactonization to furnish the target framework. The synthesis of aldehyde unit 203, the northern hemisphere of epothilone B, is based on the retrosynthetic strategy indicated in FIG. 33 (Scheme XXXIII). Thus, ring opening of epoxide 205 by the Normant-derived vinyl cuprate 206, should lead to an alcohol whose oxidation to ketone could be followed by a Wadsworth-Emmons olefination reaction. Finally, the α-methyl carboxaldehyde could be generated by a chiral hydroboration-oxidation sequence to provide 203.

Figure 34:
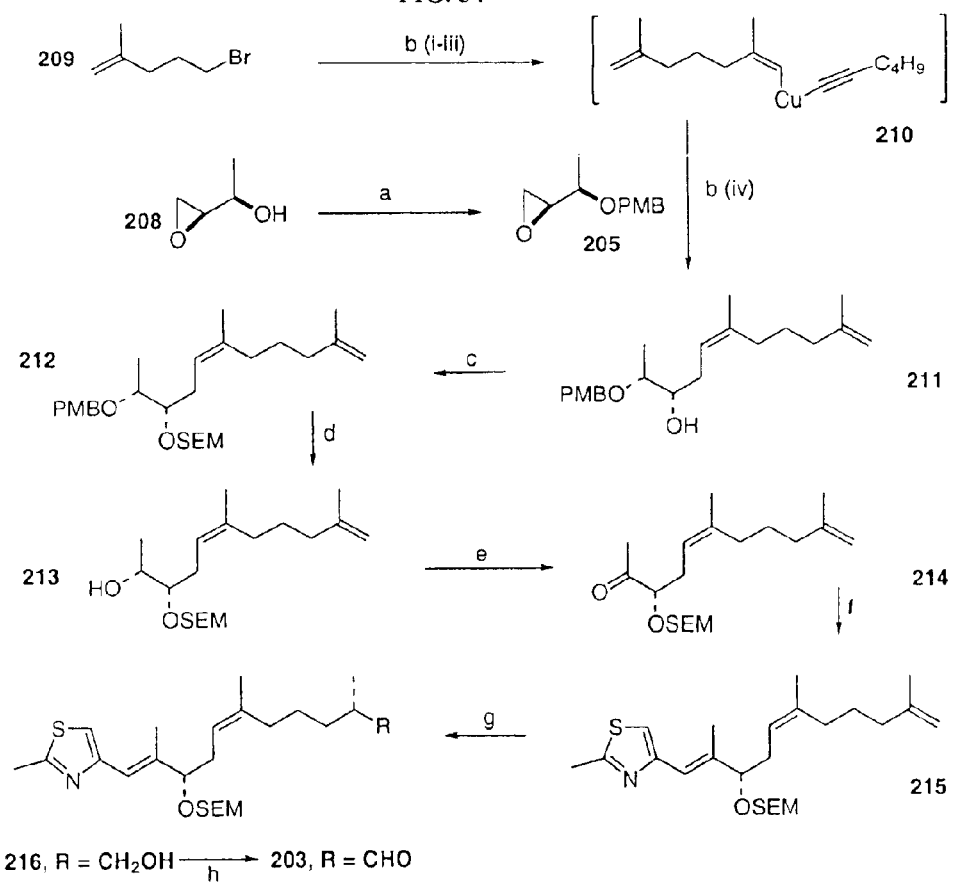
FIG. 34 is a diagram of chemical reaction Scheme XXXIV according to the present invention.

The synthesis of fragment 203 was commenced by protection of (2S, 3R)-1,2-epoxy-3-butanol 208 as its p-methoxybenzyl (PMB) ether, as shown in FIG. 34 (Scheme XXXIV). This was achieved by treating compound 208 with sodium hydride and PMB bromide to give 205 in 85% yield. Hetakeyama, S.; sakurai, K.; Takano, S. *Heterocycles*, 1986, 24, 633–637. The Normant coupling reaction with epoxide 205 was performed conveniently as follows. Normant, J. F. *Synthesis* 1972, 63–80; Marfat, M.; McGuirk, P.; R.; Helquist, P. J. *Org. Chem.* 1979, 44, 3888–3092.

After forming the Grignard reagent from the reported bromide 209, admission of CuBr-DMS complex and stirring for several hours at low temperature led to a black solution of cuprate reagent. Condensation of propyne (g) into the cuprate solution at low temperature was followed by addition of lithiohexyne. Alkylation of the resultant vinyl cuprate 210 was accomplished over the course of one day at −25° C. following addition of epoxide 205. Chromatography of the crude product provided the diastereomerically pure Z-alkene 211 in 76% yield. The alcohol moiety of alkenol 211 was derivatized with SEMCI and DIPEA to provide a SEM-ether, 212. Removal of the PMB ether of 212 with DDQ left the SEM-ether intact to give the alcohol 213. Oxidation of 213 was then effected under Swern conditions to afford the methyl ketone 214 in 85% yield. Wadsworth-Emmons olefination of ketone 214 with the known phosphonate 207 led to the production of diastereomerically clean triene 215 in 72% yield. Schnizer, D.; Limberg, A.; Bohm, O. M. *Chem. Eur. J.* 1996, 11, 1477–1482. Finally, diastereoselective hydroboration of the triene 215 using (i-PC)$_2$BH (Wifely, G.; Ayyangar, N. R.; Takashi Munekata.; Brown, H. C. *J. Am. Chem. Soc.* 1964, 86, 1076–1078; Brown, H. C.; Joshi, N. N. *J. Am. Chem. Soc.* 1988, 53, 4059–4061) followed by oxidative work-up and subsequent Swern oxidation of the resulting alcohol 216, furnished the enantiomerically pure aldehyde 203 in 92% yield.

Figure 35:
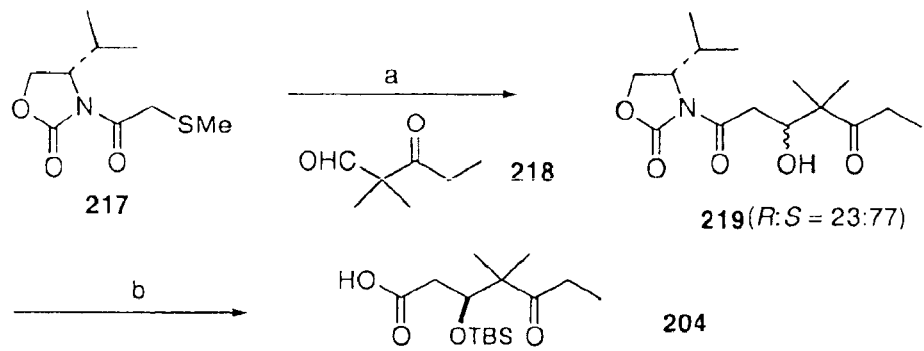
FIG. 35 is a diagram of chemical reaction Scheme XXXV according to the present invention.

For the aldol condensation shown in FIG. 32 (Scheme XXXII), the silyl protected keto-acid 204 was required. This acid could be prepared as reported in our work via an Evans enantioselective aldol condensation. Panicker, B.; Karle, J. M.; Avery, M. A. *Tetrahedron,* 2000, 56,7859–7868 and references therein. As shown in FIG. 35 (Scheme XXXV), the dibutylboron enolate of the reported oxazolidinone 217 reacted with keto-aldehyde 218 to give an α-thiomethyl amide aldol intermediate. Desulfuration was readily accomplished using Raney Ni, providing the corresponding R:S aldol adducts 219 in a 23:77 ratio, respectively (70% yield). After silylation with TBDMSOTf and removal of auxiliary, we obtained 204 in good overall yield.

Figure 36:
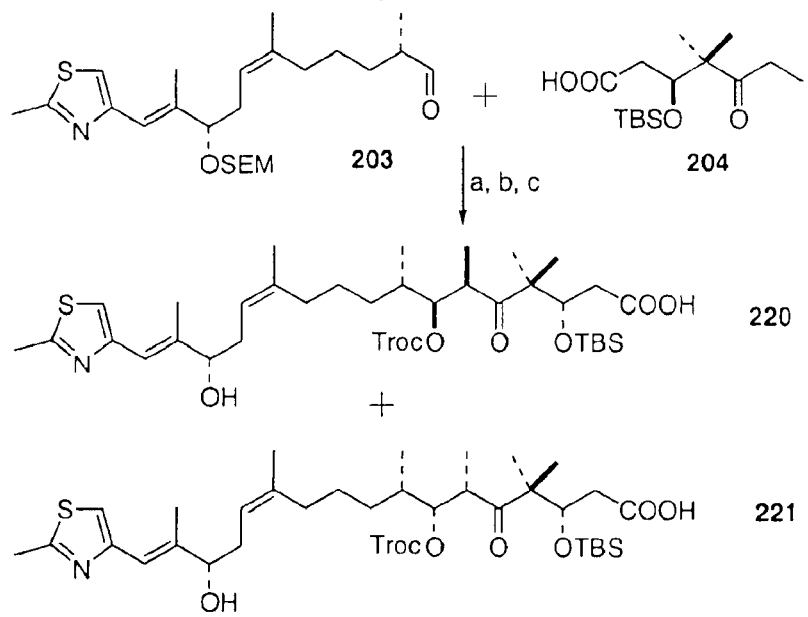
FIG. 36 is a diagram of chemical reaction Scheme XXXVI according to the present invention.

The optimum conditions for the aldol condensation of keto-acid 204 with aldehyde 203 required generation of the dilithio derivative of 204 with LDA (−78° C. to −40° C.) followed by metal exchange with anhydrous ZnCl$_2$ at −78° C. Nicolaou, K. C.; Winssinger, N.; Pastor, J.; Ninkovic, F.; Sarabia, F.; He, Y.; Vourloumis, D.; Yang, Z.; Li, T.; Giannakaku, P.; Hamel, E. *Nature,* 1997, 387, 268–272. Thereupon, reaction of aldehyde 203 with the transmetallated enolate of 204 led to formation of polar adducts best handled as shown in FIG. 36 (Scheme XXXVI). Treatment of the aldol mixture with 1.2 equivalents of TBSCl and excess TrocCl in pyridine furnished a mixture of fully protected products. Upon exposure to trifluoroacetic acid at −20° C., deprotection of the SEM ether with simultaneous deprotection of TBS esters occurred. At this stage the aldol product mixture could be conveniently separated from the unreacted keto-acid 204 by flash column chromatography giving adducts 220 and 221 in a 2:1 diastereomeric ratio.

Figure 37:
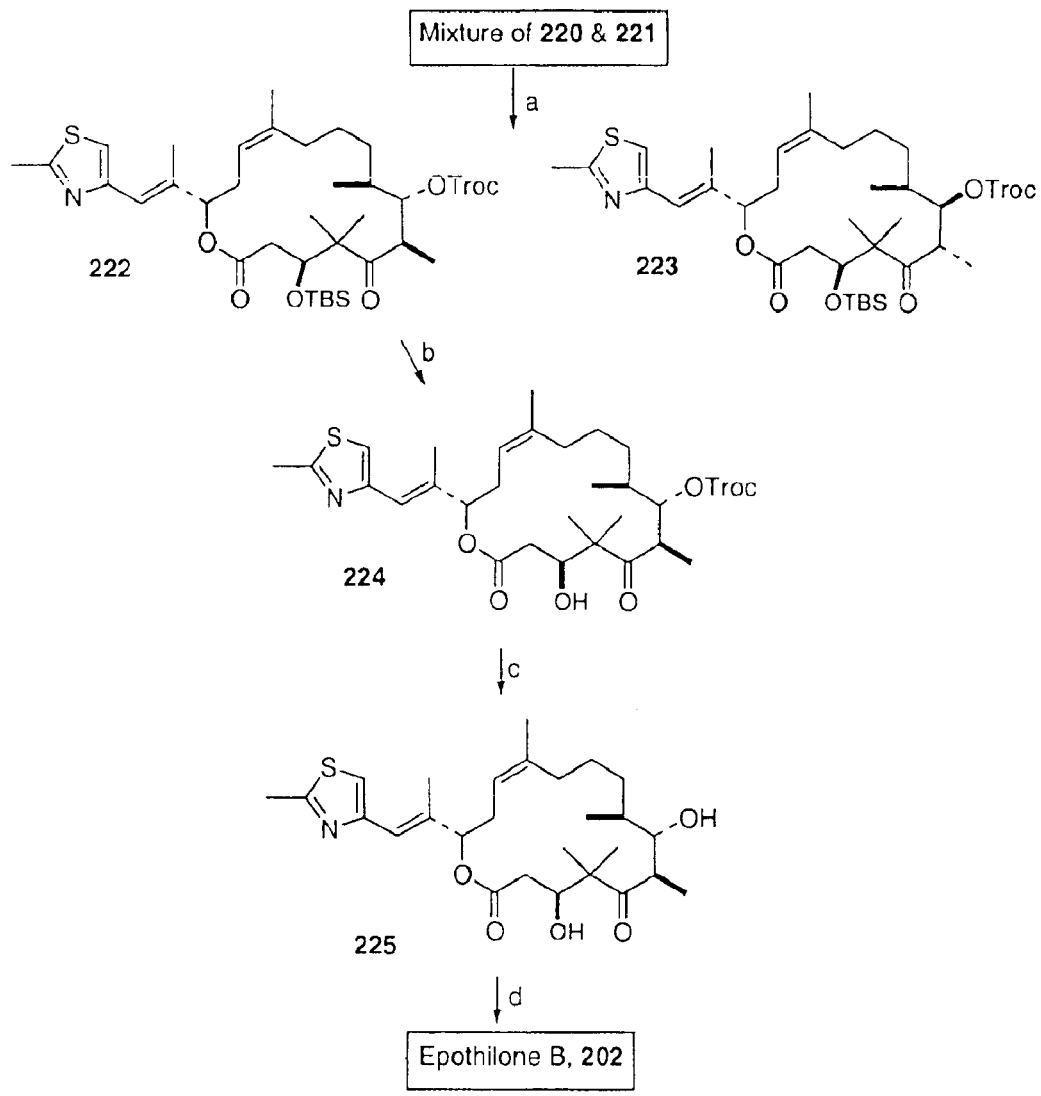
FIG. 37 is a diagram of chemical reaction Scheme XXXVII according to the present invention.

The mixture of hydroxy acids was then subjected to macrolactonization using the Yamaguchi method (Inanaga, J.; Hirata, K.; Saeki, H.; Katsuki, T.; Yamaguchi, M. *Bull. Chem. Soc. Jpn.* 1979, 52, 1989) to obtain the corresponding lactones as shown in FIG. 37 (Scheme XXXVII). The two lactones 222 and 223 were readily separated by flash column chromatography and 222 was characterized by conversion to natural product. Selective deprotection of the TBS group from 222 using HF-Py followed by chromatographic purification gave the desired Troc-alcohol 224. Removal of the Troc group was effected using Zn and aq. NH$_4$Cl in MeOH to provide the diol 225, epothilone D. Yang, D.; Wong, M.-K.; Yip, Y.-C.; *J. Org. Chem.* 1995, 60, 3887–3889. Finally, treatment of 225 with methyl (trifluoromethyl)-dioxirane led cleanly to epothilone B 202, whose properties were identical to reported spectral and physical data for the natural product. For synthetic Epothilone B 202, $[\alpha]^{20}_D = -31°$ (c 0.25, CHCl$_3$); Reported rotation (Meng, D.; Bertinato, P.; Balog, A.; Su, D.-S.; Kamenecka, T.; Sorensen, E.; Danishefsky, S. J. *J. Am. Chem. Soc.* 1997, 119, 100073–10092) for synthetic Epothilone B 2, $[\alpha]^{25}_D = -31°$ (c 0.045, CHCl$_3$).

Epothilone B 202, and stereoisomers thereof, may be represented by the following general formula

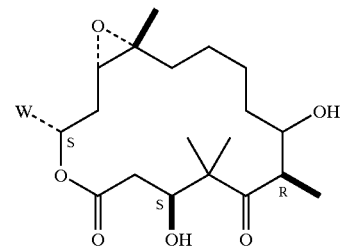

where W is

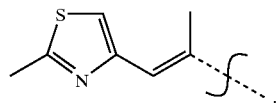

While specific examples have been provided herein of particular chemical compounds formed by specific reaction steps, It should be appreciated that the present Invention broadly contemplates numerous variations In the chemical compounds and in the reactants used in any given reaction step, thereby to form various chemical compounds having such substituents as might be desired, as understood by the ordinarily skilled person. For example, the present invention contemplates variations in the protecting groups, such as the use of other types and classes of protecting groups as generally understood by the ordinarily skilled organic chemist. Other variations contemplated by the present invention include variations in the ester moieties at the C-3 and C-7 positions, for example, as well as variations in the sidechain structures and substituents thereof. For example, the present invention broadly contemplates, without limitation, chemi cal compounds (and stereoisomers thereof) of the following formulas, among others:
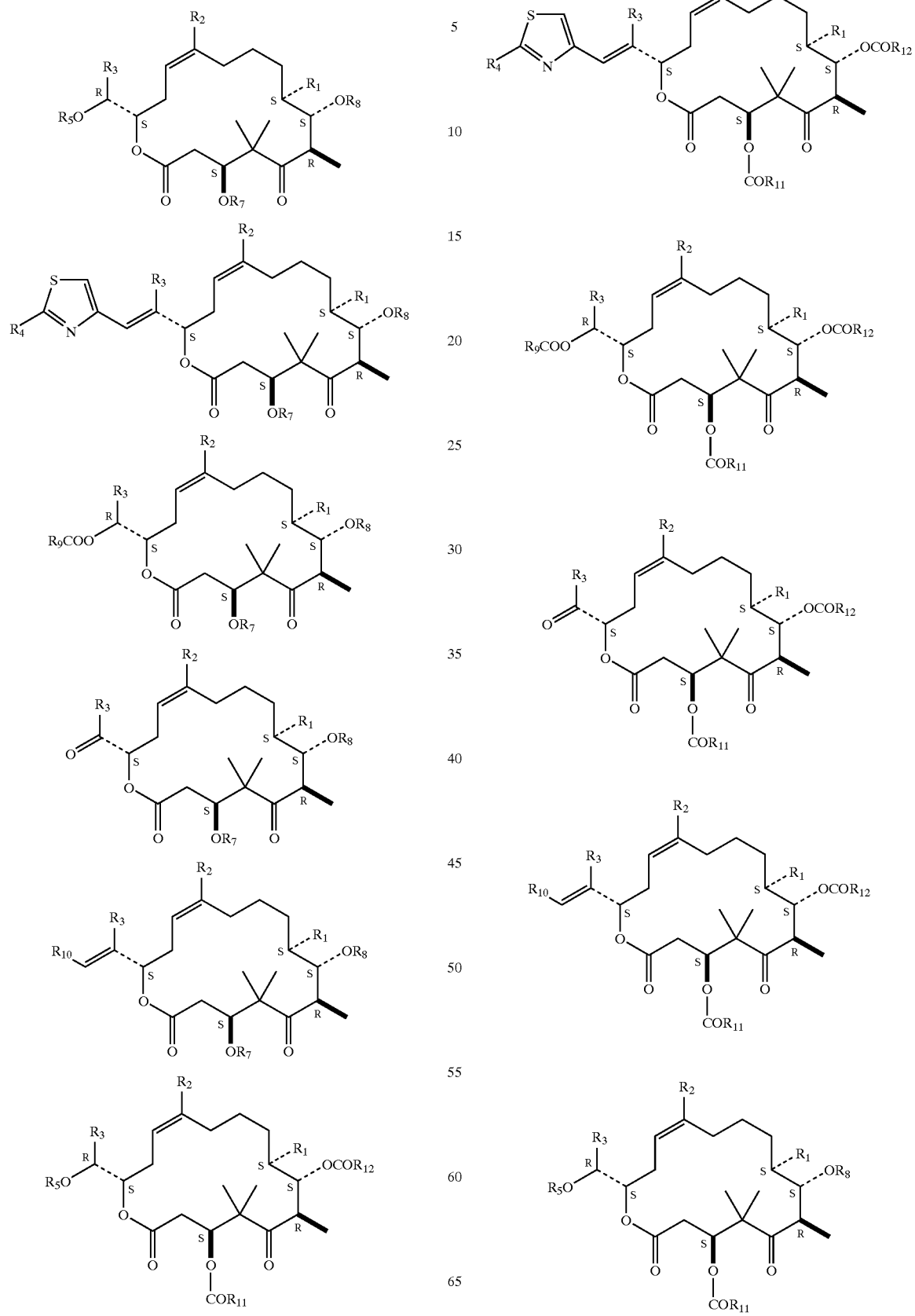

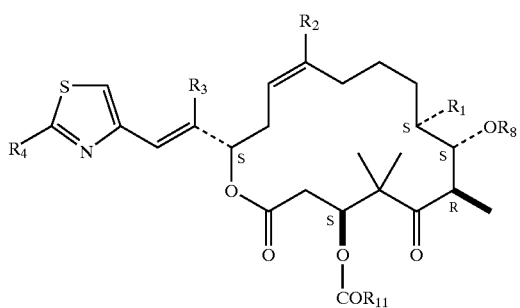
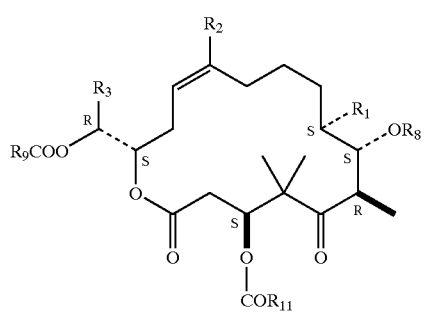
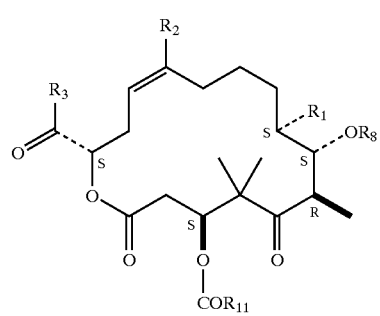
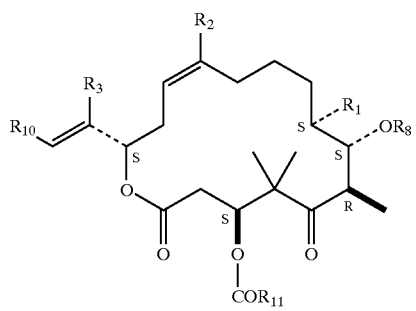
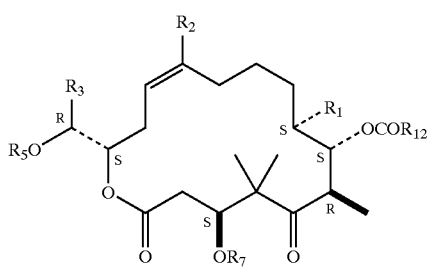
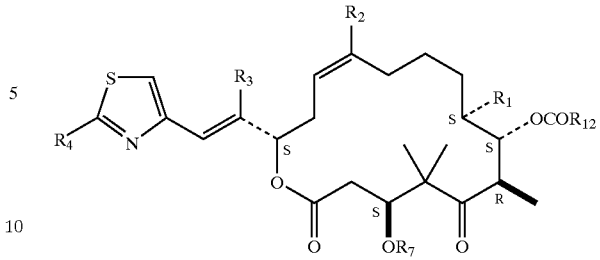
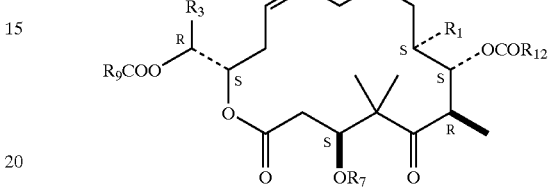
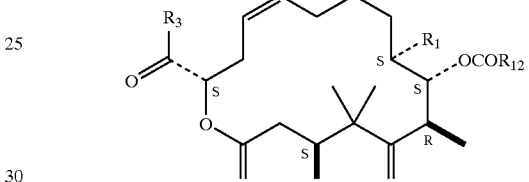
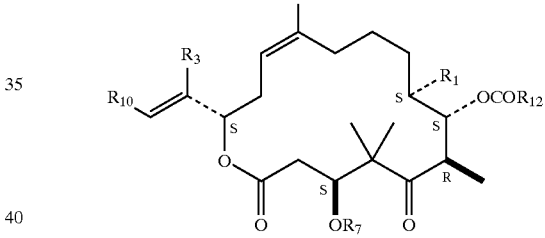

wherein $R_1$ through $R_{12}$ may be various substituents selected from the numerous varieties of known possible substituents in the art. For example, $R_1$, $R_2$, $R_3$, $R_4$, $R_9$ and $R_{10}$ may be each selected from H, alkyl, alkenyl, alkynyl, aryl, substituted alkyl, substituted alkenyl, substituted alkynyl, substituted aryl, cycloalkyl, heterocyclo; $R_5$, $R_6$, $R_7$ and $R_8$ may be selected from H and a protecting group; and $R_{11}$ and $R_{12}$ may be each selected from alkyl, alkenyl, alkynyl, aryl, alkyl-aryl, alkyloxy, aryloxy, cycloalkyl, heterocyclo, amino, sulfo, and substitutions thereof. It is contemplated that $R_{11}$, and $R_{12}$ may be respectively selected such that the 3 and 7 positions may form various desired esters, and in particular esters of alkanoic and alkenoic acids, such as hexanoic and hexenoic acids (e.g., $R_{11}$, or $R_{12}$ may be —$(CH_2)_xCH_3$, —$(CH_2)_yCH=CH_2$, and the like where x and y are appropriate integers, such as 3 or 4. These substituents may be further substituted as understood in the art. It should further be understood that various appropriate intermediate compounds may thus be formed, such as precursors and compounds for use in, or formed during, the aldol condensation and macrolactonization steps described above, or in the various other conversion steps described herein.

Collectively, the above-identified chemical compounds can be represented by the general formula

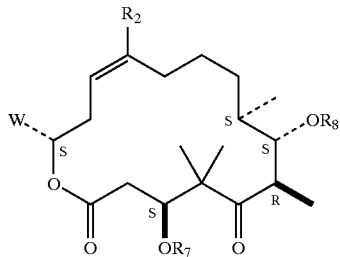

where W is selected from

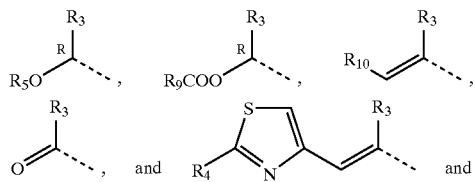

where $R_1$–$R_{12}$ may be defined as described above.

Experimental

All solvents were purchased as reagent grade, and where appropriate were distilled from $CaH_2$ and stored over dry 4 Å sieves for at least one day prior to use. Solvent and reagent transfers were accomplished via dried syringe, and all reactions were routinely conducted under an inert atmosphere unless otherwise indicated. Flash chromatography was accomplished using silica gel (Whatman 60, 230–400 mesh). Preparative thin-layer chromatography utilized 1-,1.5-, or 2-mm-thick Analtech Uniplates with F-256, and 250-μm silica gel thin-layer chromatography plates were also purchased from Analtech. Unless otherwise noted, all NMR analyses were conducted in $CDCl_3$, on Bruker 300, 400, or 500 MHz instruments, and were referenced to chloroform at δ 7.27.

1-Trimethylsilyloxy-4-pentyne 13:

To a solution of 4-pentyn-1-ol (25.0 g, 0.30 mole) in dry $CH_2Cl_2$ (250 ml) at 0° C., was added imidazole (40.46 g, 0.60 mole) and chlorotrimethylsilane (56.6 ml, 0.45 moles) and stirred for 2 h. The reaction mixture was diluted with water and extracted with $CH_2Cl_2$ (3×100 ml). Combined organic extracts were washed with water, brine, dried ($Na_2SO_4$) and the solvent was evaporated. Purification of the crude product by vacuum distillation afforded the pure ether 13 (44.1 g, 95%).

$^1$H NMR (300 MHz $CDCl_3$): δ 3.64 (t, J=5.1 Hz, 2H), 2.24 (t, J=4.6 Hz, 2H), 1.90 (s, 1H), 1.68–1.72 (tt, J=13.2, 6.2 Hz, 2H), 0.09 (s, 9H). $^{13}$C NMR (100 MHz $CDCl_3$): δ 83.9, 68.2, 60.7, 31.2, 14.7, –0.7

Silyloxyepoxide 59:

To a solution of the corresponding epoxy alcohol (10.01 g, 113.6 mmol) in dry $CH_2Cl_2$ (100 ml) at 0° C., was added TBDMSCI (24.8 g, 164.8 mmol) and imidazole (15.46 g, 227.2 mmol) and the mixture was stirred for 4 h. The reaction mixture was diluted with water and extracted with EtOAc (3×80 ml). Combined organic extracts were washed with brine, dried ($Na_2SO_4$) and the solvent was evaporated. Purification on silica gel column chromatography (20% EtOAc in hexanes) furnished epoxide 5a (20.6 g, 90%).

$^1$H NMR (300 MHz $CDCl_3$): δ 3.72–3.68 (m, 1H), 2.82–2.80 (m, 1H), 2.69–2.61 (m, 2H), 1.20 (dd, J=8.2, 1.9 Hz, 3H), 0.85 (s, 9H), 0.03 (s, 3H), 0.02 (s, 3H). $^{13}$C NMR (100 MHz $CDCl_3$): δ 67.5, 55.5, 44.5, 25.6, 20.7, 18.0, –4.9, –5.0

Diol 15a: Opening of the Epoxide and Hydrolysis:

To a stirred solution of pentyne 13 (10.76 g, 69 mmol) in dry toluene (200 ml) at 0° C., n-BuLi (2.5 M solution in hexane, 69 mmol) was added and stirred for 15 min. Subsequently dimethylaluminum chloride solution (1.0 M in hexane, 69 mmol was added and further stirred for 45 min at the same temperature. The oxirane 5a (7.0 g, 34.5 mmol) in toluene (5 ml) was added and the mixture was allowed to warm to room temperature and stirred at RT for 3 hr. The reaction mixture was carefully quenched by addition of saturated $Na_2SO_4$ solution and the slurry obtained was filtered through a pad of celite and washed with EtOAc. The filtrate was dried over $Na_2SO_4$ and the solvent was removed under reduced pressure. The crude residue obtained was dissolved in $H_2O$:acetic acid (1:3) mixture, stirred for 30 min at room temperature, diluted with water and extracted with EtOAc (3×100 ml). The organic phase was washed with water, brine, dried and the solvent was removed. Acetic acid was removed by repeated evaporations with hexane. The residue was purified by flash column chromatography on silica gel to furnish diol 15a (7.9 g, 80%).

$^1$H NMR (400 MHz $CDCl_3$): δ 3.81 (dq, J=11.4, 6.0 Hz, 1H), 3.71 (t, J=6.0 Hz, 2H), 3.55 (dt, J=12.0, 6.3 Hz, 1H), 2.38–2.30 (m, 2H), 2.29–2.21 (m,2H), 1.71 (tt, J=13.0, 6.6 Hz), 1.11 (d, J=6.2 Hz, 3H), 0.88 (s, 9H), 0.06 (s, 6H). $^{13}$C NMR (100 MHz $CDCl_3$); δ 82.1, 77.2, 74.6, 70.7, 61.7, 31.8, 26.1, 23.3, 18.8, 18.3, 15.7, –4.1, –4.5.

Partial Hydrogenation of the Diol 15a:

A mixture of diol 15a (7.5 g, 26 mmol), quinoline (6.2 ml, 52 mmol) and Lindler catalyst (1.125 g) in ethanol (75 ml), were stirred under $H_2$ atmosphere and the reaction was carefully monitored by TLC. Upon completion, the contents were filtered through celite and the filtrate was concentrated. The residue was dissolved in ether (200 ml) and washed with 2% HCl to remove quinoline. The organic phase was further washed with water, 5% $NaHCO_3$ solution, brine, dried ($Na_2SO_4$) and the solvent evaporated. Purification by flash column chromatography over silica gel gave the diol 16a (7.25 g, 96%).

$^1$H NMR (400 MHz $CDCl_3$): δ5.4 1–5.37 (m, 2H), 3.68–3.65 (m, 1H), 3.53–3.51 (m, 1H), 3.46–3.41 (dt, J=8.6, 4.2 Hz, 1H), 2.20–2.07 (m, 2H), 2.05–2.00 (m, 2H), 1.59–1.47 (m, 2H), 1.04 (d, J=6.1 Hz, 3H), 0.81 (s, 9H), –1.2 (s, 3H), –2.9 (s, 3H). $^{13}$C NMR (100 MHz $CDCl_3$): δ 131.9, 126.8, 75.6, 71.5, 61.6, 32.2, 30.6, 26.2, 23.7, 18.3. 17.9, –4.1, –4.5.

Iodide 17a: Monotosylation, Silylation and the Iodination Sequence:

To a solution of the diol 16a (6.21 g, 21.52 mmol) in dry $CH_2Cl_2$ (60 ml) at 0° C., was added tosyl chloride (4.93 g, 25.83 mmol), pyridine (3.5 ml, 43.1 mmol) and catalytic amount of DMAP. The reaction mixture was allowed to warm to room temperature and stirred for overnight. Water was added to the reaction mixture and extracted with EtOAc (3×60 ml). The organic layer was washed with water, brine, dried ($Na_2SO_4$) and the solvent evaporated. Purification by flash column chromatography over silica gel afforded the monotosylate (7.62, 80%).

$^1$H NMR (400 MHz $CDCl_3$): δ 7.78 (d, J=8.2 Hz, 2H), 7.33 (d, J=8.1 Hz, 2H), 5.50–5.35 (m, 2H), 4.03 (t, J=6.4 Hz, 2H), 3.80–3.74 (m, 1H), 3.51–3.50 (m, 1H), 2.44 (s, 3H), 2.14–2.07 (m, 4H), 1.71 (tt, J=14.0, 6.6 Hz, 2H), 1.08 (d,

J=6.3 Hz, 3H), 0.88 (s, 9H), 0.07 (s, 3H), 0.06 (s, 3H). $^{13}$C NMR (100 MHz CDCl$_3$): δ 145.1, 133.6, 130.24, 130.2, 128.2, 127.7, 75.4, 71.3, 70.3, 30.5, 29.1, 26.2, 23.6, 22.0, 18.4, 17.7, −4.0, −4.5.

A mixture of monotosylate (8.34 g, 18.8 mmol), 2,6-lutidine (3.8 ml, 33.0 mmol) and TMSOTf (4.3 ml, 23.6 mmol) in dry CH$_2$Cl$_2$ (50 ml) at 0° C., was stirred while allowing the temperature to rise to room temperature. After stirring at RT for 2 h water was added and extracted into EtOAc (3×60 ml). The organic layer was washed with water, brine, dried (Na$_2$SO$_4$) and the solvent evaporated. Purification by flash column chromatography on silica gel impregnated with triethylamine afforded the pure bis silyl ether (9.36 g, 99%).

$^1$H NMR (400 MHz CDCl$_3$): δ 7.78 (d, J=8.3 Hz, 2H), 7.37 (d, J=8.1 Hz, 2H), 5.47–5.41 (m, 1H), 5.36–5.30 (m, 1H), 4.03 (t, J=6.6 Hz, 2H), 3.66–3.60 (m, 1H), 3.47–3.42 (m, 1H), 2.45 (s, 3H), 2.26–2.2 (m, 1H), 2.11–2.04 (m, 3H), 1.70 (tt, J=14.1, 7.1 Hz, 2H), 1.08 (d, J=6.1 Hz, 3H), 0.88 (s, 9H), 0.08 (s, 9H), 0.05 (s, 3H), 0.04 (s, 3H). $^{13}$C NMR (100 MHz CDCl$_3$): δ 145.0, 133.7, 130.2, 129.4, 128.7, 128.3, 77.8, 72.2, 70.4, 31.8, 29.2, 26.3, 26.2, 23.7, 22.0, 19.8, 18.5, 0.97, −4.0, −4.2.

A mixture of the bis silyl ether obtained above (9.03 g, 18.0 mmol) and NaI (6.74 g, 45.0 mmol) in dry acetone (90 ml), was heated under reflux for 2 h. Removal of the solvent under reduced pressure and purification of the product by flash column chromatography on silica gel to give the pure iodide 17a (7.37 g, 87%).

$^1$H NMR (400 MHz CDCl$_3$): δ 5.5–5.48 (m, 1H), 3.67–3.64 (m, 1H), 3.50–3.46(m, 1H), 3.18 (t, J=7.0 Hz, 2H), 2.32–2.29 (m, 1H), 2.2–2.12 (m, 3H), 1.90 (tt, J=14.2, 7.1 Hz, 2H), 1.12 (d, J=6.2 Hz, 3H), 0.89 (s, 9H), 0.10 (s, 9H), 0.04 (s, 6H). $^{13}$C NMR (100 MHz CDCl$_3$): δ 129.3, 128.8, 100.0, 77.9, 72.2, 33.8, 32.1, 28.6, 26.4, 19.9, 18.6, 6.9, 1.1, −3.9, −4.2.

Bissilyloxyiodide 17b:

Conversion of the diol 16b employing the same reaction sequence described above yielded the iodide 17b.

$^1$H NMR (400 MHz CDCl$_3$): δ 7.75–7.68 (m, 4H), 7.42–7.3 (m, 6H), 5.49–5.33 (m, 2H), 3.76 (dq, J=6.1 Hz, 1H), 3.61 (dt, J=7.9, 4.2 Hz, 1H), 3.16 (t, J=6.9 Hz, 2H), 2.38–2.19 (m, 2H), 2.18–2.05 (m, 2H), 1.4–1.32 (m, 2H), 1.09 (s, 9H), 1.01 (d, J=6.2 Hz, 3H), 0.10 (s, 9H). $^{13}$C NMR (100 MHz CDCl$_3$): δ 136.4, 136.4, 135.2, 134.3, 129.9, 129.8, 129.3, 128.7, 127.9, 127.8, 77.7, 73.3, 33.8, 31.9, 28.6, 27.5, 19.7, 19.5, 6.8, 1.0.

HydroxybisMEMether 22: Bisetherificatlon and Desilylation of 16a:

To a solution of the diol 16a (7.0 g, 24.3 mmol) in dry CH$_2$Cl$_2$ (100 ml) at 0° C., was added DIPEA (21.0 ml, 120 mmol) and MEMCl (13.9 ml, 120 mmol) and stirred for 1 h. The reaction was quenched by the addition of saturated NaHCO$_3$ solution. The organic phase was separated and the aqueous phase was extracted with CH$_2$Cl$_2$ (3×60 ml). The combined organic extracts were washed with water, brine, dried (Na$_2$SO$_4$) and the solvent evaporated. Purification by flash column chromatography using silica gel gave corresponding bis MEM ether (10.4 g, 92%).

$^1$H NMR. (400 MHz CDCl$_3$): δ5.42–5.46 (m, 2H), 4.81 (d, J=7.5 Hz, 1H), 4.75 (d, J=7.5 Hz, 1H), 4.70 (s, 2H), 3.67–3.80 (m, 5H), 3.56–3.51 (m, 6H), 3.39 (s, 3H), 3.38 (s, 3H), 2.26–2.23 (m, 2H), 2.10–2.08 (m, 2H), 1.66–1.62 (m, 3H), 1.12 (d, J=6.2 Hz, 3H), 0.86 (s, 9H), 0.04 (s, 3H), 0.03 (s, 3H). $^{13}$C NMR (100 MHz CDCl$_3$): δ 131.1, 127.0, 95.8, 95.5, 81.7, 72.2, 70.5, 67.6, 67.4, 67.0, 59.3, 29.9, 29.3, 26.2, 24.4, 19.1, 18.4, 14.5, −4.2, −4.4.

To a solution of the bis MEM ether obtained above (9.5 g, 20.4 mmol) in THF (100 ml) at 0° C. was added TBAF (1.0 M solution in THF, 41 mmol) and the mixture was at room temperature for overnight. Diluted with water and extracted with EtOAc (3×100 ml). The combined organic extracts were washed with brine, dried (Na$_2$SO$_4$) and the solvent evaporated. Purification by flash column chromatography on silica gel gave 22 (6.16 g, 86%).

$^1$H NMR (400 MHz CDCl$_3$): δ 5.48–5.41 (m, 2H), 4.80 (d, J=7.2 Hz, 1H), 4.74 (d, J=7.2 Hz, 1H), 4.70 (s, 2H), 3.85–3.80 (m, 2H), 3.79–3.66 (m, 3H), 3.58–3.53 (m, 7H), 3.39 (s, 3H), 3,38 (s, 3H), 2.35–2.28 (m, 2H), 2.22–2.209 (m, 3H), 1.64 (tt, J=13.9, 6.8 Hz, 2H), 1.16 (d, J=6.5 Hz, 3H). $^{13}$C NMR (100 MHz CDCl$_3$): δ 131.1, 126.5, 95.8, 95.5, 83.5, 71.94, 71.9, 68.6, 67.4, 67.3, 66.8, 59.0, 29.7, 28.7, 24.1, 17.7.

Ketobisether 23: Swern Oxidation of the Alcohol 22:

DMSO (9.0 ml, 127.2 mmol) was added to a solution of oxalyl chloride (12.91 g, 101.72 mmol) in CH$_2$Cl$_2$ (60 ml) at −78° C. and stirred for 15 min. The alcohol 22 (5.94 g, 17.0 mmol) in CH$_2$Cl$_2$ was added slowly and stirring was continued for 2 h. Triethylamine was added and the temperature was allowed to rise to RT. Quenched with water, extracted with methylene chloride, washed with water, dried (Na$_2$SO$_4$) and the solvent evaporated. Purification of the crude product by chromatography over silica gel (70% ethylacetate in hexanes) yielded the pure ketone 23 (4.37 g, 74%).

$^1$H NMR (400 MHz CDCl$_3$): δ5.54–5.48 (m, 1H), 5.42–5.36 (m, 1H), 4.8 (d, J=7.0 Hz, 1H), 4.72 (d, J=7.0 Hz, 1H), 4.7 (s, 2H), 4.07 (t, J=6.2 Hz, 1H), 3.74–3.66 (m, 4H), 3.56–3.50 (m, 6H), 3.39 (s, 3H), 3.37 (s, 3H), 2.45 (t, J=6.6 Hz, 2H), 2.17 (s, 3H), 2.11 (q, J=7.4 Hz, 2H), 1.62 (tt, J=14.0, 6.7 Hz, 2H). $^{13}$C NMR (100 MHz CDCl$_3$): δ209.4, 132.5, 124.3, 95.6, 95.3, 82.2, 72.0, 71.9, 67.7, 67.3, 66.9, 59.1, 30.0, 29.6, 26.7, 24.2.

Thiazole 25: Horner-Emmons Reaction of the Ketone 23:

To a solution of the phosphonate 24 (5.6 g, 22.5 mmol) in dry THF (100 ml) at −78° C., was added n-BuLi (2.5 M solution in hexane, 0.95 equiv.) and stirred for 45 min. Subsequently, ketone 23 (3.93 g, 11.25 mmol) in THF (5 ml) was added and stirred for 1h at −78° C. and then slowly allowed to warm to room temperature and left overnight. The reaction was quenched by the addition of saturated NH$_4$Cl solution and extracted with EtOAc (3×60 ml). The organic layer was washed with water, brine, dried (Na$_2$SO$_4$) and the solvent evaporated. Purification by flash column chromatography on silica gel furnished the pure compound 25 (3.85 g, 77%).

$^1$H NMR (400 MHz CDCl$_3$): δ6.84 (s, 1H), 6.38 (s, 1H), 5.35–5.31 (m, 2H), 4.61 (d, J=6.9 Hz, 1H), 4.59 (s, 2H), 4.53 (d, J=6.9 Hz, 1H), 4.0 (t, J=6.8 Hz, 1H), 3.74–3.7 (m, 2H), 3.59–3.56 (m, 2H), 3.52–3.50 (m, 1H), 3.48–3.41 (m, 6H), 3.28 (s, 3H), 3.27 (s, 3H), 2.59 (s, 3H), 2.34–2.30 (m, 1H), 2.28–2.25 (m, 1H), 2.02 (q, J=6.7 Hz, 2H), 1.91 (s, 3H), 1.57–1.50 (tt, J=14.3, 6.7 Hz, 2H). $^{13}$C NMR (100 MHz CDCl$_3$): δ164.8, 153.1, 138.6, 131.3, 126.3, 121.8, 116.3, 95.8, 93.0, 81.9, 72.13, 72.11, 67.6, 67.3, 67.0, 59.3, 32.2, 29.9, 24.4, 19.5, 14.1

Diol 26: Deprotection of the Bisether 25:

A mixture of 25 (3.7 g, 8.34 mmol), THF (30 ml) and 9.0 N HCl were stirred at room temperature for overnight. The reaction mixture was carefully neutralized by addition of 10 % NaHCO$_3$ solution and extracted with EtOAc (3×60 ml). The organic layer was washed with water, brine, dried (Na$_2$SO$_4$) and the solvent evaporated. Purification by flash column chromatography on silica gel (90% EtOAc in hexanes) furnished the diol 26 (1.34 g, 60%).

¹H NMR (400 MHz CDCl₃): δ 6.8 (s, 1H), 6.5 (s, 1H), 5.43–5.32 (m, 2H), 4.11 (t, J=5.1 Hz, 3.54–3.49 (m, 2H), 2.61 (s, 3H), 2.42–2.35 (m, 2H), 2.31–2.26 (m, 2H), 2.19–2.13 (m, 2H), 2.07–2.02 (m, 2H), 1.9 (s, 3H), 1.59–1.49 (m, 2H). ¹³C NMR (100 MHz CDCl₃): δ165.1, 153.0, 142.7, 132.0, 126.5, 118.9, 115.6, 115.56, 77.1, 61.5, 33.7, 32.2, 23.9, 19.3, 14.9.

Silyloxyiodide 27: Monotosylation, Silylation and Iodination Sequence:

To a solution of the diol 26 (2.25 g, 8.4 mmol) in dry CH₂Cl₂ (20 ml) at 0° C., was added tosyl chloride (1.93 g, 10.0 mmol), pyridine (1.36 ml, 16.8 mmol) and catalytic amount of DMAP and the reaction was allowed to warm to room temperature and stirred overnight. The reaction mixture was diluted with water and extracted with EtOAc (3×40 ml). The organic layer was washed with water, brine, dried (Na₂SO₄) and the solvent evaporated. Purification by flash column chromatography over silica gel afforded the corresponding monotosylate (2.83 g, 82%).

¹H NMR (400 MHz CDCl₃): δ 7.74 (d, J=8.3 Hz, 2H), 7.3 (d, J=8.3 Hz, 2H), 6.9 (s, 1H), 6.5 (s, 1H), 5.40–5.36 (m, 2H), 4.12 (t, J=6 Hz, 1H), 3.99 (t, J=6.4 Hz, 2H), 2.66 (s, 3H), 2.40 (s, 3H), 2.30 (t, J=6.3 Hz, 2H), 2.05 (dd, J=14.4, 7.4 Hz, 2H), 1.97 (s, 3H), 1.66 (tt, J=14.2, 7.4 Hz, 2H). ¹³C NMR (100 MHz CDCl₃): δ 165.0, 153.1, 145.1, 142.0, 133.5, 130.6, 130.3, 128.3, 127.3, 119.4, 115.9, 77.9, 70.3, 33.6, 29.1, 23.7, 22.0, 19.5, 14.7.

To a solution of the monotosylate obtained above (2.149, 5.23 mmol) in dry CH₂Cl₂ (30 ml) at 0° C., was added 2,6-lutidine (1.07 ml, 9.14 mmol) and TBSOTf (1.5 ml, 6.53 mmol), the reaction was allowed to warm to room temperature and stirred for 2 h at RT. Diluted with water and extracted with EtOAc (3×60 ml). The organic layer was washed with water, brine, dried (Na₂SO₄) and the solvent evaporated. Purification by flash column chromatography on silica gel afforded the corresponding silylether (2.74 g, 98%)

¹H NMR (400 MHz CDCl₃): δ 7.75 (d, J=6.54 Hz, 2H), 7.30 (d, J=8.3 Hz, 2H), 6.90 (s, 1H), 6.43 (s, 1H), 5.42–5.38 (m, 2H), 5.30–5.25 (m, 1H), 4.09 (t, J=6.3 Hz, 1H), 3.99 (t, J=6.5 Hz, 2H), 2.68 (s, 3H), 2.4 (s, 3H), 2.31–2.17 (m, 2H), 2.08–2.0 (m, 2H), 1.95 (s, 3H), 1.70–1.63 (tt, J=13.9, 6.9 Hz, 2H), 0.84, (s, 9H), 0.03 (s, 3H), –0.01 (s, 3H). ¹³C NMR (100 MHz CDCl₃): δ 164.8, 153.5, 145.1, 142.3, 133.6, 130.2, 129.4, 128.3, 128.0, 119.3, 115.6, 78.8, 70.4, 35.0, 29.2, 26.3, 23.7, 22.0, 19.6, 18.6, 14.3, –4.25, –4.55.

A solution of the silylether obtained above (1.56 g, 2.92 mmol) in dry acetone (25 ml), was added NaI (1.09 g, 7.3 mmol) and the mixture was heated under reflux for 2 h. The solvent was removed under reduced pressure and the crude product obtained was purified by flash column chromatography on silica gel to give the iodide 27 (1.29 g, 90%).

¹H NMR (400 MHz CDCl₃): δ 6.85 (s, 1H), 6.40 (s, 1H), 5.41–5.28 (m, 2H), 4.08 (t, J=6.3 Hz, 1H), 3.11–3.06 (m, 2H), 2.62 (s, 3H), 2.27 (dt, J=12.9, 6.7 Hz, 2H), 2.06 (dt, J=13.8, 6.8, 2H), 1.95 (s, 3H), 1.80 (tt, J=14.0, 6.9 Hz, 2H), 0.83 (s, 9H), 0.0 (s, 3H), –0.05 (s, 3H). ¹³C NMR (100 MHz CDCl₃): δ 164.2, 153.0, 141.9, 141.85, 128.9, 127.6, 118.8, 115.0, 78.4, 34.7, 33.3, 28.1, 25.8, 19.2, 18.1, 13.9, 6.3, –4.7, –5.0.

Alkylation of the Iodide 17b with the Sultam 18:

to a stirred solution of the sultam 18 (4.065 g, 15 mmol) in THF was added n-BuLi (1.056 g, 16.5 mmol) at –78° C. over a period of one hour. The resulting mixture was stirred further at –78° C. for one hour and a mixture of the iodide 17b (9.801 g, 16.5 mmol) and HMPA (5.376 g, 30 mmol) was slowly added. The reaction temperature was allowed to raise to –20° C. and stirring was continued at that temperature for 4 h. Quenched with saturated NH₄Cl solution and extracted with EtOAc. The organic layer was washed with water, brine, dried (Na₂SO₄) and the solvent evaporated. The crude product obtained was purified by chromatography over silica gel (10% ethylacetate in hexanes) to afford the adduct 19b (4.348 g, 59%).

¹H NMR (400 MHz CDCl₃): δ7.72–7.68 (m, 4H), 7.44–7.32 (m, 6H), 5.40–5.28 (m, 2H), 3.89 (t, J=6.2 Hz, 1H), 3.74 (dq, J=6.1, 3.9 Hz, 1H), 3.57 (dt, J=7.9, 4.2 Hz, 1H), 3.46 (q, J=13.7 Hz, 2H), 3.15–3.03 (m, 1H), 2.30–2.20 (m, 1H), 2.19–2.09 (m, 1H), 2.08–2.02 (m, 2H), 2.02–1.92 (m, 2H), 1.93–1.82 (m, 3H), 1.78–1.62 (m, 1H), 1.50–1.25 (m, 4H), 1.16 (s, 3H), 1.15 (d, J=6.6 Hz, 3H), 1.07 (s, 9H), 1.02 (d, J=7.1 Hz, 3H), 0.08 (s, 9H). ¹³C NMR (100 MHz CDCl₃): δ 176.9, 136.4, 136.3, 135.2, 134.3, 131.2, 129.9, 129.8, 127.9, 127.7, 127.2, 77.8, 73.3, 65.6, 53.6, 48.6, 48.1, 45.1, 40.2, 39.0, 35.5, 33.3, 31.9, 27.6, 27.5, 27.3, 26.8, 21.2, 20.3, 19.7, 19.3, 17.0, 1.0.

Alkylation of the Iodide 17a with the Sultam 18:

The alkylation was carried out as outlined above to yield the adduct 19a in 65% yield.

¹H NMR (400 MHz CDCl₃): δ 5.42–5.32 (m, 2H), 3.88 (dd, J=6.9, 5.4 Hz, 1H), 3.68–3.60 (m, 1H), 3.45 (q, J=13.7 Hz, 2H), 3.48–3.42 (m, 1H), 3.10–3.02 (m, 1H), 2.4–2.3 (m, 1H), 2.12–1.96 (m, 5H),1.92–1.82(m, 3H), 1.75–1.65 (m, 1H), 1.50–1.25 (m,5H), 1.15 (s, 3H), 1.14 (d, J=7 Hz, 3H), 1.92 (d, J=6.1 Hz, 3H), 0.96 (s, 3H), 0.87 (s, 9H), 0.08 (s, 9H), 0.04 (s, 6H). ¹³C NMR (100 MHz CDCl₃): δ 176.9, 131.1, 127.2, 77.9, 72.1, 65.6, 53.5, 48.5, 48.0, 45.0, 40.2, 39.0, 35.4, 33.2, 32.0, 27.7, 27.3, 26.8, 26.3, 21.2, 20.3, 19.7, 18.5, 17.0, 1.0, –3.9, –4.2

Alkylation of the Iodide 27 with the Sultam 18:

The alkylation was carried out as outlined above to yield the adduct 28 in 68% yield.

¹H NMR (400 MHz CDCl₃): δ 6.8 (s, 1H), 6.4 (s, 1H), 5.38–5.28 (m, 2H), 4.08 (t, j=6.3 Hz, 1H), 3.85 (t, J=5.8 Hz, 1H), 3.42 (q, J=13.2 Hz, 2H), 3.10–3.02 (m, 1H), 2.6 (s, 3H), 2.32–2.22 (m, 2H), 2.50–1.98 (m, 3H), 1.96 (s, 3H), 1.85–1.80 (m, 2H), 1.72–1.62 (m, 1H), 1.48–1.20 (m, 6H), 1.12 (s, 3H), 1.10 (d, J=6.6 Hz, 3H), 0.92 (s, 3H), 0.86 (s, 9H), 0.02 (s, 3H), –0.01 (s, 3H). ¹³C NMR (100 MHz CDCl₃): δ 176.8, 164.7, 153.4, 142.6, 131.1, 126.6, 119.1, 115.4, 78.9, 65.6, 53.5, 48.5, 48.0, 45.0, 40.1, 39.0, 35.4, 35.0, 33.2, 27.6, 27.3, 26.8, 26.2, 21.2, 20.2,19.5,18.5,16.9, 14.2, –4.2, –4.5.

Aldehyde 20b: Reductive Cleavage of the Adduct 19b:

To a solution of the adduct (3.685 g, 5 mmol) in 1:1 mixture of THF and CH₂Cl₂ (50 ml) at –78° C. was added DIBAH (1.209 g, 8.5 mmol) in CH₂Cl₂. The reaction mixture was warmed to –20° C., stirred at that temperature for 1 hr and quenched with saturated Na₂SO₄ solution. The slurry obtained was filtered through a pad of celite, washed with EtOAc. Evaporation of the filtrate gave the crude product, which was purified by chromatography over silica gel (5% ethylacetate in hexanes) to furnish the pure aldehyde 20b (1.78169, 68%).

¹H NMR (400 MHz CDCl₃): δ 9.62 (d, J=1.9 Hz, 1H), 7.78–7.70 (m, 4H), 7.47–7.35 (m, 6H), 5.48–5.33 (m, 2H), 3.81 (dq, J=6.1, 6.0 Hz, 1H), 3.64 (dt, J=8, 4.3 Hz, 1H), 2.39–2.30 (m, 2H), 2.30–2.20 (m, 1H), 2.10–2.03 (m, 2H), 1.78–1.68 (m, 1H), 1.48–1.32 (m, 3H), 1.15–1.1(m, 12H), 1.04 (d, J=6.2 Hz, 3H), 0.13, (s, 9H). ¹³C NMR (100 MHz CDCl₃): δ 205.3, 136.4, 136.4, 135.2, 134.4, 131.0, 129.9, 129.9, 127.9, 127.8, 127.6, 77.8, 73.3, 46.6, 31.9, 30.5, 27.7, 27.5, 27.3, 27.3, 19.7, 19.4, 13.7,1.05.

Aldehyde 20a: Reductive Cleavage of the Adduct 19a:

The reduction of the adduct 19a was carried out as described above to yield the aldehyde 20a in 71% yield.

¹H NMR (400 MHz CDCl₃): δ9.60 (d, J=1.9 Hz, 1H), 5.45–5.35 (m, 2H), 3.64 (dq, J=5.9, 5.1 Hz, 1H), 3.46 (dt, J=7.8, 4.5 Hz, 1H), 2.38–2.25 (m, 2H), 2.15–2.09 (m, 1H), 2.08–2.02 (m, 2H), 1.75–1.66 (m, 1H), 1.45–1.32 (m, 3H), 1.10 (d, J=6.9 Hz, 3H), 1.09 (d, J=7.1 Hz, 3H), 0.88 (s, 9H), 0.09 (s, 9H), 0.05 (s, 6H). ¹³C NMR (100 MHz CDCl₃): δ 205.2, 130.9, 127.6, 77.9, 77.1, 72.1, 46.5, 32.0, 30.5, 27.7, 27.2, 26.3, 19.8, 18.5, 13.6, 0.99, −3.9, −4.2.

Aldol Reaction of the Sultam 51 with the Aldehyde 9:

To a solution of the acetylsultam 51 (5.02 g, 19.5 mmol) in dry CH₂Cl₂ (35 ml) at 0° C., DIPEA (4.1 ml, 23.4 mmol) and dibutylborontriflate (1.0 M solution in CH₂Cl₂, 21.5 mmol) were added and stirred for 30 min. The reaction mixture was cooled to −78° C. and the keto aldehyde 9 (2.5 g, 19.5 mmol) in CH₂Cl₂ (5 ml) was added and stirring was continued for 1 h The reaction mixture was then allowed to warm to room temperature and quenched by addition of pH 7.0 buffer solution and extracted with EtOAc (3×60 ml). The combined organic layer was washed with water, brine, dried (Na₂SO₄) and the solvent evaporated. The residue was taken in methanol (40 ml), cooled to 0° C. and 30% H₂O₂ (5.0 ml) was added and stirred for 1 h. The reaction mixture was diluted with water and extracted with EtOAc (3×60 ml), washed with brine, dried (Na₂SO₄). Evaporation of the solvent and purification of the crude product using flash chromatography over silica gel (15% EtOAc in hexanes) resulted in the β-hydoxy adduct 52 (3.9 g, 61%).

¹H NMR (300 MHz CDCl₃): δ 4.38–4.32 (m, 1H), 3.92–3.89 (m, 1H), 3.51 (d, J=13.8 Hz, 1H), 3.48 (d, J=13.8 Hz, 1H), 3.28 (d, J=4.3 Hz, 1H), 2.90 (dd, J=15.6, 2.2 Hz, 1H), 2.80–2.72 (m, 1H), 2.62–2.58 (m, 2H), 2.22–2.12 (m, 1H), 2.10–2.05 (m, 1H), 1.92–1.85 (m, 3H), 1.45–1.31 (m, 2H), 1.20 (s, 3H), 1.18 (s, 3H), 1.15 (s, 3H), 1.03 (t, J=7.2 Hz, 3H), 0.99 (s, 3H). ¹³C NMR (100 MHz CDCl₃): δ 216.1, 171.6, 73.1, 63.5, 53.3, 51.5, 48.9, 48.1, 45.1, 39.1, 38.8, 33.2, 31.5, 26.8, 23.3, 21.9, 20.2, 19.6, 8.3.

Keto Acid 10: Silylation and Hydrolysis of the Adduct 52:

To a mixture of the adduct 52 (2.18 g, 5.7 mmol) in dry CH₂Cl₂ (40 ml) at 0° C., was added 2,6-lutidine (1.3 ml, 11 mmol) and TBDMSOTf (1.95 ml, 8.5 mmol). The reaction mixture was allowed to warm to room temperature and stirred for a period of 3 h. Water was added to the reaction mixture and extracted with EtOAc (3×30 ml). Combined organic extracts were washed with water, brine, dried (Na₂SO₄) and the solvent was evaporated. Purification by flash chromatography over silica gel (5% EtOAc in hexanes) gave the corresponding silylated adduct (2.54 g, 90%).

To a solution of silylated adduct obtained above (1.95 g, 3.9 mmol) in H₂O:THF (1:3), was added 30% H₂O₂ (3.0 ml, 7.0 equiv.) and LiOH.H₂O (0.327 g, 7.8 mmol) and stirred at ambient temperature for 6 h. Water was added to the reaction mixture and extracted with EtOAc. The aqueous phase was acidified with 2.0 N HCl, and extracted into EtOAc (3×50 ml). Combined organic extracts were washed with water, brine, dried (Na₂SO₄) and the solvent was evaporated. Purification by flash column chromatography over silica gel (20% ether in hexanes) furnished the acid 10 (0.74 g, 63%).

¹H NMR (400 MHz CDCl₃): δ4.46 (dd, J=6.8, 3.7 Hz, 1H), 2.60–2.46 (m, 3H), 2.32 (q, J=6.9 Hz, 2H), 1.14 (s, 3H), 1.09 (s, 3H), 1.01 (t, J=7.1 Hz, 3H), 0.85 (s, 9H), 0.06 (s, 3H), 0.04 (s, 3H). ¹³C NMR (100 MHz CDCl₃): δ 215.5, 73.9, 53.0, 39.6, 32.2, 26.3, 21.5, 20.9, 18.5, 8.1, −4.0, −4.5.

Aldol Condensation of the Acid 34 with Aldehyde 20a:

To a solution of LDA in THF (5 ml) at −78° C. [generated from n-BuLi (155 mg, 2.42 mmol) and DIPA (2.67 mg, 2.64 mmol)] was added the acid 34 (0.332 g, 1.1 mmol) in THF. Temperature was allowed to raise to −30° C. and stirred at that temperature for 45 min. Aldehyde 20a (0.400 g, 1 mmol) in THF was added and the reaction mixture was stirred at −78° C. for 1 hr. Quenched with saturated ammonium chloride solution and extracted with ethylacetate. The organic layer was washed with water, brine, dried (Na₂SO₄) and solvent evaporated to give a crude product which was used for the next step without further purification.

To a solution of crude product obtained from the previous reaction in CH₂Cl₂ (5 ml) at 0° C. was added 2,6-lutidine (642.9 mg, 6 mmol) and tert.butyidimethylsilyltrifluromethane sulfonate (1.0573 g, 4 mmol) and the reaction mixture was stirred for 2 hr. Water was added and extracted with ethylacetate. The organic layer was washed with water, brine, dried (Na₂SO₄) and solvent evaporated. The crude product obtained was dissolved in THF (20 ml), water (2 ml) and acetic acid (7 ml) were added and the mixture was stirred overnight at room temperature. Added water and extracted with ethylacetate. The organic layer was washed with water, brine, dried (Na₂SO₄) and solvent evaporated. Purification of the crude product by column chromatography over silica gel afforded the acids 36–39 as a mixture of diastereomers (590 mg, 78%).

Macrolactonization of the Acids 36–39:

To a solution of the mixture of the acids 36–39 (590 mg, 0.78 mmol) in THF (7 ml) at 0° C. was added triethylamine (552 mg, 5.46 mmol) and 2,4,6-trichlorobenzoyl chloride (951 mg, 3,9 mmol). The mixture was stirred for 30 min and transferred via a cannula to a solution of DMAP (1.05 g, 8.58 mmol) in toluene (433 ml). The turbid solution obtained was stirred overnight and toluene was removed under reduced pressure. The residue obtained was purified by column chromatography over silica gel (5% ethylacetate in hexanes) to give the lactones 40–43.

Lactone 40 (156 mg, 27%):

¹H NMR (400 MHz CDCl₃): δ 5.41 (dt, J=9.2, 4.1 Hz, 1H), 5.35–5.25 (m, 1H), 5.13 (dt, J=8.7, 2.5 Hz, 1H), 4.38 (dd, J=7.0 Hz, 1H), 4.0 (dd, J=5.0, 2.5 Hz, 1H), 2.97 (dq, J=7.0 Hz, 1H), 2.52–2.32 (m, 3H), 2.26 (dd, J=17.1, 2.4 Hz, 1H), 2.16 (s, 3H), 2.12–2.02 (m, 1H), 2.0–1.88 (m, 1H), 1.62–1.48 (m, 2H), 1.27 (s, 3H), 1.2–1.1 (m, 2H), 1.13 (s, 3H), 1.11 (d, J=7.1 Hz, 3H), 0.9–0.85 (m, 12H), 0.84 ((s, 9H), 0.09 (s, 3H), 0.06 (s, 6H), 0.00 (s, 3H). ¹³C NMR (100 MHz CDCl₃): δ 219.2, 205.5, 170.9, 135.5, 123.5, 78.44, 74.7, 72.7, 53.9, 44.5, 40.8, 35.2, 32.9, 29.2, 28.5, 27.4, 26.8, 26.5, 26.3, 18.7, 18.6, 17.6, 16.9, 15.2, −3.6, −3.8, −4.0, −4.3.

Lactone 41 (98 mg, 17%):

¹H NMR (400 MHz CDCl₃): δ 5.6–5.5 (m, 1H), 5.25–5.15 (m, 1H), 5.07 (t, J=4.36, 1H), 4.28 (dd, J=7.6, 2.0 Hz, 1H), 3.81 (d, J=7.2 Hz, 1H), 3.07 (dq, J=7.0 Hz, 1H), 2.77 (ddd, J=14.7, 9.6, 5.4 Hz, 1H), 2.62 (dd, J=17.6, 1.9 Hz, 1H), 2.53 (dt, J=14.9, 5.1 Hz, 1H), 2.45 (dd, J=17.6, 7.9 Hz, 1H), 2.19 (s, 3H), 1.95–1.75 (m, 2H), 1.9–1.8 (m, 2H), 1.27 (s, 3H), 1.19–1.1 (m, 2H), 1.09 (d, J=6.8 Hz, 3H), 1.05 (s, 3H), 0.89 (s, 9H), 0.88–0.80 (m, 12H), 0.13 (s, 3H), 0.07 (s, 3H), 0.05 (s, 3H), 0.02 (s, 3H). ¹³C NMR (100 MHz CDCl₃): δ 218.8, 206.2, 171.6, 134.7, 123.0, 79.1, 76.3, 72.0, 54.2, 47.4, 40.1, 38.6, 34.5, 28.6, 27.6, 27.2, 26.9, 26.6, 26.5, 24.1, 19.1, 19.0, 18.0, 17.3, 13.8.

Lactone 42 (57 mg, 10%):

¹H NMR (400 MHz CDCl₃): δ 5.54–5.45 (m, 1H), 5.28–5.2 (m, 1H), 5.07 (dd, J=7.3, 3.4 Hz, 1H), 4.34 (dd, J=7.6, 2.6, 1H), 3.87 (dd, J=5.4, 2.5 Hz, 1H), 2.98 (dq, J=6.1 Hz, 1H), 2.72–2.65 (m, 1H), 2.58–2.44 (m, 3H), 2.19 (s, 3H), 2.1–1.95 (m, 1H), 1.60–1.48 (m, 1H), 1.48–1.38 (m, 2H), 1.3–1.2 (m, 1H), 1.22 (s, 3H), 1.12 (d, J=6.9 Hz, 3H), 1.05 (s, 3H), 0.94 (d, J=6.9 Hz, 3H), 0.90 (s, 9H), 0.87 (s, 9H), 0.11 (s, 3H), 0.08 (s, 3H), 0.06 (s, 3H), 0.00 (s, 3H).

Lactone 43 (81 mg, 14%):

$^1$H NMR (400 MHz CDCl$_3$): δ 5.61–5.51 (m, 1H), 5.36–5.25 (m, 2H), 4.51 (dd, J=4.4, 3.0 Hz, 1H), 3.83 (d, J=9.2 Hz, 1H), 3.11 (dq, J=9.0, 6.6 Hz, 1H), 2.55–2.45 (m, 2H), 2.40–2.30 (m, 2H), 2.15 (s, 3H), 2.02–1.90 (m, 1H), 1.9–1.78 (m, 1H), 1.44–1.20 (m, 4H), 1.19 (s, 3H), 1.16 (s, 3H), 1.11 (d, J=6.8 Hz, 3H), 0.89 (s, 9H), 0.88–0.80 (m, 12H), 0.01 (s, 3H), 0.05 (s, 3H), 0.05 (s, 3H), 0.03 (s, 3H). $^{13}$C NMR (100 MHz CDCl$_3$): δ 220.5, 206.0, 171.5, 134.9, 123.4, 78.0, 76.9, 71.6, 55.0, 46.6, 42.2, 37.8, 34.7, 29.4, 27.3, 27.1, 26.6; 26.4, 26.2, 26.0, 18.9, 18.7, 18.5, 16.7, 13.9, −2.9, −3.1, −3.8, −4.7

Conversion of the Trisilylether 40 into Lactone 45: Selective Deprotection, Swern Oxidation and the Wittig Reaction Sequence:

Selective Deprotection:

A solution of the lactone 40 (73.8 mg, 0.1 mmol) in tert.BuOH (1 ml) and CH$_2$Cl$_2$ (0.25 ml) was added acetonitrile (3 ml) and hydrosilicic acid (14.4 mg, 0.1 ml) and the mixture was stirred at room temperature for 36 h. Water was added and extracted with ethylacetate. The organic layer was washed with water, brine, dried (Na$_2$SO$_4$) and solvent evaporated. Purification of the crude product by silica gel chromatography (hexane: ethylacetate) yielded the corresponding pure alcohol (43 mg, 69%).

$^1$H NMR (400 MHz CDCl$_3$): δ 5.4–5.3 (m, 2H), 4.83 (dt, J=7.9, 2.0 Hz, 1H), 4.41 (d, J=7.8 Hz, 1H), 4.12–4.06 (m, 1H), 3.88 (dq, J=6.5 Hz, 1H), 2.48–2.39 (M, 1H), 2.36 (dd, J=17.4, 8.5 Hz, 1H), 2.15–2.0 (m, 3H), 2.0–1.87 (m, 1H), 1.6–1.5 (m, 3H), 1.27 (s, 3H), 1.18 (d, J=6.3 Hz, 3H), 1.15 (s, 3H), 1.11 (d, J=7.1 Hz, 3H), 0.89–0.86 (m, 12H), 0.85 (s, 9H), 0.11 (s, 3H), 0.07 (s, 6H), 0.01 (s, 3H).

Swern Oxidation:

DMSO (35.16 mg, 0.45 mmol) was added to a solution of oxalyl chloride (28.6 mg, 0.225 mmol) in CH$_2$Cl$_2$ (2 ml) at −78° C. and stirred for 15 min. The alcohol obtained from the previous reaction (47 mg, 0.075 mmol) in CH$_2$Cl$_2$ was added slowly and stirring was continued for 2 h. Quenched with water, extracted with methylene chloride, washed with water, dried (Na$_2$SO$_4$) and solvent evaporated. Purification of the crude product on chromatography over silica gel (10% ethylacetate in hexanes) yielded the pure ketone 44 (42 mg, 90%).

$^1$H NMR (400 MHz CDCl$_3$): δ 5.41 (dt, J=9.2, 4.1 Hz, 1H), 5.35–5.25 (m, 1H), 5.13 (dt, J=8.7, 2.5 Hz, 1H), 4.38 (dd, J=7.0 Hz, 1H), 4.0 (dd, J=5.0, 2.5 Hz, 1H), 2.97 (dq, J=7.0 Hz, 1H), 2.52–2.32 (m, 3H), 2.26 (dd, J=17.1, 2.4 Hz, 1H), 2.16 (s, 3H), 2.12–2.02 (m, 1H), 2.0–1.88 (m, 1H), 1.62–1.48 (m, 2H), 1.27 (s, 3H), 1.2–1.1 (m, 2H), 1.13 (s, 3H), 1.11 (d, J=7.1 Hz, 3H), 0.9–0.85 (m, 12H), 0.84 ((s, 9H), 0.09 (s, 3H), 0.06 (s, 6H), 0.00 (s, 3H). $^{13}$C NMR (100 MHz CDCl$_3$): δ 219.2, 205.5, 170.9, 135.5, 123.5, 78.44, 74.7, 72.7, 53.9, 44.5, 40.8, 35.2, 32.9, 29.2, 28.5, 27.4, 26.8, 26.5, 26.3, 18.7, 18.6, 17.6, 16.9, 15.2, −3.6, −3.8, −4.0, −4.3.

Horner-Emmons Reaction:

n-Butyllithium (5.12 mg, 0.08 mmol) was added to a solution of the phosphonate 24 (20 mg, 0.08 mmol) in THF (1 ml) at −78° C. and the mixture was stirred for 45 min at that temperature. The ketone 44 (25 mg, 0.04 mmol) in THF was added and the temperature was allowed to raise to room temperature. Stirred at room temperature overnight, water was added and extracted with ethylacetate. The organic layer was washed with water, brine, dried (Na$_2$SO$_4$) and solvent evaporated to give the crude product. Purification by preparative TLC (5% EtOAc in hexanes) gave the starting ketone 44 (10 mg) and the product 45 (8.5 mg, 50%).

$^1$H NMR (400 MHz CDCl$_3$): δ 6.9 (s, 1H), 6.5 (s, 1H), 5.9–5.78 (m, 3H), 4.36 (dd, J=8.2, 1.4 Hz, 1H), 4.08 (t, J=3.3 Hz, 1H), 2.98 (dq, J=7.0 Hz, 1H), 2.70 (s, 3H), 2.62–2.52 (m, 1H), 2.38 (dd, J=17.2, 8.3 Hz, 1H), 1.68–1.5 (m, 3H), 1.31 (s, 3H), 1.19–1.09 (m, 2H), 1.14 (s, 3H), 1.11 (d, J=7.1 Hz, 3H), 0.92–0.85 (m, 12 H), 0.78 (s, 9H), 0.1–0.04 (m, 9H), −0.07 (s, 3H). $^{13}$C NMR (100 MHz CDCl$_3$): δ 219.2, 170.5, 164.9, 152.9, 138.4, 134.3, 125.2, 120.0, 116.3, 78.2, 73.8, 73.1, 53,6, 44.3, 41.4, 40.7, 33.3, 32.6, 28.8, 27.5, 26.7, 26.5, 23.3, 19.6, 18.7, 18.6, 17.5, 16.4, 15.6, 14.7, −3.8, −3.9, −4.1, −4.3.

Conversion of the Compound 41 in to the Lactone 47:

Selective deprotection of the silyl ether was carried out as described for 40 to give the corresponding alcohol in 75% yield.

$^1$H NMR (400 MHz CDCl$_3$): δ 5.53 (dt, J=9.0, 8.7 Hz, 1H), 5.42 (dt, J=9.0, 8.8 Hz, 1H), 4.6 (dt, J=7.0, 5.4 Hz, 1H), 4.30 (d, J=7.0 Hz, 1H), 3.90 (dq, J=6.1 Hz, 2H), 3.81 (d, J=7.6 Hz, 1H), 3.08 (dq, J 6.7 Hz, 1H), 2.64 (ddd, J=14.7, 8.6, 5.2 Hz, 1H), 2.46 (d, J=18.0 Hz, 1H), 2.3 (dd, J=17.8, 7.3 Hz, 2H), 1.95–1.7 (m, 3H), 1.37–1.25 (m, 1H), 1.29 (s, 3H), 1.20 (d, J=6.2 Hz, 3H), 1.23–1.13 (m, 2H), 1.09 (d, J=6.8 Hz, 3H), 1.10 (s, 3H), 0.89 (s, 9H), 0.87–0.82 (m, 21H), 0.14 (s, 3H), 0.06 (s, 3H), 0.05 (s, 3H), 0.02 (s, 3H). $^{13}$C NMR (100 MHz CDCl$_3$): δ 171.9, 133.6, 124.5, 78.7, 76.5, 71.3, 68.3, 54.3, 47.4, 39.9, 38.0, 34.4, 27.2, 26.9, 26.7, 26.7, 26.5, 24.3, 19.9, 19.0, 18.8, 18.5, 17.7, 13.4, −2.9, −3.4, −3.7, −4.3.

Swern oxidation of the alcohol obtained from the above reaction following the procedure described earlier resulted in the corresponding ketone in 92% yield.

$^1$H NMR (400 MHz CDCl$_3$): δ 5.6–5.5 (m, 1H), 5.25–5.15 (m, 1H), 5.07 (t, J=4.36, 1H), 4.28 (dd, J=7.6, 2.0 Hz, 1H), 3.81 (d, J=7.2 Hz, 1H), 3.07 (dq, J=7.0 Hz, 1H), 2.77 (ddd, J=14.7, 9.6, 5.4 Hz, 1H), 2.62 (dd, J=17.6, 1.9 Hz, 1H), 2.53 (dt, J=14.9, 5.1 Hz, 1H), 2.45 (dd, J=17.6, 7.9 Hz, 1H), 2.19 (s, 3H), 1.95–1.75 (m, 2H), 1.9–1.8 (m, 2H), 1.27 (s, 3H), 1.19–1.1 (m, 2H), 1.09 (d, J=6.8 Hz, 3H), 1.05 (s, 3H), 0.89 (s, 9H), 0.88–0.80 (m, 12H), 0.13 (s, 3H), 0.07 (s, 3H), 0.05 (s, 3H), 0.02 (s, 3H). $^{13}$C NMR (100 MHz CDCl$_3$): δ 218.8, 206.2, 171.6, 134.7, 123.0, 79.1, 76.3, 72.0, 54.2, 47.4, 40.1, 38.6, 34.5, 28.6, 27.6, 27.2, 26.9, 26.6, 26.5, 24.1, 19.1, 19.0, 18.0, 17.3, 13.8.

Horner-Emmons reaction of the ketone obtained above following the procedure described for 44 yielded the lactone 47 in 52% yield.

$^1$H NMR (400 MHz CDCl$_3$): δ 6.96 (s, 1H), 6.55 (s, 1H), 5.58–5.48 (m, 1H), 5.38–5.29 (m, 1H), 5.29–5.22 (t, J=4.4 Hz, 1H), 4.31 (dd, J=7.0, 2.9 Hz, 1H), 3.83 (d, J=7.0 Hz, 1H), 3.08 (dq, J=7.0 Hz, 1H), 2.81–2.70 (m, 1H), 2.71 (s, 3H), 2.57 (dd, J=17.8, 3.3 Hz, 1H), 2.41 (dd, J=17.8, 7.0 Hz, 2H), 2.08 (s, 3H), 2.09–1.95 (m, 1H), 1.93–1.8 (m, 1H), 1.42–1.30 (m, 2H), 1.29 (s, 3H), 1.20–1.10 (m, 2H), 1.10 (d, J=6.9 Hz, 3H), 1.06 (s, 3H), 0.92–0.8 (m, 21H), 0.14 (s, 3H), 0.08 (s, 3H), 0.06 (s, 3H),. 0.02 (s, 3H). $^{13}$C NMR (100 MHz CDCl$_3$): δ 219.0, 171.6, 153.0, 151.0, 136.9, 133.7, 124.0, 119.8, 116.4, 78.3, 76.2, 71.8, 54.1, 47.4, 40.1, 38.2, 34.3, 30.43, 27.1, 26.9, 26.7, 26.5, 24.2, 19.6, 19.2, 19.0, 18.8, 17.4, 16.2, 13.8, −2.9, −3.4, −3.6, −4.4.

Conversion of the Compound 42 in to the Lactone 48:

Selective deprotection of the silyl ether was carried out as described for 40 to give the corresponding alcohol in 71% yield.

$^1$H NMR (400 MHz CDCl$_3$): δ 5.5–5.35 (m, 2H), 4.77 (dt, J=5.9, 4.8 Hz, 1H), 4.41 (dd, J=8, 1.7 Hz, 1H), 4.97–3.88 (m,

2H), 2.88 (dq, J=6.9 Hz, 1H), 2.5–2.43 (m, 2H), 2.36 (d, J=8 Hz, 1H), 2.30 (dd, 16.9, 1.9 Hz, 1H), 2.14–2.04 (m, 1H), 2.0–1.9 (m, 1H), 1.8–1.74 (m, 1H), 1.58–1.45 (m, 1H), 1.30–1.124 (m, 2H), 1.21 (d, J=6.4 Hz, 3H), 1.19 (s, 3H), 1.3 (d, J=7.0 Hz, 3H), 1.05 (s, 3H), 0.93 (d, J=6.8 Hz, 3H), 0.89 (s, 9H), 0.86 (s, 9H), 0.12 (s, 3H), 0.07 (s, 3H), 0.06 (s, 3H), 0.02 (s, 3H). $^{13}$C NMR (100 MHz CDCl$_3$): δ 217.6, 171.8, 133.2, 125.5, 78.3, 76.4, 73.1, 69.2, 53.9, 41.0, 40.3, 31.9, 28.4, 27.4, 27.1, 26.5, 26.3, 23.0, 20.3, 19.5, 18.8; 18.7, 16.9, 14.4, −3.4, −3.6, −3.6, −4.1.

Swern oxidation of the alcohol obtained from the above reaction following the procedure described earlier, resulted in the corresponding ketone in 85% yield.

$^1$H NMR (400 MHz CDCl$_3$): δ 5.54–5.45 (m, 1H), 5.28–5.2 (m, 1H), 5.07 (dd, J=7.3, 3.4 Hz, 1H), 4.34 (dd, J=7.6, 2.6, 1H), 3.87 (dd, J=5.4, 2.5 Hz, 1H), 2.98 (dq, J=6.1 Hz, 1H), 2.72–2.65 (m, 1H), 2.58–2.44 (m, 3H), 2.19 (s, 3H), 2.1–1.95 (m, 3H), 1.60–1.48 (m, 1H), 1.48–1.38 (m, 2H), 1.3–1.2 (m, 1H), 1.22 (s, 3H), 1.12 (d, J=6.9 Hz, 3H), 1.05 (s, 3H), 0.94 (d, J=6.9 Hz, 3H), 0.90 (s, 9H), 0.87 (s, 9H), 0.11 (s, 3H), 0.08 (s, 3H), 0.06 (s, 3H), 0.00 (s, 3H).

Horner-Emmons reaction of the ketone obtained above following the procedure described for 44 yielded the lactone 48 in 48 % yield.

Conversion of the Compound 43 in to the Lactone 49:

Selective deprotection of the silyl ether was carried out as described for 40 to give the corresponding alcohol in 63% yield.

$^1$H NMR (400 MHz CDCl$_3$): δ 5.60–5.46 (m, 1H), 5.50–5.36 (m, 1H), 4.90–4.82 (m, 1H), 4.57 (dd, J=5.8, 2.0 Hz, 1H), 3.90–3.80 (m, 2H), 3.09 (dq, J=7.0 Hz, 1H), 2.48–2.35 (m, 1H), 2.28 (dd, J=17.7, 6.2 Hz, 1H), 2.22–2.10 (m, 2H), 2.0–1.75 (m, 3H), 1.48–1.28 (m, 2H), 1.18 (s, 3H), 1.18 (d, J=6.0 Hz, 3H), 1.14 (s, 3H), 1.10 (d, J=6.8 Hz, 3H), 0.89 (s, 9H), 0.85–0.78 (m, 12H), 0.09 (s, 3H), 0.05 (s, 3H), 0.04 (s, 3H), 0.00 (s, 3H). $^{13}$C NMR (100 MHz CDCl$_3$) δ 219.7, 170.7, 132,9, 124.3, 76.7, 75.6, 70.7, 68.5, 53.8, 46.0, 41.1, 36.7, 33.2, 27.5, 25.9, 25.8, 25.7, 24.9, 18.5, 18.2, 17.8, 17.8, 15.9, 12.8, −3.8, −3.9, −4.5, −5.4.

Swern oxidation of the alcohol obtained from the above reaction following the procedure described earlier resulted in the corresponding ketone in 88% yield.

$^1$H NMR (400 MHz CDCl$_3$): δ 5.61–5.51 (m, 1H), 5.36–5.25 (m, 2H), 4.51 (dd, J=4.4, 3.0 Hz, 1H), 3.83 (d, J=9.2 Hz, 1H), 3.11 (dq, J=9.0, 6.6 Hz, 1H), 2.55–2.45 (m, 2H), 2.40–2.30 (m, 2H), 2.15 (s, 3H), 2.02–1.90 (m, 1H), 1.9–1.78 (m, 1H), 1.44–1.20 (m, 4H), 1.19 (s, 3H), 1.16 (s, 3H), 1.11 (d, J=6.8 Hz, 3H), 0.89 (s, 9H), 0.88–0.80 (m, 12H), 0.01 (s, 3H), 0.05 (s, 3H), 0.05 (s, 3H), 0.03 (s, 3H). $^3$C NMR (100 MHz CDCl$_3$): δ 220.5, 206.0, 171.5, 134.9, 123.4, 78.0, 76.9, 71.6, 55.0, 46.6, 42.2, 37.8, 34.7, 29.4, 27.3, 27.1, 26.6, 26.4, 26.2, 26.0, 18.9, 18.7, 18.5, 16.7, 13.9, −2.9, −3.1, −3.8, −4.7

Horner-Emmons reaction of the ketone obtained above following the procedure described for 44 yielded the lactone 49 in 45 % yield.

$^1$H NMR (400 MHz CDCl$_3$): δ 6.9 (s, 1H), 6.4 (s, 1H), 5.58–5.48 (m, 1H), 5.46–5.42 (m, 1H), 5.42–5.33 (m, 1H), 4.55 (dd, J=6.0, 2.5 Hz, 1H), 3.87 (d, J=9.0 Hz, 1H), 3.13 (dq, J=8.9, 6.8 Hz, 1H0, 2.70 (s, 3H), 2.51 (dt, J=14.2, 8.1 Hz, 1H), 2.38–2.32 (m, 1H), 2.30 (d, J=6.0 Hz,1H), 2.23 (dd, J=17.6, 2.5 Hz,1H), 2.07 (s, 3H), 2.07–1.95 (m, 1 H), 1.46–1.3 (m, 3H), 1.2 (s, 3H), 1.16 (s, 3H), 1.11 (d, J=6.9 Hz, 3H), 0.90 (s, 9H), 0.87 (d, J=6.7 Hz, 3H), 0.83 (s, 9H), 0.09 (s, 3H), 0.06 (s, 3H), 0.06 (s, 3H), 0.03 (s, 3H). $^{13}$C NMR (100 MHz CDCl$_3$): δ 220.4, 171.1, 164.9, 153.7, 138.0, 133.6, 125.0, 119.3, 116.1, 77.29, 76.6, 71.6, 54.7, 46.8, 42.0, 37.8, 34.2, 32.0, 27.1, 26.6, 26.4, 26.4, 25.9, 19.6, 18.9, 18.6, 18.5, 16.8, 16.1, 13.7.

Preparation of 81:

To a flame dried Mg in THF (5 ml) under argon a crystal of I$_2$ and TIPSBr, 80 (2.95 g, 10.0 mmol) in THF (5 ml) was added slowly. After the completion of the addition it was refluxed for 30 min. Grignard reagent was then added to CuBr.DMS complex (2.055 g, 10.0 mmol) in ether (15 ml) and DMS (10 ml) at −45° C. It was allowed to stir at −45° C. for 2.5 h. To this propyne (400 mg, 10 mmol) was added by condensing at −50° C. with the help of cold finger. Then the reaction mixture was brought to −23° C. and stirred at this temperature for 3 h. Then the reaction mixture was cooled to −50° C. and I$_2$ was added and slowly allowed the reaction mixture to bring to −15° C. and stirred for 30 min and then quenched with NH$_4$Cl saturated solution. Extracted with ether (3×50 ml) and combined organic exacts were washed with water, brine dried over Na$_2$SO$_4$. Evaporation of the solvent and purification by column chromatography over silica gel afforded the product 81 (0.582 g, 30%).

$^1$H NMR (400 MHz in CDCl$_3$) δ 6.00 (s, 1H), 3.84 (t, J=12 Hz, 2H), 2.38 (t, J=8.1 Hz, 2H), 2.01 (s, 3H), 1.7 (m, 2H), 1.37 (m, 3H), 1.19 (d, J=4.8 Hz, 18 H). $^{13}$C NMR (100 MHz in CDCl$_3$) δ145.1, 138.7, 112.8, 75.8, 71.3, 20.6, 17.7, −0.07.

Preparation of 82:

A solution of iodo compound 81 (1.905 g, 5.0 mmol) in toluene (10 ml) at 0° C. was treated with n-BuLi (320 mg, 2.0 ml of 2.5 M solution in hexane) and stirred for 15 min. followed by addition of dimethylaluminium chloride (462.5 mg, 4.9 ml of 1.0 M solution in hexane). The reaction mixture was stirred at 0° C. for 45 min and epoxide (1.623 g, 5.0 mmol) in toluene (5.0 ml) was added. The contents were stirred at room temperature for 5 h. Quenched the reaction by addition of saturated Na$_2$SO$_4$ solution and extracted with ethylacetate. Organic layer was washed with brine and dried over Na$_2$SO$_4$. Evaporation of the solvent and purification by column chromatography over silica gel afforded the product 82 (2.46 g, 85%).

$^1$H NMR (400 MHz in CDCl$_3$) δ 7.6 (m, 4H), 7.24 (m, 6H), 4.98 (t, J=8.0 Hz, 1H), 3.7 (m, 1H), 3.57 (m, 3H), 1.9 (m, 2H), 1.59 (s, 3H), 1.49 (m, 2H), 1.2 (m, 3H), 1.01 (d, J=8.0 Hz, 18H), 0.9 (s, 9H).

Preparation of 83:

A mixture of 82 (2.469, 4.23 mmol) and 0.01 N HCl (4.0 ml) in ethanol was stirred under reflux for 3 h. The solvent was removed under reduced pressure and the residue was extracted into diethyl ether (2×25 ml) and washed successively with saturated solution of NaHCO$_3$, brine. Combined organic extracts were dried (Na$_2$SO$_4$). Evaporation furnished a colorless oil which was purified by flash column chromatography over silica gel to afford product 83 (1.71 g, 95%).

$^1$H NMR (400 MHz in CDCl$_3$) δ 7.6 (d, J=8.0 Hz, 4H), 7.33 (m, 6H), 5.02 (t, J=8.6 Hz, 1H), 3.7 (m, 1H), 3.5 (m, 3H), 2.1 (m, 4H), 1.59 (s, 3H), 0.99 (brs, 12H).

Preparation of 84:

p-Toluene sulfonyl chloride (0.835 g, 4.39 mmol) was added in portionwise to a solution of 83 (1.71 g, 3.99 mmol) in dichloromethane (10 ml), pyridine (0.5 ml) and DMAP (catalytic). Reaction mixture was stirred for 6 h at room temperature and saturated NaHCO$_3$ was added. Extracted with EtOAc (2×20 ml) and combined organic layer was washed with 10% HCl, saturated NaHCO$_3$ and brine. Organic layer was dried over (Na$_2$SO$_4$). Evaporation of the organic solvent and purification of the crude product afforded 84 (2.12 g, 92%).

¹H NMR (400 MHz in CDCl₃) δ 7.76 (d, J=12 Hz, 2H), 7.58 (m, 4H), 7.3 (m, 6H), 7.24 (d, J=10 Hz, 2H), 4.8 (t, J=8.0 Hz, 1H), 3.89 (t, J=14.0 Hz, 2H), 3.72 (m, 1H), 3.48 (m, 1H), 2.35 (s, 3H), 1.97 (m, 4H), 1.58 (m, 2H), 1.51 (s, 3H), 0.98 (s, 9H), 0.93 (d, J=8;0 Hz, 3H).

Preparation of 85:

To a solution of 84 (2.12 g, 3.66 mmol) in dichloromethane (20 ml) at 0° C., 2,6-lutidine (0.54 ml, 4.39 mmol) and tert. butyldimethyl trifluoromethane sulfonate (0.846 ml, 4.39 mmol) and stirred the contents for 2 h. Diluted with CH₂Cl₂ (20 ml) and was washed with 10% aqueous HCl (2×10 ml), followed by water, brine. Organic layer was dried over (Na₂SO₄), evaporation of the organic solvent and purification by flash column chromatography over silica gel yielded 85 (2.41 g, 96%).

¹H NMR (400 MHz in CDCl₃) δ 7.75 (d, J=12.0 Hz, 2H), 7.72 (m, 4H), 7.33 (m, 10H), 4.97 (t, J=8.0 Hz, 1H), 3.9 (t, J=8.2 Hz, 2H), 3.66 (m, 1H), 3.56 (m, 1H), 2.39 (s, 3H), 2.0–1.9 (m, 4H), 1.53 (s, 3H), 1.22 (m, 2H), 1.0 (s, 9H), 0.82 (brs, 12H), 0.00 (s, 6H).

Preparation of 86:

A mixture of 85 (2.41 g, 3.47 mmol) and NaI (0.624 g, 4.16 mmol) in acetone was refluxed for 3 h. Solvent was removed under reduced pressure and resulting residue was purified by column chromatography over silica gel to furnish 86 (1.94 g, 88%).

¹H NMR (400 MHz in CDCl₃) δ 7.64 (m, 4H), 7.37–7.23 (m, 6H), 5.08 (t, J=12.0 Hz, 1H), 3.75 (m, 1H), 3.58 (m, 1H), 3.06 (t, J=8.0 Hz, 2H), 2.2 (m, 2H), 2.0 (m, 2H), 1.7 (m, 2H), 1.59 (s, 3H), 1.03 (s, 9H), 0.89 (s, 9H), 0.019 (s, 3H), 0.00 (s, 3H). ¹³C NMR (100 MHz in CDCl₃) δ145.1, 138.7, 121.0, 112.8, 75.8, 75.8, 71.3, 38.1, 36.8, 32.3, 31.0, 26.1, 25.9, 23.9, 20.6, 18.4, 17.7.

Preparation of 87:

To a solution of 18 (0.542 g, 2.0 mmol) in THF (10 ml) n-BuLi (0.8 ml, 2.5 M solution in hexane) was added at –78° C. over a period of 1 h and the reaction mixture was stirred for 1 h. To this HMPA (0.35 ml) and iodo compound 86 (1.27 g, 2.0 mmol) in THF (5.0 ml) were added. Slowly raised the reaction mixture to –30° C. and stirred for 1 h. Saturated NH₄Cl was added at 25° C. and extracted with EtOAc (2×25 ml). Combined organic extracts were washed with water, brine and dried over (Na₂SO₄), evaporation of the organic solvent and purification by flash column chromatography over silica gel yielded 87 (1.01 g, 65%).

¹H NMR (400 MHz in CDCl₃) δ 7.67 (d, J=6.0 Hz, 4H), 7.37 (m, 6H), 5.08 (t, J=7.2 Hz, 1H), 4.3 (d, J=8.0 Hz, 1H), 3.65 (m, 1H), 3.48 (m, 1H), 3.2 (m, 2H), 2.9 (m, 1H), 2.1 (m, 2H), 1.8 (m, 10H), 1.65 (s, 3H), 1.28 (m, 2H), 1.01 (brs, 13H), 1.07 (d, 3H), 0.99 (m, 15H), 0.06 (s, 6H). ¹³C NMR (100 MHz in CDCl₃) δ 190.8, 136.3, 136.0, 134.4, 129.9, 129.85, 127.8, 122.8, 77.86, 77.5, 77.2, 73.1, 66.2, 59.5, 57.4, 48.4, 44.9, 36.0, 28.8, 27.5, 26.6, 26.3, 23.7, 20.8, 19.7, 19.66, 18.5, 15.7, –3.8, –3.9.

Preparation of 88:

A solution of 87 (350 mg, 0.45 mmol) in ether was cooled to –78° C. and was added LAH (0.5 ml, 1.0 M solution in diethyl ether). Reaction mixture was slowly brought to room temperature over a period of 1 h and saturated Na₂SO₄ was added. Reaction mixture was filtered and washed with water, brine and dried over (Na₂SO₄). Evaporation of the organic solvent and purification by flash column chromatography using silica gel gave 88 (200 mg, 88%).

¹H NMR (400 MHz in CDCl₃) δ 7.67 (m, 4H), 7.37 (m, 6H), 5.09 (t, J=7.8 Hz, 1H), 3.75 (m, 1H), 3.63 (m, 3H), 2.05–1.83 (m, 5H), 1.56 (s, 3H), 1.21 (m, 2H), 1.1 (d, J=6.0 Hz, 3H), 1.05 (s, 9H), 0.98 (d, J=8.0 Hz, 3H), 0.87 (s, 9H), 0.04 (s, 3H), 0.02 (s, 3H).

Preparation of 21:

Alcohol 88 (₂₀₀ mg) was dissolved in dichloromethane (10 ml). DMSO (1.0 ml), Et3N (2.0 ml) and SO₃.py complex (300 mg, 2.0 mmol) were added at 25° C., and the resulting mixture was stirred for 30 min. Saturated aqueous NH₄Cl solution (5.0 ml) and ether (20 ml) were added sequentially. The organic phase was washed with brine, dried over (Na₂SO₄). Evaporation of the organic solvent and purification by flash column chromatography using silica gel gave 21 (120 mg).

Preparation of 90:

To a mixture of CuBr.DMS (4.1 g, 20 mmol), ether (25 ml) and dimehtyl sulfide (20 ml), 0.5 M solution of butenyl magnesium bromide (3.8 g,40 mmol) in ether was added over a period of 10 min at –45° C. Reaction was stirred at this temperature for 2.5 h and propyne (1.1 ml, 20 m. mol) was added. This reaction mixture was stirred at –25° C. for 3 h and cooled to –78° C. To this 1-lithio pentyne (prepared from 20 mmol pentyne, 20 mmol n-BuLi and 20 mmol HMPA) in ether (20 ml) was added and stirred at –78° C. for 1 h. To this epoxide (7.0 g, 20 mmol) was added and the reaction mixture was stirred at –78° C. for 3 h and at –25° C. for 24 h. Aqueous NH₄Cl was added and extracted with ether (2×100 ml). Combined organic layer was washed with water, brine and dried (Na₂SO₄). Evaporation of organic solvent and purification by flash column chromatography gave the product 90 (3.03 g, 55%).

¹H NMR (400 MHz in CDCl₃) δ 7.6 (d, J=8.0 Hz, 4H), 7.31 (m, 6H), 5.6–5.48 (m, 1H), 4.98 (t, J=8.2 Hz, 1H), 4.85 (dd, J=14.0, 12.0 Hz, 2H), 3.75 (m, 1H), 3.5 (m, 1H), 1.98–1.97 (m, 6H), 1.58 (s, 3H), 0.99 (s, 9H), 0.95 (d, J=8.8 Hz, 3H).

Preparation of 92:

To a solution of 90 (3.03 g, 7.03 mmol) in dichloromethane (20 ml), 2,6-lutidine (1.0 ml, 8 mmol) and TBDMSOTf (1.6 g, 8 mmol) and stirred at 0° C. for 2 h. Diluted with CH₂Cl₂ (20 ml) and was washed successively with 10% aqueous HCl, water (20 ml) and brine. The organic layer was dried (Na₂SO₄). Evaporation of organic solvent and purification by flash column chromatography gave the product 92 (3.44 g, 96%).

¹H NMR (400 MHz in CDCl₃) δ 7.63 (m, 4H), 7.32 (m, 6H), 5.7 (m, 1H), 5.02 (t, J=7.2 Hz, 1H), 4.85 (dd, J=14.0, 8.0 Hz, 2H), 2.18–1.88 (m, 6H), 1.58 (s, 3H), 1.0 (s, 9H), 0.91 (d, J=8.0 Hz, 3H), 0.82 (s, 9H), –0.01 (s, 3H), –0.01 (s, 3H).

To a stirred solution of 92 (2.56 g) and tert. BuOH and water (1:1), AD-mix-□was added. Reaction mixture was stirred at room temperature for 10 h. The volume of the reaction mixture was reduced to ¼ by evaporating under vacuum. Diluted with ethylacetate (25 ml) and washed with water, brine, dried (Na₂SO₄). Evaporation of organic solvent and purification by flash column chromatography gave the corresponding diol (2.268 g, 75%).

¹H NMR (400 MHz in CDCl₃) δ7.65 (m, 4H), 7.38–7.22 (m, 6H), 5.08 (t, J=14, 8.2 Hz, 1H), 3.78 (m, 1H), 3.52–3.6 (m, 3H), 3.35 (m, 1H), 2.04–1.99 (m, 4H), 1.6 (s, 3H), 1.23 (m, 2H), 1.02 (s,9H), 0.93 (d, J=8.0 Hz, 3H), 0.84 (s, 9H), 0.022 (s, 3H), 0.00 (s, 3H).

Preparation of 94:

To a solution of diol obtained in the above step (2.04 g, 3.75 mmol) in 1:1 mixture of THF/H₂O (20 ml) sodiumperiodate was added and the mixture was stirred at 25° C. for 30 min. Reaction mixture was diluted with ether and washed with water, brine, dried over (Na₂SO₄). Organic solvent was removed and the residue was dissolved in methanol (10 ml) and cooled to 0° C. To this sodium borohydride (144 mg, 3.8 mmol) was added and stirred at 0° C. for 1 h. Water was added and extracted with ether (2×25 ml). Combined organic layer was washed with water, brine, dried(Na$_2$SO$_4$). Evaporation of organic solvent and purification by flash column chromatography gave the primary alcohol 94 (1.5 g, 80%).

$^1$H NMR (400 MHz in CDCl$_3$) δ 7.64 (m, 4H), 7.3 (m, 6H), 5.08 (t, J=8.2 Hz, 1H), 3.75 (m, 1H), 3.58 (m, 1H), 3.52 (t, J=14.0 Hz, 2H), 2.09–1.95 (m, 4H), 1.61 (s, 3H), 1.19 (s, 9H), 1.01 (d, J=8.0 Hz, 3H), 0.84 (s, 9H), 0.021 (s, 3H), 0.00 (s, 3H).

Preparation of 115:

Ozone was bubbled through a solution of citronellene, 114 (10 g, 72.46 mmol) in dichloromethane (500 ml) at −78° C. Reaction progress was monitored by the concentration of citronellene. After 6 h argon was bubbled through the reaction micture to remove the excess ozone. MeOH (10 ml) was added followed by the addition of sodium borohydride (5.7 g, 155 mmol) and the reaction micture was slowly brought to room temperature and stirred for 2 h. Water was added to the reaction mixture and extracted with ether (2×500 ml), washed with water, brine, and dried (Na$_2$SO$_4$). Organic solvent was removed at room temperature and the residue was purified by flash column chromatography (pentane and ether) to afford the alcohol 115 (6.7 g, 81%).

$^1$H NMR (400 MHz in CDCl$_3$) δ 5.7 (dq, J=4.1, 6 Hz, 1H); 4.96 (dd, J=6.2, 8 Hz, 2H), 3.65 (t, J=6.1 Hz, 2H), 2.15 (m, 1H), 1.58 (m, 2H), 1.4 (brs, 1H), 1.3 (d, J=6 Hz, 3H). $^{13}$C NMR (100 MHz in CDCl$_3$) δ 148, 113.4, 37.7, 35, 34.2, 31.1, 20.4.

Preparation of 116:

p-Toluenesulfonyl chloride (7.7 g, 40 mmol) was added to a stirred and ice cold solution of 4(S)-4-methyl -5-ene-1-ol (115) in dry pyridine (25 ml). The mixture was stirred for 1.5 h at 0–5° C. Then it was poured into ice cooled water and extracted with ether. The ether solution was washed with water, CuSO$_4$ aq,NaHCO$_3$ aq, and brine. Dried(Na$_2$SO$_4$) and the solvent was removed to give 8.2 g of crude tosylate. The crude product was disolved in acetone (100 ml), LiBr (7.2 g) was added to the solution and the mixture was stirred and heated at reflux for 1.5 h and then stirred at room temparature for 10 h. It was poured into icecooled water and extracted with ether (2×100). The ether solution was washed with water, NaHCO$_3$ aq, brine, and dried(Na$_2$SO$_4$) and solvent was removed at room temperature. The residue was distilled to give bromide 116 (4.46 g, 75.6%).

$^1$H NMR (400 MHz in CDCl$_3$) δ 5.6 (m, 1H), 4.9 (dd, J=6, 8 Hz,2H), 3.32 (t, J=7 Hz, 2H), 2.07 (m, 1H), 1.77 (m, 2H), 1.38 (m, 2H), 0.94 (d, J=7 Hz). $^{13}$C NMR (100 MHz in CDCl$_3$) δ 144.3, 113.5, 37.6, 35.41, 34.25, 31.01, 20.66.

Preparation of 118:

To a mixture of CuBr.DMS complex (4.1 g, 20 mmol), ether (25 ml) and dimehtyl sulfide (20 ml) S-4-methyl-hexyl-5-enyl magnesium bromide (3.8 g, 40 mmol) in ether was added over a period of 5 min at −45° C. Reaction was stirred at this temperature for 2.5 h and propyne (2.5 ml, 40 mmol) was added. This reaction mixture was stirred at −25° C. for 3 h and cooled to −78° C. To this 1-lithio pentyne (prepared from 40 mmol pentyne, 40 mmol of n-BuLi and 40 mmol HMPA) in ether (20 ml) was added and stirred at −78° C. for 1 h. To this epoxide (4.04 g, 40 mmol) was added and the reaction mixture was stirred at −78° C. for 3 h and at −25° C. for 24 h. NH$_4$Cl aq was added and extracted with ether (2×100 ml). Combined organic layer was washed with water, brine and dried (Na$_2$SO$_4$). Evaporation of organic solvent and purification by flash column chromatography gave the product 118 (4.51 g, 65%).

$^1$H NMR (400 MHz in CDCl$_3$) δ 5.6 (m, 1), 5.16 (dd, J=6, 6.1 Hz, 2H), 4.9 (t, J=8 Hz, 1H), 3.72 (m 1H), 3.5 (m, 1H), 2.07 (m, 4H), 1.98 (m, 1H), 1.6 (s, 3H), 1.2 (m, 2H), 1.15 (m, 2H), 1.04 (d, J=7 Hz, 3H), 0.91 (d, J=7.2 Hz, 3H), 0.82 (s, 9H), 0.00 6 (s, 6H). $^{13}$C NMR (100 MHz in CDCl$_3$) δ 157.5, 148.3, 145, 144.1, 135.1, 122, 77.6, 73.9, 70.1, 55.14, 54.26, 45.64, 17.48, −0.02, −0.01.

Preparation of 120:

To a suspension of NaH (240 mg, 5 mmol) in DMF (5 ml), compd 118 (1.6 g, 5 mmol) in DMF (10 ml) was added and stirred at room temperature for 30 min. Then p-methoxybenzyl bromide was added and stirred at room temperature for 3 h. Water was added slowly and extracted with ethylacetate (2×25 ml). Combined organic layer was washed with water, NaCl aq and dried (Na$_2$SO$_4$). Evaporation of solvent and purification by column chromatography gave the product 120 (1.84 g, 81%).

$^1$H NMR (400 MHz in CDCl$_3$) δ 7.21 (d, J=8 Hz, 2H); 6.82 (d, J=8.1 Hz, 2H) 5.6 (m, 1H) 5.17 (t, J=6.1 Hz, 1H), 4.85 (m, 2H), 4.5 (m, 2H), 3.75 (m, 4H), 3.2 (m, 1H), 2,12 (m, 1H), 2.1(m, 4H), 1.62 (s, 3H), 1.19 (m, 2H), 1.123 (m, 2H), 1.08 (d, J=8 Hz, 2H) 0.93 (d, J=7.8 Hz, 2H), 0.84 (s, 9H), 0.007 (s, 3H), 0.00 (s, 3H). $^{13}$C NMR (100 MHz in CDCl$_3$) δ164.1, 161.41, 157.15, 148.3, 145, 144.51, 135.1, 122, 77.6, 73.9, 70.1, 55.14, 54.26, 45.64, 17.48, −0.028, −0.019.

A mixture of water (5 ml), t-butanol (5 ml) and compd 120 (1.8 g, 4 mmol) was added AD-mix-α 6 g) at room temperature. Reaction mixture was stirred at room temparature for 12 h. The volume of the reaction mixture was then reduced to half and extracted with ethyl acetate (2×25 ml). The combined organic layer was washed with water, NaCl aq and dried (Na$_2$SO$_4$). Evaporation of the solvent and purification by flash column chromatography afforded corresponding diol, 1.542 g (78%).

$^1$H NMR (400 MHz in CDCl$_3$) δ 7.21 (d, J=8 Hz, 2H); 6.82 (d, J=7.8 Hz); 5.17 (t, J=6.1 Hz, 1H); 4.48 (dd, J=8, 14 Hz; 2H); 3.75 (s, 3H); 3.7 (m, 1H), 3.48 (m, 1H), 3.39 (m, 2H), 3.2 (m, 1H); 2.11 (m, 1H), 1.94 (m, 4H), 1.61 (s, 3H), 1.48–1.2 (m, 4H), 1.06 (d, J=6.2 Hz, 3H), 0.84 (s, 9H); 0.825 (d, J=6 Hz, 3H), 0.0085 (s, 3H), −0.0119 (s, 3H).

Preparation of 122:

To a solution of diol (988 mg, 2 mmol) in THF(5 ml) and water (5 ml) powdered sodiumperiodate was added at room temperature. It was allowed to stirr for 1 h and diluted with ether and organic layer was separated. Organic layer was washed with water, NaCl aq and dried (Na$_2$SO$_4$). Evaporation of the solvent and purification by flash chromatography afforded aldehyde (0.728 g, 85%).

$^1$H NMR (400 MHz in CDCl$_3$) δ 9.1 (d, J=6 Hz, 1H,); 7.21 (d, J=8 Hz, 2H,)); 6.82 (d, J=7.8 Hz,); 5.17 (t, J=6.1 Hz, 1H); 4.48 (dd,J=8, 14 Hz; 2H,); 3.75 (s, 3H); 3.7 (m, 1H)−); 3.2 (m, 1H); 2.11 (m, 1H), 1.94 (m, 4H), 1.61 (s, 3H,) 1.48–1.2 (m, 4H), 1.06 (d, J=6.2 Hz, 3H), 0.84 (s, 9H), 0.825 (d, J=−6 Hz, 3H,) 0.0085 (s, 3H,) −0.0119 (s, 3H).

p-Toluene sulfonylchloride (36 g, 0.24 mol) was added to a stirred and ice cooled solution of alcohol (20 g, 0.2 mol) in dry pyridine (150 ml). The mixture was stirred for 1.5 h at 0–5° C. Then it was poured into icewater and extracted with ether (2×100 ml). Combined organic layer was washed with water, CuSO$_4$ aq, NaHCO$_3$ aq,NaCl aq and dried (Na$_2$SO$_4$). Evaporation of the organic solvent gave 48 g of crude product.

$^1$H NMR (400 MHz in CDCl$_3$) δ 7.7 (dd, j=8.12 Hz, 2H); 7.33 (d, J=8.2 Hz); 4.68 (s, 1H); 4.58 (s, 1H), 4.02 (t, J=6.4, 6.43 Hz; 2H); 2.43 (s, 3H,); 2.01 (t, j=7.4 Hz, 2H), 1.75 (t, J=8 Hz, 14 Hz; 2H), 1.64 (s, 3H).

Preparation of 123:
Tosylate (48 g, o.188 mol) was dissolved in acetone (500 ml) and solid LiBr (19.5 g, 0.226 mol) was added. The mixture was heated under reflux for 1.5 h and then stirred for 10 h. It was poured into ice water and extracted with ether (2×250 ml). The combined orgnic layer was washed with water, NaHCO$_3$ aq, NaCl aq and dried (Na$_2$SO$_4$). The organic solvent was removed at room temperature and the residue was distlled to give 123 (22. 84 g, 76%).

$^1$H NMR CDCl$_3$, 400 Mhz) δ 4.76 (s, 1H); 4.72 (s, 1H,); 3.4 (t, J=6.7, 6.5 Hz; 2H); 2.16 (t, j=7, 7.6 Hz; 2H),2.01 (m, 1H); 1.7 (s, 3H). $^{13}$C NMR (CDCl$_3$ 400M Hz). 144.31, 111.39, 36.439, 33.65, 30, 29.9, 22.68.

Preparation of 124:
To a mixture of CuBr.DMS complex (4.1 g, 20 mmol), ether (25 ml), dimethylsulfide (20 ml) at −45° C. was added a 0.46 M solution of grignard (43.0 ml, 20.0 mmol) in ether over a period of 10 min. After 2 h, propyne (1.1 ml, 20.0 mmol) which has been condensed by the cold finger at −45° C. was added. The mixture was stirred at −23° C. for 2.5 h and the resulting green solution was cooled to −78° C. A solution of 1-lithiopentyn [prepared from 20.0 mmol of pentyne and 20.0 mmol of n-BuLi in ether (20 ml)] and HMPA was transferred to the green solution. After 1 h, epoxide (4.16 g, 20.0 mmol) in ether (10 ml) was added over a 5 min period. The resulting mixture was stirred at −78° C. for 3 h and at −25° C. for 24 h. Quenched the reaction at 0° C. by addition of saturated NH$_4$Cl solution (10 ml), adjusted the pH 8.0 with aqueous ammonia solution and partitioned between water and ether. The crude product was purified by flash column chromatography to yield (4.7 g, 72%).

$^1$H NMR (400 MHz in CDCl$_3$) δ 5.16 (t, J=14.0 Hz, 1H), 4.71 (s, 1H), 4.64 (s, 1H), 3.78 (m, 1H), 3.48 (m, 1H), 2.07 (t, J=10 Hz, 2H), 1.94 (m, 4H), 1.65 (s, 3H), 1.48 (m, 2H), 1.03 (d, J=8.0 Hz, 3H), 0.82 (s, 9H), 0.006 (s, 3H), 0.00 (s, 3H).

Preparation of 125:
To a solution of 124 (3.26 g, 10.0 mmol) in dichloromethane (10 ml), 2,6-lutidine (1.28 ml) and TMSOTf (2.23 ml, 10.0 mmol) were added at 0° C. Reaction mixture was stirred at 0° C. for 1 h and aqueous NaHCO3 solution was added. Extracted with ether (2×50 ml). Combined organic layer was washed with water, brine and dried over (Na$_2$SO$_4$). Evaporation of the organic solvent and purification by flash column chromatography using silica gel gave 125 (3.78 g, 95%).

$^1$H NMR (400 MHz in CDCl$_3$) δ 5.16 (t, J=8.0 Hz, 1H), 4.71 (s, 1H), 4.68 (s, 1H), 3.78 (m, 1H), 3.45 (m, 1H), 1.91 (m, 2H), 1.8 (m, 4H), 1.41 (m, 2H), 1.01 (d, J=6.8 Hz, 3H), 0.79 (s, 9H), −0.02 (s, 3H), −0.047(s, 3H).

Preparation of 126:
To a stirred solution of 125 (3.18 g, 8.0 mmol) in THF (10 ml) at 25° C., (ipc)$_2$BH (2.28 g, 8.0 mmol) in THF was added. Reaction mixture was stirred at 25° C. for 1 h and quenched with NaOH and H$_2$O$_2$ (10.0 mmol each). Extracted with ether and washed with water, brine, dried over (Na$_2$SO$_4$). Evaporation of the organic solvent and purification by flash column chromatography using silica gel gave 126 (2.8 g, 85%).

$^1$H NMR (400 MHz in CDCl$_3$) δ 5.11 (t, J=8.2 Hz, 1H), 3.75 (m, 1H), 3.45 (m, 1H), 3.4 (m, 2H), 2.12 (m, 2H), 1.9 (m, 4H), 1.59 (s, 3H), 1.43 (m, 1H), 1.41 (m, 1H), 1.01 (d, J=8.4 Hz, 3H), 0.83 (d, J=6.8 Hz, 3 H), 0.79 (s, 9H), −0.015 (s, 3H), −0.046 (s, 3H).

Preparation of 100:
To a solution of (2.08 g, 5.0 mmol) in CH$_2$Cl$_2$ (20 ml) and DMSO (2 ml) at 0° C., was added triethylamine ((2.0 ml) and SO$_3$.py complex (1.59 g, 10.0 mmol) and the resulting mixture was stirred at 0° C. for 90 min. Reaction mixture was quenched by addition of aqueous NH$_4$Cl (2.0 ml) and extracted with diethyl ether (2×25 ml). Combined organic extracts was washed with water, brine dried over (Na$_2$SO$_4$). Evaporation of the organic solvent and purification by flash column chromatography using silica gel gave aldehyde (1.73 g, 84%).

$^1$H NMR (400 MHz in CDCl$_3$) δ 9.52 (s, 1H), 5.1 (t, J=6.5 Hz, 1H), 3.5 (m, 1H), 3.29 (dt, J=5.2, 4.0 Hz, 1H), 2.21 (dd, J=4.8, 3.6 Hz, 2H), 2.08 (m, 1H), 1.94 (m, 2H), 1.61 (s, 3H), 1.32 (m, 2H), 1.01 (d, 6H), 0.79 (s, 9H), 0.065 (s, 3H), −0.025 (s, 3H).

Preparation of 5c:
To a suspension of NaH (0.96 g, 20 mmol) in THF (20 ml), cooled to 0° C., was added epoxy alcohol (1.76 g, 20 mmol) in THF (10 ml). It was allowed to stir at 0° C. for 30 min and p-methoxy benzylbromide was added slowly. Reaction was quenched with cooled water and extrcted with ethyl acetate (2×25 ml). Combined organic layer was washed with water, NaCl aq and dried (Na$_2$SO$_4$). Evaporation of the organic solvent and purification by column chromatography afforded 5c 3.5 g (87%).

$^1$H NMR (CDCl$_3$,400 M Hz). 7.25 (d, J=8 Hz, 2H) 6.87 (d, J=8.1 Hz, 2H)), 4.55 (dd, j=12, 8 Hz; 2H),3.79 (s, 3H,); 3.4–3. 38 (dq,J=8, 5.6 Hz, 1H,); 2.92 (dq, J=1.4, 0.8 Hz, 2.78 (dd, J=4.7, 3.9 Hz, 1H); 2.68 (dd, J=2.3, 2.58 Hz, 1H); 1.28 (d, J=6.3 Hz, 3H). $^{13}$C NMR (CDCl$_3$ 400M Hz). 159.18, 130.52, 129.06, 113.77, 73.9, 70.94, 55.15, 54.26, 45.64, 17.48.

Preparation of 130:
To a mixture of CuBr.DMS complex (4.1 g, 20 mmol), ether (25 ml), and dimethyl sulfide (20 ml) at −45° C. was added a 0.46 M solution of grignard reagent (43 ml, 20 mmol) in ether over a period of 5 min. After 2 h, propyne (1.1 ml, 20 mmol) which had been condensed by cooled finger, at −45° C. was added. The reaction mixture was stirred at −23° C. for 2.5 h and the resulting dark green solution was cooled to −78° C. A solution of 1-lithiopentyne (prepared from pentyne(20 mmol) and n-BuLi (20 mmol) in ether (20 ml)and HMPA (20 mmol) was transfored to the green solution. Aftr 1 h epoxide (4.16 g, 20 mmol) in ether (10 ml) was added over a 5 min period. the resultin mixture was stirred at −78° C. for 3 h and then at −25° C. for 24 h, quenched at 0° C. by addition of NH$_4$Cl aq (pH adjusted to 8 by NH$_4$OH) and paritioned between water and ether. The crude product was purified by flash column chromatography to yield 130 4.7 g(72%) product.

$^1$H NMR (CDCl$_3$,400 M Hz δ 7.26 (d, J=7.5 Hz, 2H)), 6.88 (d, 2H, J=8.1 Hz, 2H), 5.17 (t, J=8.2 Hz, 1H), 4.7 (s, 1H), 4.67 (s, 1H) 4.45 (dd, J=12, 8 Hz; 2H), 3.8 (s, 3H,), 3.71 (m, 1H, −), 3.5 (m, 1H), 2.18 (m, 2H), 2.01 (m, 4H), 1.71 (s, 6H), 1.26 m, 2H); 1,17 (d, J=6.19, 3H). $^{13}$C NMR (CDCl$_3$ 400M Hz). 100.8, 95.4, 88.4, 79.9, 71.93, 65.48, 61.76, 31.2, 30.96, 27.53, 24.79,10.57.

Preparation of 129:
To a solution of alcohol (4.7 g, 14.1 mmol) in dichloromethane (25 ml) was added 2,6-lutidine (2 ml, 16 mmol) and t-Butyl trifluoromethanesulfonate (3.2 g, 16 mmol and stirred at 0oC for 2 h. Diluted with dichloromethane (25 ml) and washed with 10% aq Hydrochloric acid followed by water and NaCl aq and dried(Na$_2$SO$_4$). Organic solvent was evaparated and the resulting crude product was purified by flash column chromatography to afford 129 (5.9 g,95%). $^1$H NMR (CDCl$_3$,400 M Hz δ 7.25 (d, J=6.8 Hz, 2H), 6.88 (d, J=8.5 Hz, 2H), 5.17 (t, J=6.8 Hz, 1H), 4.7 (s, 1H), 4.67 (s, 1H), 4.48 (dd, J=8, 6.5 Hz; 2H), 3.8 (s, 3H), 3.71 (m, 1H), 3.5 (m, 1H), 2.18 (m, 2H), 2.03 (m, 4H), 1.72 (s, 3H,), 1.71 (s, 3H), 1.52 (m, 2H), 1.15 (d, J=8 Hz, 3H), 0.93 (s, 9H), 0.0064 (s, 6H). $^{13}$C NMR (CDCl$_3$ 400M Hz). 146.26, 136.92, 131.642, 129.52, 122.22, 114.06, 110.2, 110, 75.746, 77.11, 71, 55.64, 38.170, 32.62, 32, 26.35, 23.89, 22.817, 18.59, 15.525.

Preparation of 130:

To a mixture of compound 129 (4.46 g, 10 mmol), dichloromethane (40 ml) and water (8 ml), was added DDQ (2.27 g, 10 mmol). Reaction mixture was stirred at 25° C. for 30 min and the pricipitate was filtered The filterate was wahed NaHCO$_3$ aq, NaCl aq and dried (Na$_2$SO$_4$). Evaporation of the organic solvent and purification by column chromatography gave 130 (2.8 g, 88%).

$^1$H NMR (CDCl$_3$,400 M Hz δ 5.17 (t, J=6.8 Hz, 1H); 4.7 (s, 1H, —C(CH$_3$)=CH$_2$), 4.67 s, 1H, -), 3.8 (m, 1H), 3.6 (m, 1H), 2.15 (m, 2H), 2.04–1.9 (m, 4H), 1.71 (s, 3H), 1.69 (s, 3H), 1.51 (m, 2H), 1.1 (d, 3H, J=7 Hz), 0.89 (s, 9H), 0.06 (s, 6H). $^{13}$C NMR (CDCl$_3$ 400M Hz). 146.15, 137.44, 121.81, 110.266, 77.727, 77.409, 77.09, 70.715, 38.1, 31.96, 30.7, 26.3, 23.8, 22.7, 18.4, 17.562, –0.06.

Preparation of 131:

Alcohol 130 (2.8 g, 8.5 mmol) was dissolved in dichloromethane (45 ml), DMSO (24 ml), Et$_3$N (4.2 ml, 42 mmol), and SO$_3$.Py (2.7 g, 17 mmol) was added at 0° C. and the resulting mixture was stirred at room temperature for 6 h. NH$_4$Cl aq and ether were added sequentially. The organic layer was washed with water, NaCl aq and dried (Na$_2$SO$_4$) and the solvent was evaparated under reduced pressure. Purified by flash column chromatography furnished ketone 131 (1.59 g, 58%).

$^1$H NMR (CDCl$_3$,400 M Hz δ 5.17 (t, J=7.2 Hz, 1H), 4.7 (s, 1H), 4.66 (s, 1H), 3.97 t, J=6.8 Hz, 1H), 2.25 (m, 2H), 2.14 (s, 3H), 1.7 (s, 3H), 1,68 (s, 3H), 1.4 (m, 2H), 0.94 (s, 9H),0.04 (s, 6H). $^{13}$C NMR (CDCl$_3$ 400M Hz). 212.3, 146.1, 138.6, 119.7, 79.5, 77.7, 77.4, 77.0, 38.03, 33.74, 31.9, 26.6, 26.1, 25.7, 23.84, 22.77, 18.5.

Preparation of 132:

Phosponate 24 (1.8 g, 7.6 mmol) was dissolved in dimethoxy ethane (20 ml) and the solution was cooled to −78° C. n-BuLi 3.04 ml, 2.5 M in hexane) was slowly added and the resulting mixture was stirred for 45 min before ketone (1.58 g, 4.8 mmol) in dimethoxyethane (10 ml) was added at the same temparature. Stirring was continued for another 10 h at room temparature and then the reaction mixture was quenched with NH$_4$Cl aq (25 ml). Ethylacetate was added and the organic phse was separated and washed with water, NaCl aq and dried (Na$_2$SO$_4$) Evaporation of the organic solvent and purification by flash column chromatography afforded compound 1.58 g (75%).

$^1$H NMR (CDCl$_3$,400 M Hz δ 6.9 (s, 1H,), 6.64 (s, 1H); 5.17 (t, J=6.4 Hz, 1H), 4.66 (s, 1H), 4.64 (s, 1H), 4.15 (t, J=6.2, 8 Hz, 1H), 2.7 (s, 3H), 2.2 (m, 2H), 2.0–1.99 (m, 4H); 1.7 (s, 3H); 1.67 (s, 3H); 0.88 (s, 9H) 0.047 (s, 3H); 0.0032 (s,6H). $^{13}$C NMR (CDCl$_3$ 400M Hz). 153, 146.2, 142,9, 137, 122.1, 119, 115.3, 110.1, 79.4, 77.7, 77.1, 38.1, 35.7, 32, 26.4, 26, 26.24, 23.8, 22.8, 19.5, 18.63, 14.32.

Preparation of 133:

To a solution of compound 132 (419 mg, i mmol) in THF (2 ml), (ipc)$_2$BH (286 mg, 1 mmol) in THF (2 ml) was added and the reaction was stirred for 1 h at 25° C. Distilled water and Sodiumperborate (160 mg, 1.1 mmol) were added sequentially and stirred for 1 h. Extracted with ethyl acetate and washed with water, NaCl aq and dried (Na$_2$SO$_4$). Evaparation of the organic solvent and purification by flash column chromatography gave alcohol 133.

$^1$H NMR (CDCl$_3$,400 M Hz δ 6.91 (s, 1H); 6.44 (s, 1H,); 5.17 (t, J=6.4 Hz, 1HCH$_2$—); 4.18 (t, J=6.2, 8 Hz, 1H); 3.5 (m, 2H), 2.7 (s, 3H), 2.25 (m, 2H),1.9 (m, 5H), 1.66(s, 3H); 1.4 (m, 2H); 0.92 (dJ=8 Hz, 3H);0.88 (s, 9H,); 0.004 (s, 3H); –0.005 (s, 3H).

Preparation of 134:

To a solution of copound 133 (437 mg, 1 mmol) in dichloromethane (10 ml), DMSO 1 ml) and Et$_3$N (0.5 ml, 5 mmol) Py.SO$_3$ complex (300 mg, 2 mmol) was added and allowed to stirr at 25° C. for 2 h. Reaction mixture was qunched with NH$_4$Cl aq and extracted with diethyl ether (2×25 ml). Combined organic layer was washed with water, NaCl aq and dried (Na$_2$SO$_4$). Organic solvent was removed under reduced pressure and flash chromatography purification afforded the aldehyde 201 mg (52%).

$^1$H NMR (CDCl$_3$,400 M Hz □ 9.6 (d, J=6 Hz, 1H), 6.92 (s, 1H); 6.44 (s, 1H); 5.16 (dd, J=6.7, 6.4 Hz, 1H,); 4.08 (t, J=6.5, 5.1 Hz); 2.7 (s, 3H); 2.36–2.18 (m, 3H), 1.99 (3H), 1.71–1.64 (m, 4H); 1.43–1.3 (m, 2H); 1.08 (d, J=8 Hz, 3H); 0.88 (s, 9H), 0.03 (s, 3H), –0.004 (s, 3H). $^1$H NMR (CDCl$_3$,400 M Hz δ 205, 164.4, 153.11, 142.3, 135.7, 122, 118.1, 114.8, 46.1, 25.7, 22, 18.6, 13.8, 13.2, –0.05. –0.01,

Preparation of 124:

To a mixture of CuBr.DMS complex (4.1 g, 20 mmol), ether (25 ml), dimethylsulfide (20 ml) at −45° C. was added a 0.46 M solution of grignard (43.0 ml, 20.0 mmol) in ether over a period of 10 min. After 2 h, propyne (1.1 ml, 20.0 mmol) which has been condensed by the cold finger at −45° C. was added. The mixture was stirred at −23° C. for 2.5 h and the resulting green solution was cooled to −78° C. A solution of 1-lithiopentyn [prepared from 20.0 mmol of pentyne and 20.0 mmol of n-BuLi in ether (20 ml)] and HMPA was transferred to the green solution. After 1 h, epoxide (4.16 g, 20.0 mmol) in ether (10 ml) was added over a 5 min period. The resulting mixture was stirred at −78° C. for 3 h and at −25° C. for 24 h. Quenched the reaction at 0° C. by addition of saturated NH$_4$Cl solution (10 ml), adjusted the pH 8.0 with aqueous ammonia solution and partitioned between water and ether. The crude product was purified by flash column chromatography to yield (4.7 g, 72%).

$^1$H NMR (400 MHz in CDCl$_3$) δ 5.16 (t, J=14.0 Hz, 1H), 4.71 (s, 1H), 4.64 (s, 1H), 3.78 (m, 1H), 3.48 (m, 1H), 2.07 (t, J=10 Hz, 2H), 1.94 (m, 4H), 1.65 (s, 3H), 1.48 (m, 2H), 1.03 (d, J=8.0 Hz, 3H), 0.82 (s, 9H), 0.006 (s, 3H), 0.00 (s, 3H).

To a solution of 124 (3.26 g, 10.0 mmol) in dichloromethane (10 ml), 2,6-lutidine (1.28 ml) and TMSOTf (2.23 ml, 10.0 mmol) were added at 0° C. Reaction mixture was stirred at 0° C. for 1 h and aqueous NaHCO3 solution was added. Extracted with ether (2×50 ml). Combined organic layer was washed with water, brine and dried over (Na$_2$SO$_4$). Evaporation of the organic solvent and purification by flash column chromatography using silica gel gave 125 (3.78 g, 95%).

$^1$H NMR (400 MHz in CDCl$_3$) δ 5.16 (t, J=8.0 Hz, 1H), 4.71 (s, 1H), 4.68 (s, 1H), 3.78 (m, 1H), 3.45 (m, 1H), 1.91 (m, 2H), 1.8 (m, 4H), 1.41 (m, 2H), 1.01 (d, J=6.8 Hz, 3H), 0.79 (s, 9H), –0.02 (s, 3H), –0.047(s, 3H).

Preparation of 126:

To a stirred solution of 125 (3.18 g, 8.0 mmol) in THF (10 ml) at 25° C., (ipc)$_2$BH (2.28 g, 8.0 mmol) in THF was added. Reaction mixture was stirred at 25° C. for 1 h and quenched with NaOH and H$_2$O$_2$ (10.0 mmol each). Extracted with ether and washed with water, brine, dried over (Na$_2$SO$_4$). Evaporation of the organic solvent and purification by flash column chromatography using silica gel gave 126 (2.8 g, 85%).

$^1$H NMR (400 MHz in CDCl$_3$) δ 5.11 (t, J=8.2 Hz, 1H), 3.75 (m, 1H), 3.45 (m, 1H), 3.4 (m, 2H), 2.12 (m, 2H), 1.9

(m, 4H), 1.59 (s, 3H), 1.43 (m, 1H), 1.41 (m, 1H), 1.01 (d, J=8.4 Hz, 3 H), 0.83 (d, J=6.8 Hz, 3 H), 0.79 (s, 9H), −0.015 (s, 3H), −0.046 (s, 3H).

Preparation of 100:

To a solution of (2.08 g, 5.0 mmol) in $CH_2Cl_2$ (20 ml) and DMSO (2 ml) at 0° C., was added triethylamine ((2.0 ml) and $SO_3$.py complex (1.59 g, 10.0 mmol) and the resulting mixture was stirred at 0° C. for 90 min. Reaction mixture was quenched by addition of aqueous $NH_4Cl$ (2.0 ml) and extracted with diethyl ether (2×25 ml). Combined organic extracts was washed with water, brine dried over ($Na_2SO_4$). Evaporation of the organic solvent and purification by flash column chromatography using silica gel gave aldehyde (1.73 g, 84%).

$^1$H NMR (400 MHz in $CDCl_3$) δ 9.52 (s, 1H), 5.1 (t, J=6.5 Hz, 1H), 3.5 (m, 1H), 3.29 (dt, J=5.2, 4.0 Hz, 1H), 2.21 (dd, J=4.8, 3.6 Hz, 2H), 2.08 (m, 1H), 1.94 (m, 2H), 1.61 (s, 3H), 1.32 (m, 2H), 1.01 (d, 6H), 0.79 (s, 9H), 0.065 (s, 3H), −0.025 (s, 3H).

Preparation of 135:

A solution of ketoacid 10 (69 mg, 0.028 mmol) in THF (2 ml) was added dropwise to a freshly prepared solution of LDA [prepared from diisopropylamine (57 uL, 0.47 mmol) and n-BuLi (188 uL, 2.5 M solution in hexane, 0.47 mmol)] at −78° C. After being stirred for 15 min the solution was allowed to warm to −40° C., and after 30 min it was cooled to −78° C. A solution of aldehyde 134 (82 mg, 0.18 mmol) was added dropwise and the resulting mixture was stirred for 15 min and then quenched at −78° C. by the slow addition of saturated aqueous $NH_4Cl$ solution. The reaction mixture was warmed to 0° C. and AcOH (0.2 ml) was added followed by the addition of EtOAc (5.0 ml). The organic layer was separated and the aqueous phase was extracted with EtOAc (3×5 ml). The combined organic layer was dried over ($Na_2SO_4$). Evaporation of the organic solvent afforded a mixture of aldol products 1:1 ratio and the unreacted ketoacid. The mixture was dissolved in dichloromethane (2.0 ml) and treated at 0° C. with 2,6-lutidine and tert.butyidimethylsilyl trifluoromethane sulfonate (0.42 ml, 0.18 mmol). After stirring for 2 h aqueous HCl (10% solution) was added and the resulting biphasic mixture was separated. The aqueous phase was extracted with dichloromethane (3×5 ml) and the combined organic phase was washed with brine, dried ($Na_2SO_4$) and concentrated under vacuum to give a mixture of tetra tert.butyidimethylsilyl ethers. The crude compound was dissolved in methanol (5 ml) and $K_2CO_3$ (140 mg, 0.1 mmol) was added at 25° C. The reaction mixture was vigorously stirred for 15 min and then filtered. The residue was washed with methanol (5 ml) and the solution was acidified with ion exchange resin (DOWEX 50 w x 8–200) to pH 4–5 and filtered again. The solvent was removed under reduced pressure and the resulting residue was dissolved in EtOAc and washed with saturated aqueous $NH_4Cl$ solution (5.0 ml). The aqueous phase was extracted with EtOAc (4×5 ml) and combined organic layer was washed with brine, dried over ($Na_2SO_4$). Evaporation of the organic solvent and purification by thin layer chromatography gave 135 (22 mg).

$^1$H NMR (400 MHz in $CDCl_3$) δ 6.91 (s, 1H), 6.58 (s, 1H), 5.15 (dd, J=7.4, 7.1 Hz, 1H), 4.6 (dd, 6.1, 5.2 Hz, 1H), 4.07 (m, 1H), 3.84 (dd, J=7.0, 5.2 Hz, 1H), 3.11 (dq, J=7.1, 6.5 Hz, 1H), 2.7 (s, 3H), 2.49 (m, 1H), 2.31 (m, 1H), 2.28–2.04 (m, 3H), 1.94 (s, 3H), 1.6 (s, 3H), 1.5 (m, 4H), 1.22 (s, 9H), 1.12 (s, 3H), 1.12 (m, 1H), 1.08 (d, J=6.0 Hz, 3H), 0.9–0.85 (m, 30H), 0.111 (s, 3H), 0.07 (s, 3H), 0.06 (s, 6H), 0.043 (s, 3H), −0.003(s, 3H).

Preparation of 12Z-Hydroxy Acid (136):

12Z-Carboxylic acid 135 (44 mg, 0.047 mmol) was converted to 12Z-hydroxy acid 136 (21 mg) according to the same procedure described for compound 55.

Macrolactonization of 136:

12Z-hydroxyacid was lactonized by using the same procedure outlined for the preparation for compound 46.

Preparation of β-Lactone 155:

To a cooled solution of ketoacid 56 (364 mg or 2 mmoL) in pyridine (3 mL) was added benzenesulfonyl chloride (528 mg or 3 mmoL). The reaction mixture was stirred under argon at 0°C. for 1 h and at −22° C. for 12 h. Ether was added (100 mL) and the mixture washed with water (50 mL), 5% aq. $CuSO_4$ (50 mL), brine (50 mL) and the organic layer was then dried over $Na_2SO_4$. Filtration and rotary evaporation of solvent provided an oil which was purified by silica gel (240–400 mesh) flash chromatography to give 155 as a colorless oil (221 mg or 70% yield). $^1$H NMR (400 MHz, $CDCl_3$): δ 4.60 (t, J=5.6 Hz, 1H), 3.46 (dd, J=6, 16 Hz, 1H), 3.22 (dd, J=6, 16 Hz, 1H), 2.52 (q, J=8, 12 Hz, 2H), 1.25 (s, 3H), 1.18 (s, 3H), 1.0 (t, J=8 Hz, 3H). $^{13}$C NMR (100 MHz, $CDCl_3$): δ213.4, 168.2, 74.6, 49.4, 40.0, 31.4, 20.4, 18.9, 8.0. IR (film), ν: 3022, 2976, 1831, 1705, 1634, 1467, 1333, 1126, 872, 756 cm$^{-1}$.

Preparation of Compound 167:

To a solutiion of compound 166 (6.64 g, 20 mmol) in dichloromethane and diisopropylethylamine (3.8 g, 30 mmol) trimethyl silyl ethoxy methyleneoxychloride (3.9 g, 24 mmol) was added at 0° C. The mixture was stirred at room temperature for 6 h. The reaction was quenched with aq. ammonium chloride and the mixture was extracted with ethyl acetate. The combined organic extracts were dried over anhydrous $Na_2SO_4$. and concentrated in vacuo. The residue was purified by column chromatography on silica gel using hexane/EtOAc to give the compound 167 (8.7 g, 94%). $^1$H NMR (400 MHz, $CDCl_3$): δ 7.26 (d, J=8 Hz, 2H); 6.88 (d, J=8.1 Hz, 2H); 5.13 (t, J=6.0 Hz, 1H); 4.76 (s, 1H); 4.69 (s, 1H); 4.65 (dd, J=12 Hz, 2H); 3.74 (dd, J=8 Hz, 1H); 3.67 (m, 1H); 3.54 (dd, J=8.2 Hz, 1H); 3.5 (s, 3H); 3.41 (m, 1H); 3.0 (d, J=6.0 Hz, 1H); 2.5 (m, 2H); 2.1 (m, 6H); 1.69 (s, 3H); 1.68 (s, 3H); 1.5 (m, 2H); 0.9 (t, J=6.0 Hz, 2H); 0.01 (s, 9H).

Preparation of Compound 168:

To a solution of compound 167 (8.7 g, 18.8 mmol) in dichloromethane and water (80:20 ml) was added DDQ (3.9 g, 20 mmol) at 0° C. and the reaction was stirred at room temperature for 2 h. After completion of the reaction it was extracted with dichloromethane (50 ml×3) and washed with aq. $NaHCO_3$ and brine solution. Organic phase was dried over $Na_2SO_4$.and evaporated under vacuo. The crude product was purified by flash chromatography on silica gel using hexane/EtOAc to give product 168 (5.46 g, 85%). $^1$H NMR (400 MHz, $CDCl_3$): δ5.15 (t, J=6.0 Hz, 1H); 4.65 (s, 1H); 4.64 (s, 1H); 4.6 (dd, J=8.0 Hz, 2H); 3.76 (dd, J=8.0 Hz, 1H); 3.57 (m, 2H); 3.38 (m, 1H); 3.0 (d, J=6.0 Hz, 1H); 2.34 (m, 1H), 2.3 (m, 1H); 2.02 (m, 6H); 1.72 (m, 2H); 1.69 (s, 3H); 1.68 (s, 3H); 1.4 (m, 2H); 0.9 (t, J=6.4 Hz, 2H); 0.012 (s, 9H).

Preparation of Compound 169:

To a solution of SO3.Py complex (4.044 g, 29 mmol), DMSO (4.6 ml, 60 mmol) and triethylamine (12.0 ml, 60 mmol) in dichloromethane (50 ml) was added compound 168 (5.1 g, 14.49 mmol). The reaction mixture was stirred at room temperature for 8 h. Reaction was quenched with sat. ammonium chloride 10.0 ml and extracted with ethyl acetate (25 ml×3). Combined organic extracts were dried over $Na_2SO_4$. and evapoated under vacuum. The crude product was purified by flash chromatography on silica gel using hexane/EtOAc to give product 169 (3.8 g, 78%). $^1$H NMR (400 MHz, $CDCl_3$): δ5.09 (t, J=8.0 Hz, 1 H); 4.71 (dd, J=8.4 Hz, 2H); 4.64 (s, 1H); 4.57 (s, 1H); 3.97 (t, J=12.0 Hz, 1H); 3.64 (dd, J=12.0 Hz, 2H); 2.35 (m, 2H); 2.1 (s, 3H); 1.93 (m, 4H); 1.64 (s, 3H); 1.62 (s, 3H); 1.48 (m, 2H); 0.9 (t, J=8.0 Hz, 2H); 0.09 (s, 9H).

Preparation of Compound 170:

To a solution of compound 24 (3.5 g, 14.0 mmol) in THF (30 ml) was added 2.5 M solution of n-BuLi (6.0 ml, 15 mmol in hexanes) at −78° C. The solution was stirred for 1 h at that temperature. To this a solution of ketone 169 (3.8 g, 11.2 mmol) in THF (20 ml) was added and the reaction mixture was brought to room temperature over a period of 12 h. The reaction was quenched with aq. ammonium chloride (10,0 ml) and extracted with ethyl acetate (25 ml×3). Combined organic extracts were dried over $Na_2SO_4$. and evapoated under vacuum. The crude product was purified by flash chromatography on silica gel using hexane/EtOAc to give product 170 (4.14 g, 85%). $^1$H NMR (400 MHz, $CDCl_3$): δ6.94 (s, 1H); 6.48 (s, 1H); 5.18 (t, J=8.2 Hz, 1H); 4.76 (s, 1H), 4.69 (s, 1H); 4.65 (dd, J=12.0 Hz, 2H); 4.07 (t, J=8.4 Hz, 1H); 3.77 (dd, J=10.0 Hz, 1H); 3.52 (dd, J=8.2 Hz, 1H); 2.7 (s, 3H); 2.36 (m, 1H); 2.34 (m, 1H); 2.03 (m, 4H); 2.0 (s, 3H); 1.69 (s, 3H); 1.68 (s, 3H); 1.5 (m, 2H); 0.93 (t, J=6.0 Hz, 2H); −0.09 (s, 9H). $^{13}$C NMR (100 MHz, $CDCl_3$): δ153.1, 137.8, 122.8, 121.6, 116.1, 110.1, 110.0, 92.4, 82.2, 65.5, 65.0, 38.0, 32.0, 26.3, 23.9, 22.8, 19.7, 18.5, 14.2, 0.1.

Preparation of Compound 171:

To solution of $(IPC)_2BH$ (3.4 g, 11.9 mmol) in THF (25 ml) was added a solution of compound 170 (4.14 g, 9.5 mm0l) in THF (25 ml). Reaction was stirred at room temparature for 0.5 h and water was added followed by the addition of saturated solution of sodiumperborate (5 ml) and LiOH (0.8 g, 30 mmol). reaction was stirred at room temperature for 2 h and extracted with ethyl acetate (25 ml×3) and washed with brine solution. The combined organic extracts were dried over anhydrous $Na_2SO_4$. and evapoated under vacuum. The crude product was purified by flash chromatography on silica gel using hexane/EtOAc to give product 171 (3.5 g, 82%). $^1$H NMR (400 MHz, $CDCl_3$): δ6.94 (s, 1H); 6.48 (s, 1H); 5.18 (t, J=6.0 Hz, H); 406 (dd, J=8.6 Hz, 2H); 4.06 (t, J=6.6 Hz, 1H); 3.75 (dd, J=8.4 Hz, 1H); 3.52 (m, 2H); 3.41 (dd, J=6.0 Hz, 1H); 2.7 (s, 3H); 2.32 (m, 1H); 2.3 (m, 1H); 2.03 (m, 4H); 1.99 (s, 3H); 1.7 (m, 2H); 1.67 (s, 3H); 1.6 (m, 2H); 1.4 (m, 4H); 0.9 (t, J=8 Hz, 2H); 0.89 (d, J=8 Hz, 3H); 0.01 (s, 9H). $^{13}$C NMR (100 MHz, $CDCl_3$): δ153.1, 137.7, 121.2, 116.2, 93.2, 77.1, 77.4, 72.2, 72.15, 67.4, 60.1, 37.1, 33.5, 32.3, 29.0, 19.5, 16.9, 15.2, 0.7, −0.09.

Preparation of Compound 172:

To a −78° C. cooled solution of oxalyl chloride (1.16 g, 9.27 mmol) in dichloromethane (25 ml) was added DMSO (1 ml, 12 mmol) and stirred for 15 min. To this alcohol 171 (3.5 g, 7.7 mmol) in dichloromethane (15 ml) was added and the reaction mixture was stirred at the same temperature for 1 h. To this triethylamine (2.4 g, 24 mmol) was added and the reaction mixture was warmed to 0° C. and quenched with water. Extracted with ether (25 ml×3). The combined organic extracts were dried over anhydrous $Na_2SO_4$. and evapoated under vacuum. The crude product was purified by flash chromatography on silica gel using hexane/ether to give product 172 (3.05 g, 88%). $^1$H NMR (400 MHz, $CDCl_3$): δ 9.2 (d, J=6.0 Hz, 1H); 6.95 (s, 1H); 6.49 (s, 1H); 5.18 (t, J=8.0 Hz, 1H); 4.65 (dd, J=8.2 Hz, 2H); 4.08 (t, J=6.4 Hz, 1H); 3.74 (dd, J=7.4 Hz, 1H); 3.52 (dd, J=6.8 Hz, 1H); 2.7 (s, 3H); 2.32 (m, 1H); 2.3 (m, 1H); 2.01 (m, 4H); 2.0 (s, 3H); 1.72 (m, 2H); 1.68 (s, 3H); 1.6 (m, 2H); 1.54 (m., 1H); 1.2 (d, J=8.2 Hz, 3H); 0.98 (t, J=6.4 Hz, 2H); 0.009 (s, 9H); $^{13}$C NMR (100 MHz, $CDCl_3$): □175.8, 137.8, 121.7, 116.1, 110.0, 93.5, 77.8, 72.2, 67.2, 59.3, 36.1, 32.4, 25.6, 23.8, 19.5, 16.9, 14.2, 0.01, −0.09.

Aldol Reaction:

A solution of ketoacid 10 (367 mg, 1.12 mmol, 1.2 eq) in THF (4 ml) was added dropwise to a freshly prepared solution of LDA [diisopropylamine (0.419 ml, 3 mmol) was added to n-BuLi (1.2 ml, 2.5 M solution in hexanes, 3.0 mmol) in 10 ml of THF at 0 C] at −78° C. After being stirred for 15 min, the solution was warmed to −40° C., and after 0.5 h at that temperature it was recooled to −78° C. A solution of $ZnCl_2$ (2.0 M solution in ether, 3.0 ml, 3 mmol) was added and stirred for 0.5 h, subsequently to this a solution of aldehyde 172 (451 mg, 1.0 mmol) in THF (5 ml) was added. The reaction mixture was stirred at this temperature for 0.5 h and warmed to −50° C. and stirred for an additional 0.5 h. Quenched the reaction with aq. ammonium chloride solution. Allowed to raised the temperature to 0° C. and acetic acid (6.0 eq) was added and extracted with ethyl acetate (25 ml×3). The combined organic extracts were dried over anhydrous $Na_2SO_4$ and evapoated under vacuum to afford a mixture of aldol products 173a and 173b.

Epothilone B, 202:

$[α]^{25}_D$ −31 (c 0.25, $CHCl_3$) IR(film): 3300(br), 2948, 2805, 1746, 1658, 1518, 1460, 1206, 915 $cm^{-1}$ $H^1$ NMR ($CDCl_3$, 400 MHz) δ 6.94(s, 1H); 6.59(s, 1H); 5.42(dd, J=8.0, 3.0 Hz, 1H); 4.22(br, 2H); 3.71(t, J=4.2 Hz, 1H); 3.29, (qd, J=7.0, 4.2 Hz, 1H); 2.8(dd, J=7.5, 5 Hz, 1H); 2.7(s, 3H); 2.65(br, 1H); 2.53(dd, J=14.1, 10.2 Hz, 1H); 2.35(dd, J=13.5, 2.5 Hz, 1H); 2.13(−2.06(m, 1H); 2.08(s, 3H); 1.91 (dd, J=15.6, 8.0 Hz, 1H); 1.77–1.65(m, 3H); 1.54–1.46(m, 2H); 1.45–1.35(m, 3H); 1.36(s, 3H); 1.27(s, 3H); 1.16(d, J=7.0 Hz, 3H); 1.07(s, 3H); 0.99(d, J=7.4 Hz, 3H). $C^{13}$ ($CDCl_3$, 100 MHz) δ 220.7, 170.4, 165.0, 152.0, 139.2, 138.4, 120.9, 119.2, 115.6, 78.9, 74.1, 72.3, 53.5, 41.7, 39.6, 38.4, 32.5, 31.9, 31.7, 31.6, 25.4, 22.9, 19.0, 18.0, 15.9, 15.7, 13.4. FAB HRMS m/z 508.2642, $(MH)^+$ calcd for $C_{27}H_{41}NO_6S$ 508.2655.

Epothilone D, 225:

$[α]^{25}_D$ −69.5 (c 0.27, $CHCl_3$) IR(film): 3300(br), 2948, 2805, 1746, 1658, 1518, 1460, 1206, 915 $cm^{-1}$ $H^1$ NMR ($CDCl_3$, 400 MHz) δ 6.97(s, 1H); 6.61(s, 1H); 5.23(dd, J=10.0, 6.0 Hz, 1H); 5.17(dd, J=10.0, 4.0 Hz, 1H); 4.31(dd, J=11.4, 6.0 Hz, 1H); 3.74(dd, J=6.0, 4.0 Hz, 1H); 3.45(bs, 1H); 3.18(qd, J=6.9, 2.8 Hz, 1H); 3.06(bs, 1H); 2.7(s, 3H); 2.63(dt, J=15, 10, 1H); 2.48(dd, J=14.6, 4.0 Hz, 1H); 2.36–2.29(m, 1H); 2.28(dd, J=14.4, 3.0 Hz, 1H); 2.22(ddd, J=15.6, 3.5, 2.0 Hz, 1H); 2.08(s, 3H); 1.91–1.88(m, 1H); 1.78–1.75(m, 2H); 1.68(s, 3H); 1.36(s, 3H); 1.33–1.24(m, 4H); 1.21(d, J=8.0 Hz, 3H); 1.09(s, 3H); 1.05(d, J=9.0 Hz, 3H). $C^{13}$ ($CDCl_3$, 100 MHz) δ 220.7, 170.4, 165.0, 152.0, 139.2, 138.4, 120.9, 119.2, 115.6, 78.9, 74.1, 72.3, 53.5, 41.7, 39.6, 38.4, 32.5, 31.9, 31.7, 31.6, 25.4, 22.9, 19.0, 18.0, 15.9, 15.7, 13.4. FAB HRMS m/z 491.2601, $(MH)^+$ calcd for $C_{27}H_{41}NO_5S$ 491.2705.

7-TROC-Epothilone D, 224:

$[α]^{25}_D$ −46.5 (c 1.5, $CHCl_3$) IR(film): 3350(br), 2958, 2875, 1766, 1745, 1658, 1518, 1460, 1206, 915 $cm^{-1}$ $H^1$ NMR ($CDCl_3$, 400 MHz) δ 7.05(s, 1H); 6.73(s, 1H); 5.15(d, J=10.0 Hz, 1H); 5.08(d, J=8.0 Hz, 1H); 4.8(dd, J=8.2, 3.0 Hz, 2H); 4.28(d, J=8.0 Hz, 1H); 3.43(t, J=6.0 Hz, 1H); 2.81(s,. 3H); 2.7(d, J=8.0 Hz, 1H); 2.68(d, J=6.0 Hz, 1H); 2.52–2.49(m, 2H); 2.35(dd, J=10.0, 2.0 Hz, 2H); 2.3(m, 1H); 2.2(dd, J=6.0, 4.0 Hz, 1H); 2.07(s, 3H); 1.98(m, 2H); 1.65(s, 3H); 1.51(m, 2H); 1.39(s, 3H); 1.2(d, J=8.0 Hz, 3H); 1.1(s, 3H); 1.03(d, J=8.2 Hz, 3H). $C^{13}$ ($CDCl_3$, 100 MHz) δ 217.2, 171.0, 166.0, 151.3, 142.6, 141.9, 141.1, 121. 2, 120.0, 119.0, 89.1, 87.6, 83.1, 72.5, 54.3, 41.0, 37.1, 34.5, 31.5, 30.8, 28.6, 25.3, 23.1, 20.7, 16.2, 15.0, 14.6, 14.1, 10.6, 8.4. FAB HRMS m/z 667.2642, $(MH)^+$ calcd for $C_{29}H_{41}Cl_3NO_6S$ 667.2655.

7-TROC-3-TBS-Epothilone D, 222:

$[α]_D$ −49.8 (c 1.2, $CHCl_3$) IR(film): 2948, 2805, 1759, 1746, 1658, 1518, 1460, 1206, 915 $cm^{-1}$ $H^1$ NMR ($CDCl_3$, 400 MHz) δ 6.99(s, 1H); 6.57(s, 1H); 5.21(dd, J=10.0 Hz, 1H); 4.99(d, J=11.2 Hz, 1H); 4.8(dd, J=15.0, 10.2 Hz, 1H); 4.06(d, J=10.2 Hz, 1H); 3.34(qd, J=10.0, 3.5 Hz, 1H);

2.86(d, J=15.0 Hz, 1H); 2.71(s, 3H); 2.69(d, J=12,0 Hz, 1H); 2.54(t, J=8.0 Hz, 1H); 2.13(s, 1H); 2.08–2.04(m, 2H); 1.8–1.76(m, 4H); 1.67(s, 3H); 1.61(m, 4H); 1.24(s, 3H); 1.21(s, 3H); 1.15(d, J=11.0 Hz, 3H); 1.04(d, J=10.0 Hz, 3H); 0.8(s, 9H); 0.15(s, 3H); −0.08(s, 3H). $C^{13}$ (CDCl$_3$, 100 MHz) δ 217.0, 172.0, 166.7, 151.5, 142.0, 141.9, 141.8, 121.0, 120.2, 119.0, 89.1, 87.6, 83.1, 72.5, 54.3, 41.0, 37.1, 34.5, 31.5, 30.8, 28.6, 25.3, 23.1, 20.7, 16.2, 15.0, 14.6, 14.1, 10.8, 8.6, −6.2, −6.0. FAB HRMS m/z 780.2601, (MH)$^+$ calcd for $C_{36}H_{56}Cl_3NO_7SSi$ 780.2612.

2S,6,10-Trimethyl-11-(2-methylthiazol-4-yl)-9S-(2-trimethylsilanyl-ethoxymethoxy)-undeca-6Z,10E-dien-1-al, 203:

$[\alpha]^{25}_D$ 12.1 (c 2.0, CHCl$_3$) IR(film): 2908, 2858, 1716, 1658,1518, 1465, 1256, 915 cm$^{-1}$ H$^1$ NMR (CDCl$_3$, 400 MHz) δ 9.5(d, J=4.2 Hz, 1H), 6.93(s, 1H); 6.47(s, 1H); 5.18(t, J=10.0 Hz, 1H); 4.63(dd, J=12.0, 8.0 Hz, 2H); 4.06(t, J=8.2 Hz, 1H); 3.75(q, J=12.0, 8.4 Hz, 2H); 3.51(dd, J=10.0, 8.0 Hz, 2H); 2.71(s, 3H); 2.31(m, 4H); 2.03(q, J=10.0, 6.2 Hz, 2H); 1.99(s, 3H); 1.68(m, 2H); 1.66(s, 3H); 1.4(m, 4H); 1.35(m, 2H), 1.08(d, J=12.0 Hz, 3H), 0.94(t, J=8.4 Hz, 2H); 0.002(s, 9H). $C^{13}$ (CDCl$_3$, 100 MHz) δ 210.0, 161.07, 152.10, 139.19, 121.79, 121.65, 116.17, 92.52, 82.17, 65.61, 46.64, 33.08, 32.27, 30.72, 25.54, 23.83, 19.59, 18.50, 14.25, 13.30, −4.01. FAB HRMS m/z 452.7368, (MH)$^+$ calcd for $C_{24}H_{41}NO_3SSi$ 452.7388.

2S,6,10-Trimethyl-11-(2-methylthiazol-4-yl)-9S-(2-trimethylsilanyl-ethoxymethoxy)-undeca-6Z,10E-dien-1-ol, 216:

$[\alpha]^{25}_D$ 17.8 (c 1.2, CHCl$_3$) IR(film): 3400(br), 2948, 2805, 1746, 1658, 1518, 1460, 1206, 915 cm$^{-1}$ H$^1$ NMR (CDCl$_3$, 400 MHz) δ6.94(s, 1H); 6.48(s, 1H); 5.18(t, J=8.0 Hz, 1H); 4.65(dd, J=14.2, 8.0 Hz,. 2H); 4.07(t, J=8.0 Hz, 1H); 3.74(dd, J=14, 8.2 Hz, 1H); 3.43(dq, J=12.0, 8.2 Hz, 2H); 3.41(dd, J=10.0, 8.4 Hz, 2H); 2.7(s, 3H); 2.31(m, 2H); 2.03(m, 2H); 1.99(s, 3H); 1.72(m, 2H); 1.67(s, 3H); 1.44(m, 2H); 1.37(m, 4H); 1.1(m, 2h); 0.95(t, J=10.4 Hz, 2H); 0.89(d, J=1 1 Hz, 3H); −0.09(s, 9H). $C^{13}$ (CDCl$_3$, 100 MHz) δ 137.64, 121.63, 121.35, 115.20, 92.45, 85.74, 68.55, 65.53, 50.54,34.7, 33.43, 32.54, 25.70, 24.12, 23.88, 19.52, 18.50, 16.95, 14.24, −4.01. FAB HRMS m/z 454.2576, (MH)$^+$ calcd for $C_{24}H_{41}NO_3SSi$ 454.2675.

2-Methyl-4-[2,6,10-trimethyl-3-(2-trimethylsilanylothoxymethoxy)-undeca-1,5,10-trienyl]-thiazole, 215:

$[\alpha]^{25}_D$ 18.4 (c 1.25, CHCl$_3$) IR(film): 2948, 2805, 1658, 1518, 1480, 1460, 1206, 1165, 915 cm$^{-1}$ H$^1$ NMR (CDCl$_3$, 400 MHz) δ 6.93(s, 1H); 6.48(s, 1H); 5.19(dd, J=8.2, 6.0 Hz, 1H); 4.76(s, 1H); 4.65(dd, J=12.2, 8.0 Hz, 2H); 4.09(t, J=10.0 Hz, 1H); 3.72(q, J=11.2, 6.0 Hz, 2H); 3.52(dd, J=14.0, 10.4 Hz, 1H); 3.50(dd, J=12.0, 6.0 Hz, 1H); 3.50(dd, J=12.2, 8.2 Hz, 1H); 2.7(s, 3H); 2.36(dq, J=10.1, 8.2 Hz, 1H); 2.31(dq, J=10.0, 6.0 Hz, 1H); 2.04(m, 6H); 1.68(s, 3H); 1.66(s, 3H); 1.51(m, 4H); 0.9(t, J=10.5, 2H); −0.09(s, 9H). $C^{13}$ (CDCl$_3$, 100 MHz) δ 154.10, 146.41, 139.27, 137.55, 121.64, 121.36, 116.11, 110.17, 92.42, 82.27, 65.58, 38.09, 33.02, 32.05, 26.29, 23.89, 22.82, 19.60, 18.50, 14.22, −5.12. FAB HRMS m/z 436.2627, (MH)$^+$ calcd for $C_{24}H_{41}NO_2SSi$ 436.2637.

(2-{1-[1-(4-Methoxy-benzyloxy)-ethyl]-4,8-dimethyl-nona-3,8-dienyloxymethoxy}-ethyl)-trimethyl-silane, 212:

$[\alpha]^{25}_D$ 24.2 (c 2.5, CHCl$_3$) IR(film): 2948, 2805, 1658, 1518, 1460, 1206, 1150, 915 cm$^{-1}$ H$^1$ NMR (CDCl$_3$, 400 MHz) δ 7.24(d, J=12.0 Hz, 2H); 6.85(d, J=11.4 Hz, 2H); 5.13(dd, J=8.2 Hz, 1H); 4.77(s, 1H); 4.73(s, 1H); 4.69(dd, J=12.0, 6.0 Hz, 2H); 4.48(dd, J=6.4, 4.0 Hz, 2H); 3.81(s, 3H); 3.79–3.61(m, 3H); 2.2(m, 2H); 2.01(m, 4H); 1.7(s, 3H); 1.69(s, 3H); 1.54(m, 2H); 1,18(d, J=10.4 Hz, 3H); 0.93(t, J=8 Hz, 2H); 0.01(s, 9H). $C^{13}$ (CDCl$_3$, 100 MHz) δ 6156.21, 146.23, 137.44, 131.35, 129.52, 121.60, 119.69, 110.22, 110.0, 94.72, 79.46, 76.36, 70.89, 65.59, 55.64, 38.10, 32.03, 29.95, 26.25, 23.92, 18.50, 15.53, −4.12. FAB HRMS m/z 449.2642, (MH)$^+$ calcd for $C_{27}H_{47}O_4Si$ 449.2655.

2-(4-Methoxy-benzyloxy)-6,10-dimethyl-undeca-5,10-dien-3-ol, 211:

$[\alpha]^{25}_D$ 21.8 (c 5.0, CHCl$_3$) IR(film): 3415, 2968, 2845, 1658, 1518, 1460, 1206, 915 cm$^{-1}$ H$^1$ NMR (CDCl$_3$, 400 MHz) δ 7.26(d, J=7.5 Hz, 2H); 6.78(d, J=8.1 Hz, 2H); 5.17(dd, J=8.0, 4.0 Hz, 1H); 4.7(s, 3H); 4,67(s, 3H); 4.45 (dd, J=12.2, 6.0 Hz, 2H); 3.8(s, 3H), 3.71(m, 1H); 3.5(m, 1H); 2.18(m, 2H); 2.01(m, 4H); 1.71(s, 3H); 1.66(s, 3H); 1.26, m, 2H); 1.17(d, J=6.9 Hz, 3H). $C^{13}$ (CDCl$_3$, 100 MHz) δ 100.81, 95.40, 88.45, 81.13, 79.90, 71.93, 65.48, 61.76, 31.20, 30.96, 30.66, 27.53, 24.79, 10.57. FAB HRMS m/z 333.2251, (MH)$^+$ calcd for $C_{21}H_{32}O_3$ 333.2362.

2-[1-(4-Methoxy-benzyloxy)-ethyl]-oxirane, 205:

$[\alpha]^{25}_D$ 21.8 (c 5.0, CHCl$_3$) IR(film): 2968, 1658, 1518, 1460, 1206, 1150, 915 cm$^{-1}$ H$^1$ NMR (CDCl$_3$, 400 MHz) δ: 7.25(d, J=8.4 Hz, 2H); 6.85(d, J=8.2 Hz, 2H); 4.54(d, J=12.0 Hz, 1H); 4.49(d, J=12.2 Hz, 1H); 3.7(s, 3H); 3.39(dq, J=8.4, 6.0 Hz, 1H); 2.91(m, 1H); 2.77(dd, J=6.0, 4.0 Hz. 1H); 2.68(dd, J=6.6, 4.0 Hz, 1H); 1.28(d, J=8.0 Hz, 3H). $C^{13}$ (CDCl$_3$, 100 MHz)δ 159.18, 132.1, 130.52, 129.06, 77.42, 73.91, 70.94, 55.14, 54.26, 45.64, 17.48. FAB HRMS m/z 209.1101, (MH)$^+$ calcd for $C_{12}H_{16}O_3$ 209.1121.

Bromo-4-methyl-pent-4-ene, 209:

IR(film): 2968, 1658, 1518, 1460, 1150, 915 cm$^{-1}$ H$^1$ NMR (CDCl$_3$, 400 MHz) δ: 4.76(s, 1H); 4.72(s, 1H); 3.4(t, J=8.0 Hz, 2H); 2.15(t, J=6.2 Hz, 2H); 2.14(dd, J=8.0, 4.0 Hz, 2H); 1.72(s, 3H). $C^{13}$ (CDCl$_3$, 100 MHz) δ 144.31, 111.39, 36.49, 33.65, 30.99, 22.68. FAB HRMS m/z 163.0004, (MH)$^+$ calcd for $C_6H_{11}Br$ 162.0104.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

What is claimed is:

1. A method for use in producing epothilones and analogs and derivatives thereof, comprising:

(a) performing an aldol condensation of a first compound of the formula:

and stereoisomers thereof, with a second compound selected from the formulas:

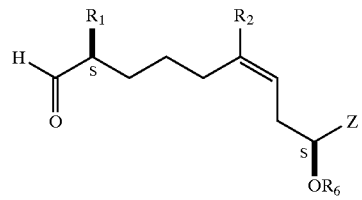

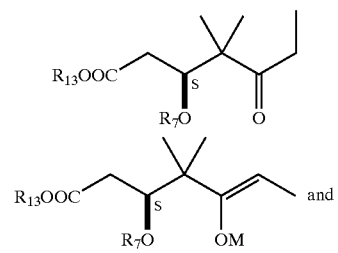

-continued

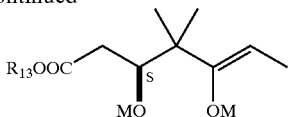

and stereoisomers thereof, thereby to form a third compound of the formula:

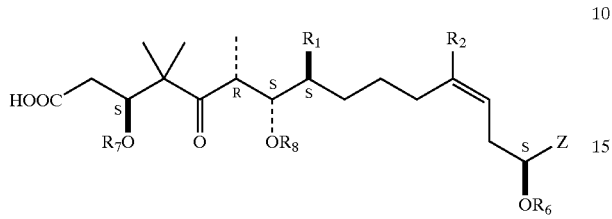

and stereoisomers thereof wherein Z is

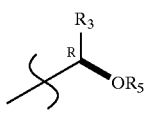

wherein $R_1$, $R_2$, and $R_3$ are each selected from H, alkyl, alkenyl, alkynyl, aryl, cycloalkyl, heterocyclo, and substitutions thereof; wherein $R_5$, $R_6$, $R_7$ and $R_8$ are each selected from H and a protecting group; wherein $R_{13}$ is H or a metal salt; and wherein M is an alkali metal salt or transition metal salt; and (b) performing a macrolactonization of the third compound thereby to form a fourth compound of the formula:

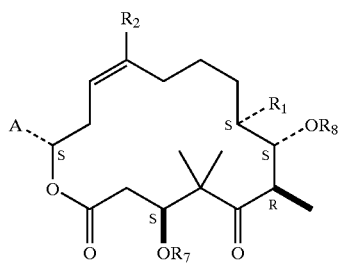

and stereoisomers thereof, wherein A is

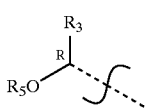

wherein $R_1$, $R_2$, and $R_3$ are each selected from H, alkyl, alkenyl, alkynyl, aryl, cycloalkyl, heterocyclo, and substitutions thereof; and wherein $R_5$, $R_7$ and $R_8$ are each selected from H and a protecting group.

2. A method according to claim 1 wherein $R_1$, and $R_3$ are each methyl, and $R_2$ is H or methyl.

3. A method according to claim 2 wherein $R_2$ is methyl.

4. A method according to claim 2 wherein at least one of $R_5$–$R_8$ is TBS.

5. A method according to claim 2 wherein $R_6$, $R_7$ and $R_8$ are each TBS.

6. A method according to claim 2 wherein $R_5$ is PMB.

7. A method according to claim 1 wherein $R_5$ is selected from PMB, DPS and TBS; wherein $R_6$ is selected from H, TBS, TMS, TIPS, PMBM and SEM; wherein $R_7$ is selected from H, TBS, TROC, —CO(CH$_2$)$_4$CH$_3$ and —CO(CH$_2$)$_3$CH=CH$_2$; and wherein $R_8$ is selected from H and TBS.

8. A chemical compound formed according to the method of claim 1.

9. A chemical compound of the formula:

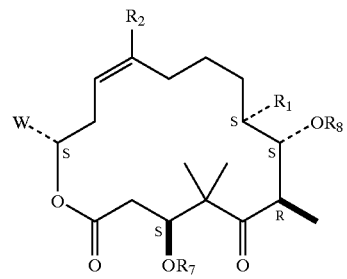

and stereoisomers thereof, wherein W is selected from

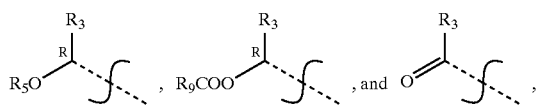

wherein $R_1$, $R_2$, and $R_3$ are each selected from H, alkyl, alkenyl, alkynyl, aryl, cycloalkyl, heterocyclo, and substitutions thereof; wherein $R_5$, is selected from H and a protecting group; wherein $R_7$ is selected from H, a protecting group and COR$_{11}$; wherein $R_8$ is selected from H, a protecting groug and COR$_{12}$; wherein $R_9$ is selected from alkyl, alkenyl, alkynyl, aryl, cycloalkyl, heterocyclo, and substitutions thereof; and wherein $R_{11}$ and $R_{12}$ are each selected from alkyl, alkenyl, alkynyl, aryl, alkyl-aryl, alkyloxy, aryloxy, cycloalkyl, heterocyclo, amino, sulfo, and substitutions thereof.

10. A chemical compound according to claim 9 wherein at least one of $R_{11}$ and $R_{12}$ is selected from —(CH$_2$)$_x$CH$_3$ and —(CH$_2$)$_y$CH=CH$_2$, where x and y are integers.

11. A chemical compound according to claim 10 wherein x and y are selected from the integers 3 and 4.

12. A chemical compound according to claim 10 wherein x is 4 and y is 3.

13. A method for use in producing epothilones and analogs and derivatives thereof, comprising:

(a) performing an aldol condensation of a first compound of the formula:

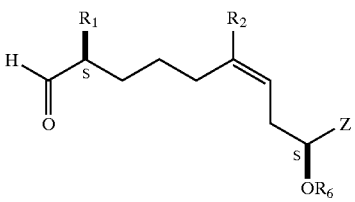

and stereoisomers thereof, with a second compound selected from the formulas:

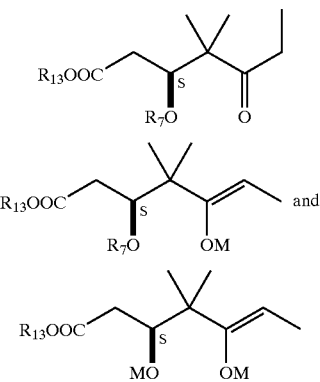

and stereoisomers thereof, thereby to form a third compound of the formula:

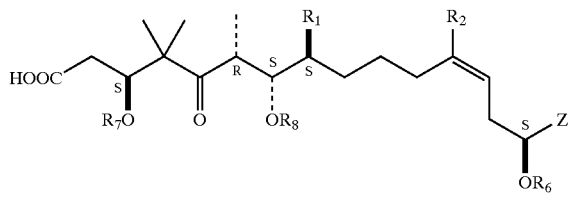

and stereoisomers thereof, wherein Z is selected from

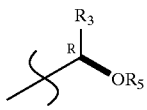

and

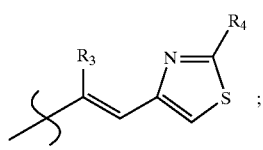

wherein $R_1$, $R_3$ and $R_4$ are each, methyl; wherein $R_2$ is H; wherein $R_5$, $R_6$, $R_7$ and $R_8$ are each selected from H and a protecting group; wherein $R_{13}$ is H or a metal salt; and wherein M is an alkali metal salt or transition metal salt; and (b) performing a macrolactonization of the third compound thereby to form a fourth compound of the formula:

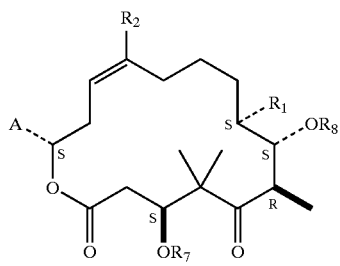

and stereoisomers thereof, wherein A is selected from

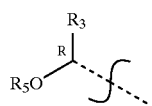

and

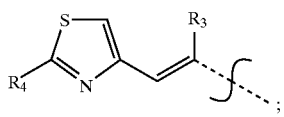

wherein $R_1$, $R_3$ and $R_4$ are each methyl; wherein $R_2$ is H; and wherein $R_5$, $R_7$ and $R_8$ are each selected from H and a protecting group.

14. A method for use in producing epothilones and analogs and derivatives thereof, comprising:

(a) performing an aldol condensation of a first compound of the formula:

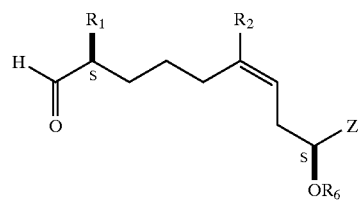

and stereoisomers thereof, with a second compound selected from the formulas:

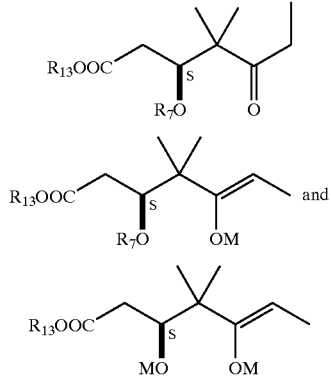

and stereoisomers thereof, thereby to form a third compound of the formula:

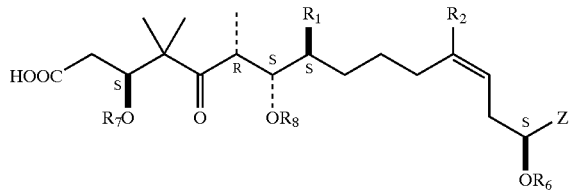

and stereoisomers thereof, wherein Z is selected from

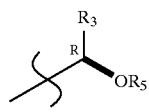

and

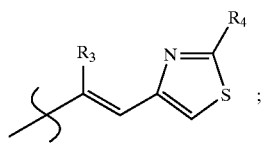

wherein $R_1$, $R_3$ and $R_4$ are each methyl; wherein $R_2$ is H or methyl; wherein $R_5$, $R_7$ $R_8$ are each selected from H and a protecting group; wherein $R_6$ is SEM; wherein $R_{13}$ is H or a metal salt; and wherein M is an alkali metal salt or transition metal salt; and (b) performing a macrolactonization of the third compound thereby to form a fourth compound of the formula:

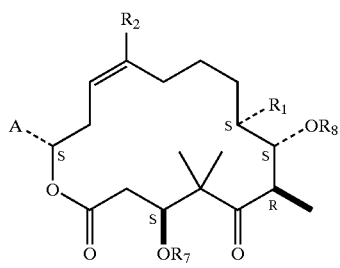

and stereoisomers thereof, wherein A is selected from

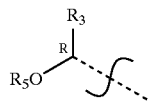

and

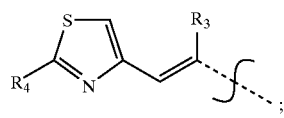

wherein $R_1$, $R_3$ and $R_4$ are each methyl; wherein $R_2$ is H or methyl; and $R_5$, $R_7$ and $R_8$ are each selected from H and a protecting group.

15. A method for use in producing epothilones and analogs and derivatives thereof, comprising:
(a) performing an aldol condensation of a first compound of the formula:

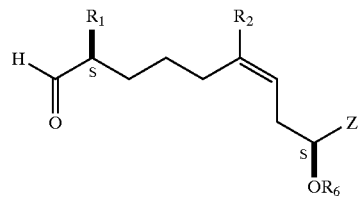

and stereoisomers thereof, with a second compound selected from the formulas:

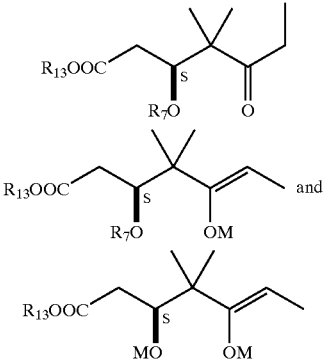

and stereoisomers thereof, thereby to form a third compound of the formula:

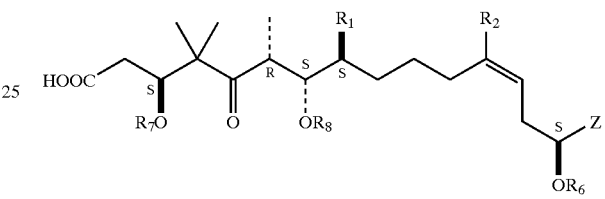

and stereoisomers thereof, wherein Z is selected from

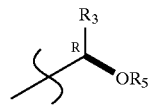

and

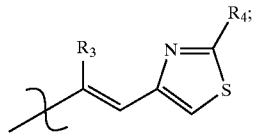

wherein $R_1$, $R_2$, $R_3$ and $R_4$ are each selected from H, alkyl, alkenyl, alkynyl, aryl, cycloalkyl, heterocyclo, and substitutions thereof; wherein $R_5$, $R_6$, $R_7$ and $R_8$ are each selected from H and a protecting group; wherein $R_{13}$ is H or a metal salt; and wherein M is an alkali metal salt or transition metal salt;

(b) performing a macrolactonization of the third compound thereby to form a fourth compound of the formula:

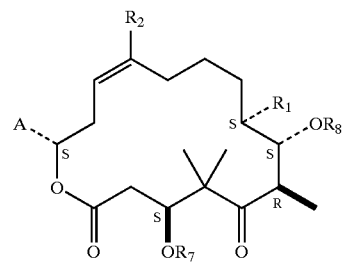

and stereoisomers thereof, wherein A is

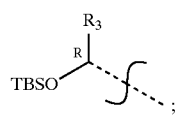

$R_2$ is H or methyl; $R_3$ is methyl; $R_7$ and $R_8$ are each selected from TBS, H, and a protecting group; and (c) converting said fourth compound to a fifth compound of the formula:

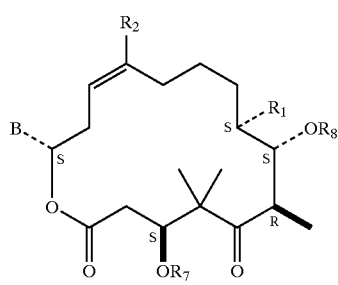

and stereoisomers thereof, wherein B is

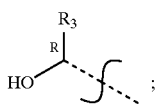

$R_2$ is H or methyl; $R_3$ is methyl; and $R_7$ and $R_8$ are each selected from TBS, H, and a protecting group.

16. A method according to claim 15 wherein said fifth compound is converted to a sixth compound formula:

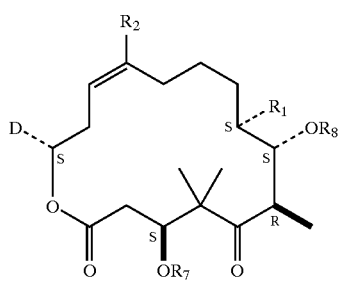

and stereoisomers thereof, wherein D is

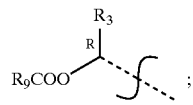

$R_2$ is H or methyl; $R_3$ is methyl; $R_7$ and $R_8$ are each selected from TBS, H, and a protecting group, and wherein $R_9$ is selected from alkyl, alkenyl, alkynyl, aryl, cycloalkyl, heterocyclo, and substitutions thereof.

17. A method according to claim 15 wherein said fifth compound is converted to a sixth compound of the formula:

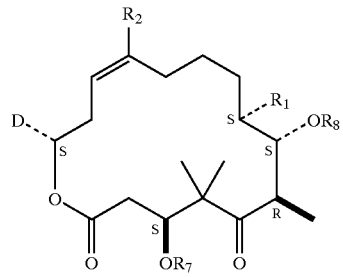

and stereoisomers thereof, wherein D is

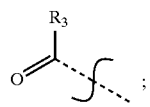

$R_2$ is H or methyl; $R_3$ is methyl; and $R_7$ and $R_8$ are each selected from TBS, H, and a protecting group.

18. A method according to claim 17 wherein said sixth compound is converted to a seventh compound of the formula:

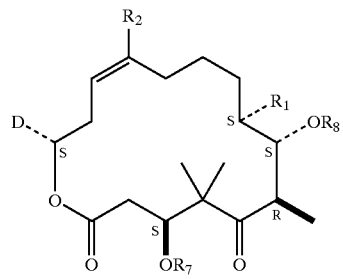

and stereoisomers thereof, wherein D is

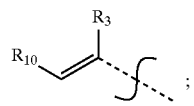

$R_2$ is H or methyl; $R_3$ is methyl; $R_7$ and $R_8$ are each selected from TBS, H, and a protecting group; and wherein $R_{10}$ is selected from alkyl, alkenyl, alkynyl, aryl, cycloalkyl, heterocyclo, and substitutions thereof.

19. A method according to claim 17 wherein said sixth compound is converted to a seventh compound of the formula:

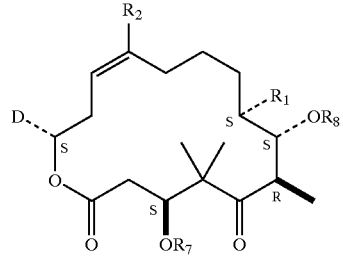

and stereoisomers thereof, wherein D is

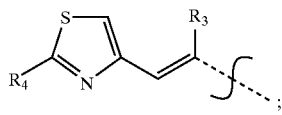

$R_2$ is H or methyl; $R_3$ and $R_4$ are each methyl; and $R_7$ and $R_8$ are each selected from TBS, H, and a protecting group.

20. A method for use in producing epothilones and analogs and derivatives thereof, comprising:

(a) performing an aldol condensation of a first compound of the formula:

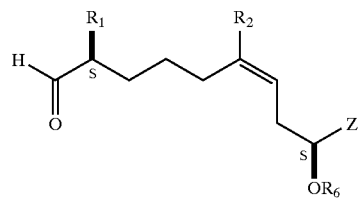

and stereoisomers thereof, with a second compound selected from the formulas:

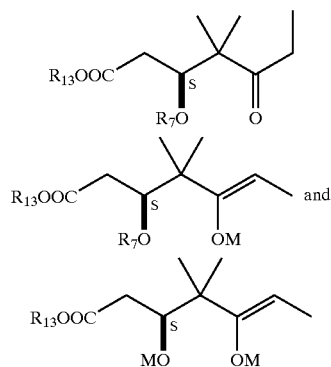

and stereoisomers thereof, thereby to form a third compound of the formula:

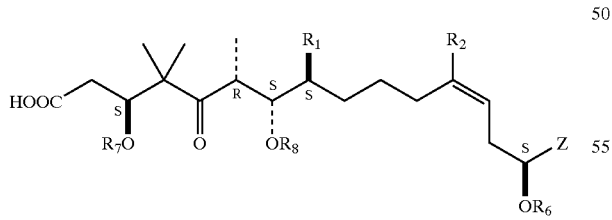

and stereoisomers thereof, wherein Z is selected from

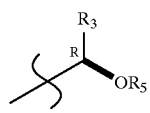

and

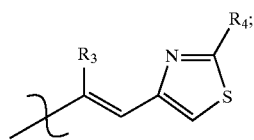

wherein $R_1$, $R_2$, $R_3$ and $R_4$ are each selected from H, alkyl, alkenyl, alkynyl, aryl, cycloalkyl, heterocyclo, and substitutions thereof; wherein $R_5$, $R_6$, $R_7$ and $R_8$ are each selected from H and a protecting group; wherein $R_{13}$ is H or a metal salt; and wherein M is an alkali metal salt or transition metal salt; and (b) performing a macrolactonization of the third compound thereby to form a fourth compound of the formula:

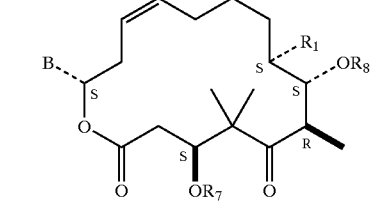

and stereoisomers thereof, wherein A is

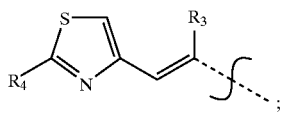

$R_2$ is H or methyl; $R_3$ and $R_4$ are each methyl; and wherein $R_7$ and $R_8$ are each H; and (c) converting said fourth compound to a fifth compound of the formula:

and stereoisomers thereof wherein B is wherein $R_2$, $R_3$, and $R_4$ are each methyl; $R_7$ is

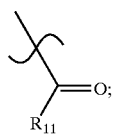

$R_8$ is H; and $R_{11}$ is selected from alkyl, alkenyl, alkynyl, aryl, alkyl-aryl, alkyloxy, aryloxy, cycloalkyl, heterocyclo, amino, sulfo, and substitutions thereof.

21. A method according to claim 20 wherein said fifth compound is further converted to a sixth compound of the formula:

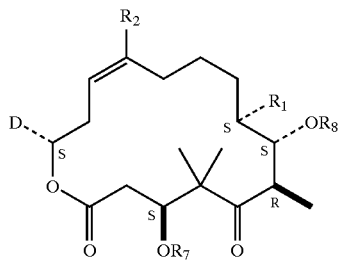

and stereoisomers thereof, wherein D is

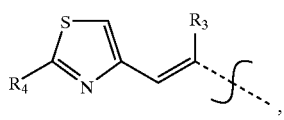

wherein $R_2$, $R_3$, and $R_4$ are each methyl;

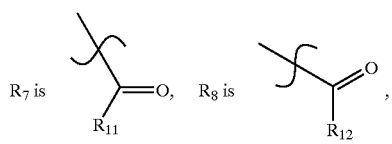

and $R_{11}$ and $R_{12}$ are each selected from alkyl, alkenyl, alkynyl, aryl, alkyl-aryl, alkyloxy, aryloxy, cycloalkyl, heterocyclo, amino, sulfo, and substitutions thereof.

22. A method for use in producing epothilones and analogs and derivatives thereof, comprising:

(a) performing an aldol condensation of a first compound of the formula:

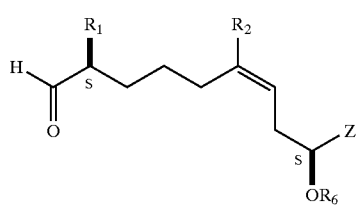

and stereoisomers thereof, with a second compound selected from the formulas:

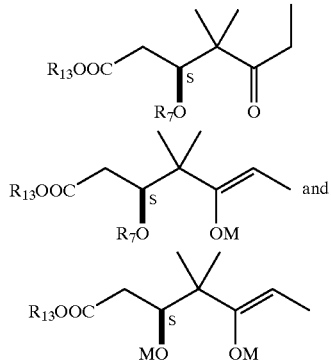

and stereoisomers thereof, thereby to form a third compound of the formula:

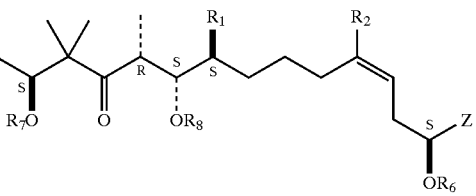

and stereoisomers thereof, wherein Z is selected from

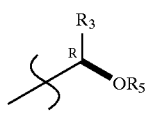

and

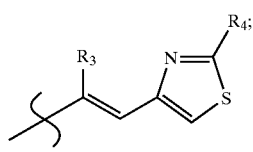

wherein $R_1$, $R_2$, $R_3$ and $R_4$ are each selected from H, alkyl, alkenyl, alkynyl, aryl, cycloalkyl, heterocyclo, and substitutions thereof; wherein $R_5$, $R_6$, $R_7$ and $R_8$ are each selected from H and a protecting group; wherein $R_{13}$ is H or a metal salt, and wherein M is an alkali metal salt or transition metal salt;

(b) performing a macrolactonizaUon of the third compound thereby to form a fourth compound of the formula:

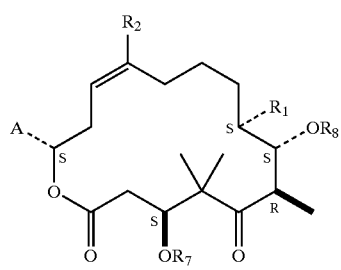

and stereoisomers thereof, wherein A is

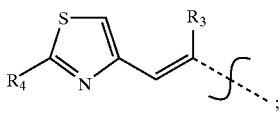

$R_2$ is H or methyl; $R_3$ and $R_4$ are each methyl; and wherein $R_7$ and $R_8$ are each H; and (c) converting said fourth compound to a fifth compound of the formula:

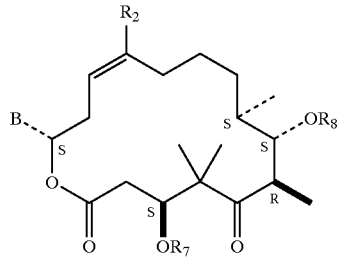

and stereoisomers thereof wherein B is

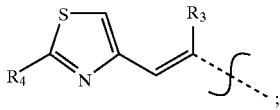

wherein $R_2$, $R_3$, and $R_4$ are each methyl; $R_7$ is TMS; and $R_8$ is H.

23. A method according to claim 22 wherein said fifth compound is further converted to a sixth compound of the formula:

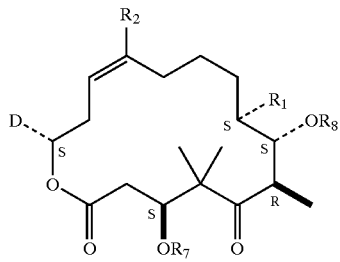

and stereoisomers thereof, wherein D is

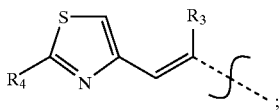

wherein $R_2$, $R_3$, and $R_4$ are each methyl; $R_7$ is H; $R_8$ is

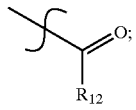

and $R_{12}$ is selected from alkyl, alkenyl, alkynyl, aryl, alkyl-aryl, alkyloxy, aryloxy, cycloalkyl, heterocyclo, amino, sulfo, and substitutions thereof.

24. A method for use in producing epothilones and analogs and derivatives thereof, comprising:

(a) performing an andol condensation of a first compound of the formula:

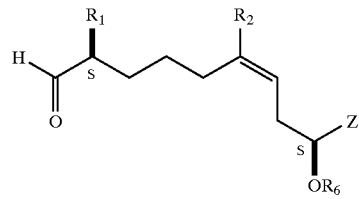

and stereoisomers thereof, with a second compound selected from the formulas:

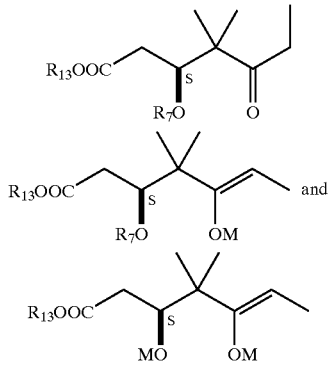

and stereoisomers thereof, thereby to form a third compound of the formula:

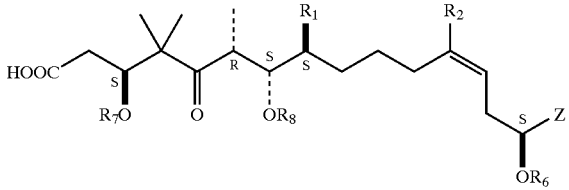

and stereolsomers thereof, wherein Z is selected from

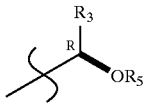

and

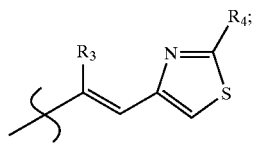

wherein $R_1$, $R_2$, $R_3$ and $R_4$ are each selected from H, alkyl, alkenyl, alkynyl, aryl, cycloalkyl, heterocyclo, and substitutions thereof; wherein $R_5$, $R_6$, $R_7$ and $R_8$ are each selected from H and a protecting group; wherein $R_{13}$ is H or a metal salt; and wherein M is an alkali metal salt or transition metal salt; and (b) performing a macrolactonization of the third compound thereby to form a fourth compound of the formula:

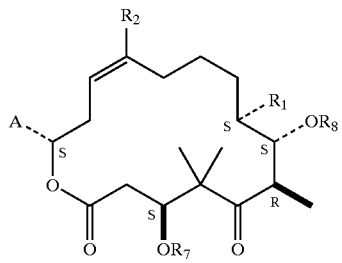

and stereoisomers thereof, wherein A is

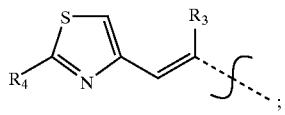

$R_2$ is H or methyl; $R_3$ and $R_4$ are each methyl; and wherein $R_7$ is TBS and $R_8$ is TROC.

25. A method according to claim 24 wherein said fourth compound is further converted to a fifth compound of the formula:

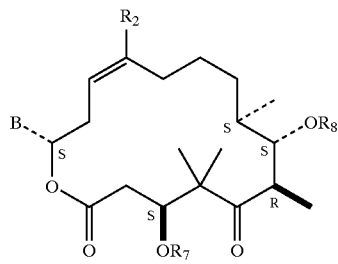

and stereoisomers thereof wherein B is

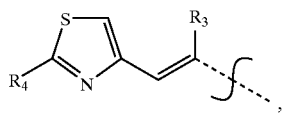

$R_7$ is TBS and $R_8$ is H.

26. A method according to claim 25 wherein said fifth compound is further converted to a sixth compound of the formula:

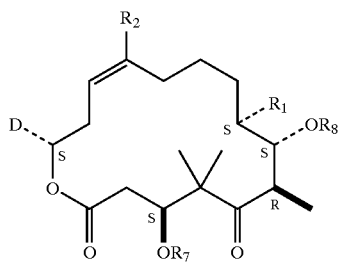

and stereoisomers thereof, wherein D is

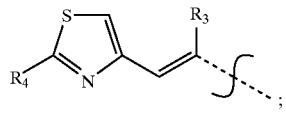

$R_7$ is TBS; $R_8$ is $COR_{12}$; and $R_{12}$ is selected from alkyl, alkenyl, alkynyl, aryl alkyl-aryl, alkyloxy, aryloxy, cycloalkyl, heterocyclo, amino, sulfo, and substitutions thereof.

27. A method according to claim 26 wherein said sixth compound is further converted to a seventh compound of the formula:

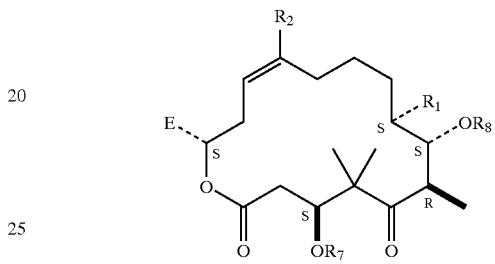

and stereoisomers thereof, wherein E is

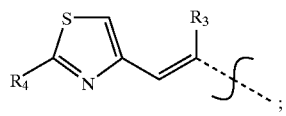

$R_7$ is H; $R_8$ is $COR_{12}$; and $R_{12}$ is selected from alkyl, alkenyl, alkynyl, aryl, alkyl-aryl, alkyloxy, aryloxy, cycloalkyl, heterocyclo, amino, sulfo, and substitutions thereof.

28. A method according to claim 27 wherein said seventh compound is further converted to an eighth compound of the formula:

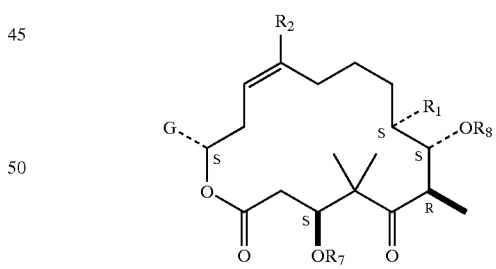

and stereoisomers thereof, wherein G is

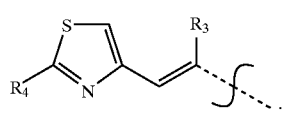

$R_7$ is $COR_{11}$; $R_8$ is $COR_{12}$; and $R_{11}$ and $R_{12}$ are each selected from alkyl, alkenyl, alkynyl, aryl, alkyl-aryl, alkyloxy, aryloxy, cycloalkyl, heterocyclo, amino, sulfo, and substitutions thereof.

29. A method according to claim 24 wherein said fourth compound is further converted to a fifth compound of the formula:

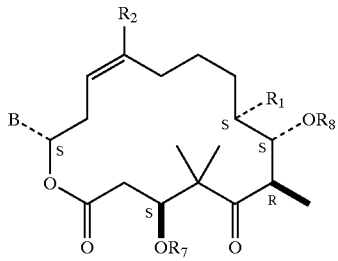

and stereoisomers thereof wherein B is

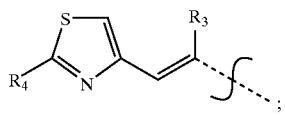

$R_7$ is H; and $R_8$ is TROC.

30. A method according to claim 29 wherein said fifth compound is further converted to a sixth compound of the formula:

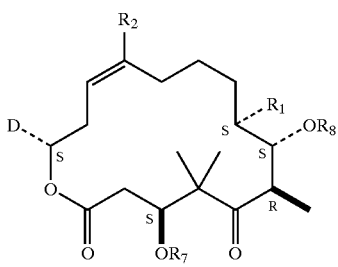

and stereoisomers thereof wherein D is

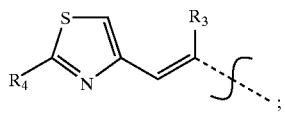

and $R_7$ and $R_8$ are each H.

31. A method according to claim 30 wherein said sixth compound is further converted to Epothilone B.

32. A method according to claim 29 wherein said fifth compound is further converted to a sixth compound of the formula:

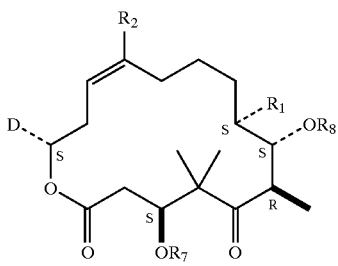

and stereoisomers thereof, wherein D is

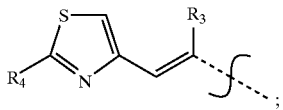

$R_7$ is $COR_{11}$; $R_8$ is TROC; and $R_{11}$ is selected from alkyl, alkenyl, alkynyl, aryl alkyl-aryl, alkyloxy, aryloxy, cycloalkyl, heterocyclo, amino, sulfo, and substitutions thereof.

33. A method according to claim 32 wherein said sixth compound is further converted to a seventh compound of the formula:

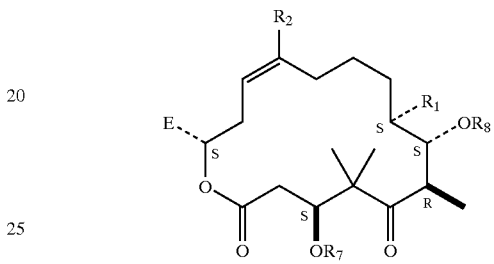

and stereoisomers thereof, wherein E is

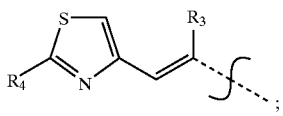

$R_7$ is $COR_{11}$; $R_8$ is H; and $R_{11}$ is selected from alkyl, alkenyl, alkynyl, aryl, alkyl-aryl, alkyloxy, aryloxy, cycloalkyl, heterocyclo, amino, sulfo, and substitutions thereof.

34. A method according to claim 33 wherein said seventh compound is further converted to an eighth compound of the formula:

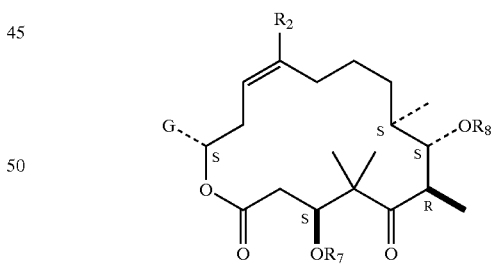

and stereoisomers thereof, wherein G is

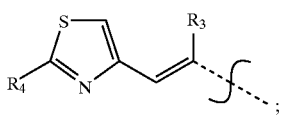

$R_7$ is $COR_{11}$; $R_8$ is $COR_{12}$; and $R_{11}$ and $R_{12}$ are each selected from alkyl, alkenyl, alkynyl, aryl, alkyl-aryl, alkyloxy, aryloxy, cycloalkyl, heterocyclo, amino, sulfo, and substitutions thereof.

35. A method for use in producing epothilones and analogs and derivatives thereof, comprising:

(a) performing an aldol condensation of a first compound of the formula:

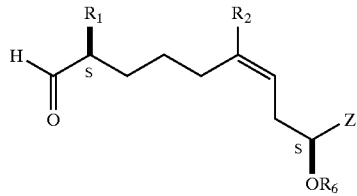

and stereoisomers thereof, with a second compound selected from the formulas:

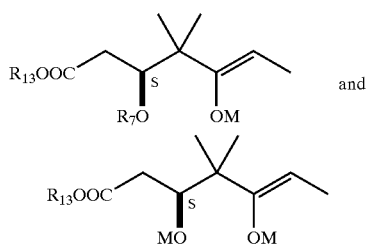

and stereoisomers thereof, thereby to form a third compound of the formula:

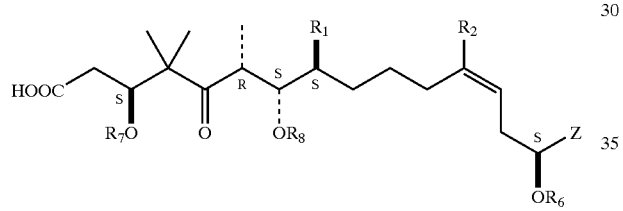

and stereoisomers thereof, wherein Z is

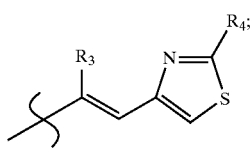

wherein $R_1$, $R_2$, $R_3$ and $R_4$ are each selected from H, alkyl, alkenyl, alkynyl, aryl, cycloalkyl, heterocyclo, and substitutions thereof; wherein $R_6$, $R_7$ and $R_8$ are each selected from H and a protecting group; wherein $R_{13}$ is H or a metal salt; and wherein M is an alkali metal salt or transition metal salt; and (b) performing a macrolactonization of the third compound thereby to form a fourth compound of the formula:

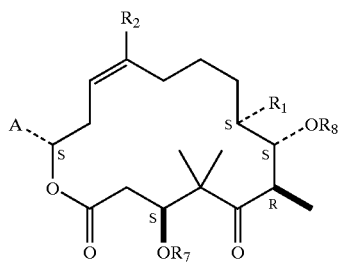

and stereoisomers thereof, wherein A is

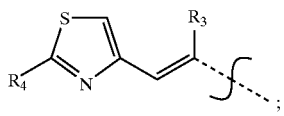

wherein $R_1$, $R_2$, $R_3$ and $R_4$ are each selected from H, alkyl, alkenyl, alkynyl, aryl, cycloalkyl, heterocyclo, and substitutions thereof; and wherein $R_7$ and $R_8$ are each selected from H and a protecting group.

36. A method according to claim 35 wherein $R_1$, $R_3$ and $R_4$ are each methyl, and $R_2$ is H or methyl.

37. A method according to claim 36 wherein $R_2$ is methyl.

38. A method according to claim 36 wherein at least one of $R_6$—$R_8$ is TBS.

39. A method according to claim 36 wherein $R_6$, $R_7$ and $R_8$ are each TBS.

40. A method according to claim 35 wherein $R_6$ is selected from H, TBS, TMS, TIPS, PMBM and SEM; wherein $R_7$ is selected from H, TBS, TROC, —CO(CH$_2$)$_4$CH$_3$ and —CO(CH$_2$)$_3$CH=CH$_2$; and wherein $R_8$ is selected from H and TBS.

41. A method according to claim 35 wherein said fourth compound is of the formula:

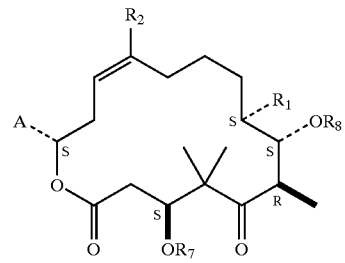

and stereoisomers thereof, wherein A is

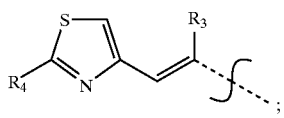

$R_2$ is H or methyl; $R_7$ is H or TBS; and $R_8$ is H, TBS, or TROC.

42. A method according to claim 41 wherein said fourth compound is further converted to Epothilone B.

43. A method according to claim 41 wherein $R_7$ and $R_8$ each are H.

44. A chemical compound formed according to the method of claim 35.

45. A method for use in producing epothilones and analogs and derivatives thereof, comprising:

(a) performing an aldol condensation of a first compound of the formula:

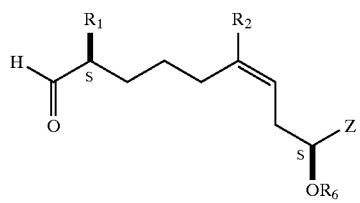

and stereoisomers thereof, with a second compound selected from the formulas:

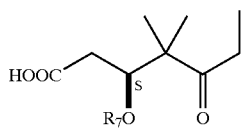

and stereoisomers thereof, thereby to form a third compound of the formula:

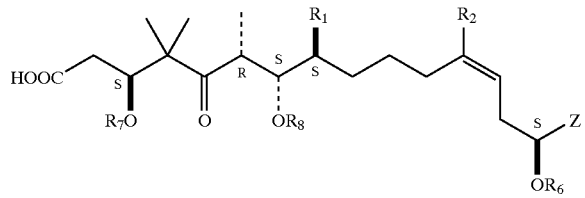

and stereoisomers thereof, wherein Z is

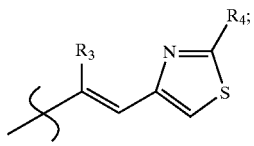

wherein $R_1$, $R_2$, $R_3$ and $R_4$ are each selected from H, alkyl, alkenyl, alkynyl, aryl, cycloalkyl, heterocyclo, and substitutions thereof;

$R_6$, $R_7$ and $R_8$ are each selected from H and a protecting group;

provided that $R_1$—$R_4$ of the first compound are not each methyl when $R_6$ is the protecting group TBS; and provided that $R_1$—$R_4$ of the third compound are not each methyl when $R_7$ is TBS, and $R_6$ and $R_8$ are hydrogen or the protecting group TBS;

(b) performing a macrolactonization of the third compound thereby to form a fourth compound of the formula:

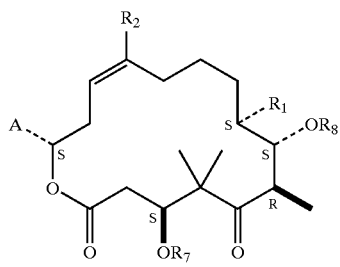

and stereoisomers thereof, wherein A is

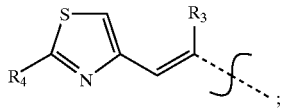

wherein $R_1$, $R_2$, $R_3$ and $R_4$ are each selected from H, alkyl, alkenyl, alkynyl, aryl, cycloalkyl, heterocyclo, and substitutions thereof;

$R_7$ and $R_8$ are each selected from H and a protecting group;

provided that $R_1$—$R_4$ of the fourth compound are not each methyl when $R_7$ and $R_8$ are either H or the protecting group TBS.

46. A method according to claim 45 wherein $R_1$, $R_3$ and $R_4$ are each methyl, and $R_2$ is H or methyl.

47. A method according to claim 46 wherein $R_2$ is methyl.

48. A method according to claim 46 wherein at least one of $R_6$—$R_8$ is TBS.

49. A method according to claim 46 wherein $R_6$, $R_7$ and $R_8$ are each TBS.

50. A method according to claim 45 wherein $R_6$ is selected from H, TBS, TMS, TIPS, PMBM and SEM; wherein $R_7$ is selected from H, TBS, TROC, —CO($CH_2)_4CH_3$ and —CO($CH_2)_3CH=CH_2$; and wherein $R_8$ is selected from H and TBS.

51. A method according to claim 45 wherein said fourth compound is of the formula:

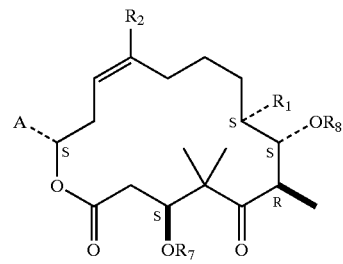

and stereoisomers thereof, wherein A is

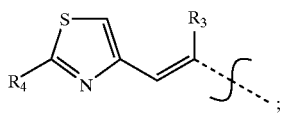

$R_2$ is H or methyl; $R_7$ is H or TBS; and $R_8$ is H, TBS, or TROC.

52. A method according to claim 51 wherein said fourth compound is further converted to Epothilone B.

53. A method according to claim 51 wherein $R_7$ and $R_8$ each are H.

54. A chemical compound formed according to the method of claim 45.

55. A chemical compound of the formula:

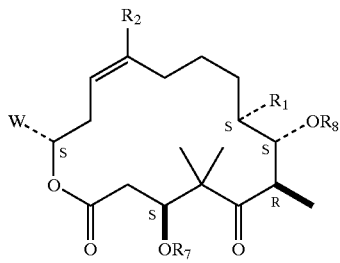

and stereoisomers thereof, wherein W is selected from

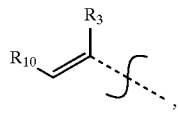

and

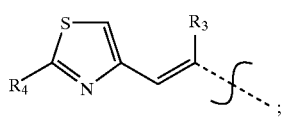

and wherein $R_1$, $R_2$, $R_3$ and $R_4$ are each selected from H, alkyl, alkenyl, alkynyl, aryl, cycloalkyl, heterocyclo, and substitutions thereof;

$R_7$ is $COR_{11}$;

$R_8$ is selected from H, a protecting group and $COR_{12}$;

$R_{11}$ and $R_{12}$ are each selected from alkyl, alkenyl, alkynyl, aryl, alkyl-aryl, alkyloxy, aryloxy, cycloalkyl, heterocyclo, amino, sulfo, and substitutions thereof.

56. A chemical compound according to claim 55 wherein at least one of $R_{11}$ and $R_{12}$ is selected from —$(CH_2)_xCH_3$ and —$(CH_2)_yCH=CH_2$, where x and y are integers.

57. A chemical compound according to claim 56 wherein x and y are selected from the integers 3 and 4.

58. A chemical compound according to claim 56 wherein x is 4 and y is 3.

59. A chemical compound according to claim 55 wherein W is

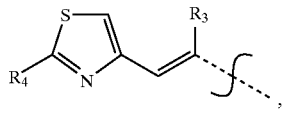

and wherein $R_2$ is H or methyl, $R_8$ is H or $COR_{12}$, and wherein $R_{11}$ and $R_{12}$ are each selected from —$(CH_2)_4CH_3$ and —$(CH_2)_3CH=CH_2$.

60. A chemical compound of the formula:

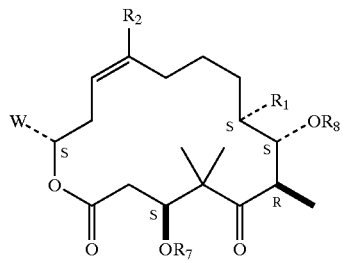

and stereoisomers thereof, wherein W is selected from

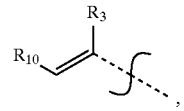

and

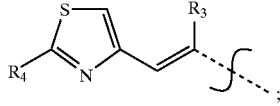

and wherein $R_1$, $R_2$, $R_3$ and $R_4$ are each selected from H, alkyl, alkenyl, alkynyl, aryl, cycloalkyl, heterocyclo, and substitutions thereof;

$R_7$ is selected from H, a protecting group and $COR_{11}$;

$R_8$ is $COR_{12}$;

$R_{11}$ and $R_{12}$ are each selected from alkyl alkenyl, alkynyl, aryl, alkyl-aryl, alkyloxy, aryloxy, cycloalkyl, heterocyclo, amino, sulfo, and substitutions thereof.

61. A chemical compound according to claim 60 wherein at least one of $R_{11}$ and $R_{12}$ is selected from —$(CH_2)_xCH_3$ and —$(CH_2)_yCH=CH_2$, where x and y are integers.

62. A chemical compound according to claim 61 wherein x and y are selected from the integers 3 and 4.

63. A chemical compound according to claim 61 wherein x is 4 and y is 3.

64. A chemical compound according to claim 60 wherein W is

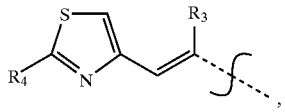

and wherein $R_2$ is H or methyl;

$R_7$ is H or $COR_{11}$; and $R_{11}$ and $R_{12}$ are each selected from —$(CH_2)_4CH_3$ and —$(CH_2)_3CH=CH_2$.

* * * * *